US012644896B2

(12) United States Patent
Guo et al.

(10) Patent No.: US 12,644,896 B2
(45) Date of Patent: Jun. 2, 2026

(54) MASS SPECTROMETRY BASED SYSTEMS AND METHODS FOR IMPLEMENTING MULTISTAGE MS/MS ANALYSIS FOR IDENTIFICATION OF EXPERIMENTAL GLYCOLIPID SAMPLES

(71) Applicant: University of Florida Research Foundation, Inc., Gainesville, FL (US)

(72) Inventors: Zhongwu Guo, Gainesville, FL (US);
Laura S. Bailey, Gainesville, FL (US);
Kari B. Basso, Gainesville, FL (US);
Fanran Huang, Gainesville, FL (US);
Tianqi Gao, Gainesville, FL (US);
Jinying Zhao, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 579 days.

(21) Appl. No.: 18/164,547

(22) Filed: Feb. 3, 2023

(65) Prior Publication Data

US 2023/0349934 A1     Nov. 2, 2023

Related U.S. Application Data

(63) Continuation-in-part of application No. PCT/US2021/044799, filed on Aug. 5, 2021.

(Continued)

(51) Int. Cl.
*G01N 33/92* (2006.01)
*H01J 49/00* (2006.01)

(52) U.S. Cl.
CPC .......... *G01N 33/92* (2013.01); *H01J 49/0036* (2013.01); *H01J 49/0068* (2013.01); *G01N 2560/00* (2013.01)

(58) Field of Classification Search
CPC . G01N 33/92; G01N 2560/00; H01J 49/0036; H01J 49/0068
See application file for complete search history.

(56) References Cited

U.S. PATENT DOCUMENTS 10,705,100 B1 * 7/2020 Hansen ................. G01N 33/92
2003/0082654 A1  5/2003 Parish et al.
(Continued)

FOREIGN PATENT DOCUMENTS

WO     WO-2019/232512 A1    12/2019

OTHER PUBLICATIONS

International Search Report and Written Opinion for Application No. PCT/US2021/044799, dated Nov. 16, 2021.
(Continued)

*Primary Examiner* — Catherine T. Rastovski
(74) *Attorney, Agent, or Firm* — MARSHALL, GERSTEIN & BORUN LLP

(57) ABSTRACT

Mass spectrometry (MS) based systems and methods of implementing multi-stage MS/MS analysis for identification of experimental glycolipid samples. A processor communicatively coupled to a memory and a reference spectral database (1) implements a first stage analysis of glycan fragment data including determining, based on a matching reference glycan of a candidate reference glycolipid, a glycan structure of a glycan portion of the experimental glycolipid. The processor further (2) implements a second stage analysis of lipid/glycolipid fragment data including determining a lipid structure of a lipid portion of the experimental glycolipid by performing a spectral comparison of one or more MS/MS spectral values of a shifted experimental lipid fragment data with one or more MS/MS spectral values of matching reference lipid/glycolipid fragment data of the candidate reference glycolipid. A combi-
(Continued)

nation of the determined glycan structure and lipid structure gives the structure of each specific glycolipid in the experimental glycolipid sample.

20 Claims, 26 Drawing Sheets

Related U.S. Application Data

(60) Provisional application No. 63/061,524, filed on Aug. 5, 2020.

(56) References Cited

U.S. PATENT DOCUMENTS

| | | | |
|---|---|---|---|
| 2012/0022230 A1* | 1/2012 | Smith | C07B 59/00 |
| | | | 564/291 |
| 2012/0197535 A1 | 8/2012 | Goodlett et al. | |
| 2020/0273545 A1* | 8/2020 | Ryu | G16C 20/20 |
| 2021/0104299 A1* | 4/2021 | Baba | H01J 49/0068 |

OTHER PUBLICATIONS

Koelmel, et al., LipidMatch: an automated workflow for rule-based lipid identification using untargeted high-resolution tandem mass spectrometry data, BMC Bioinformatics, 2017, 18:331.

* cited by examiner

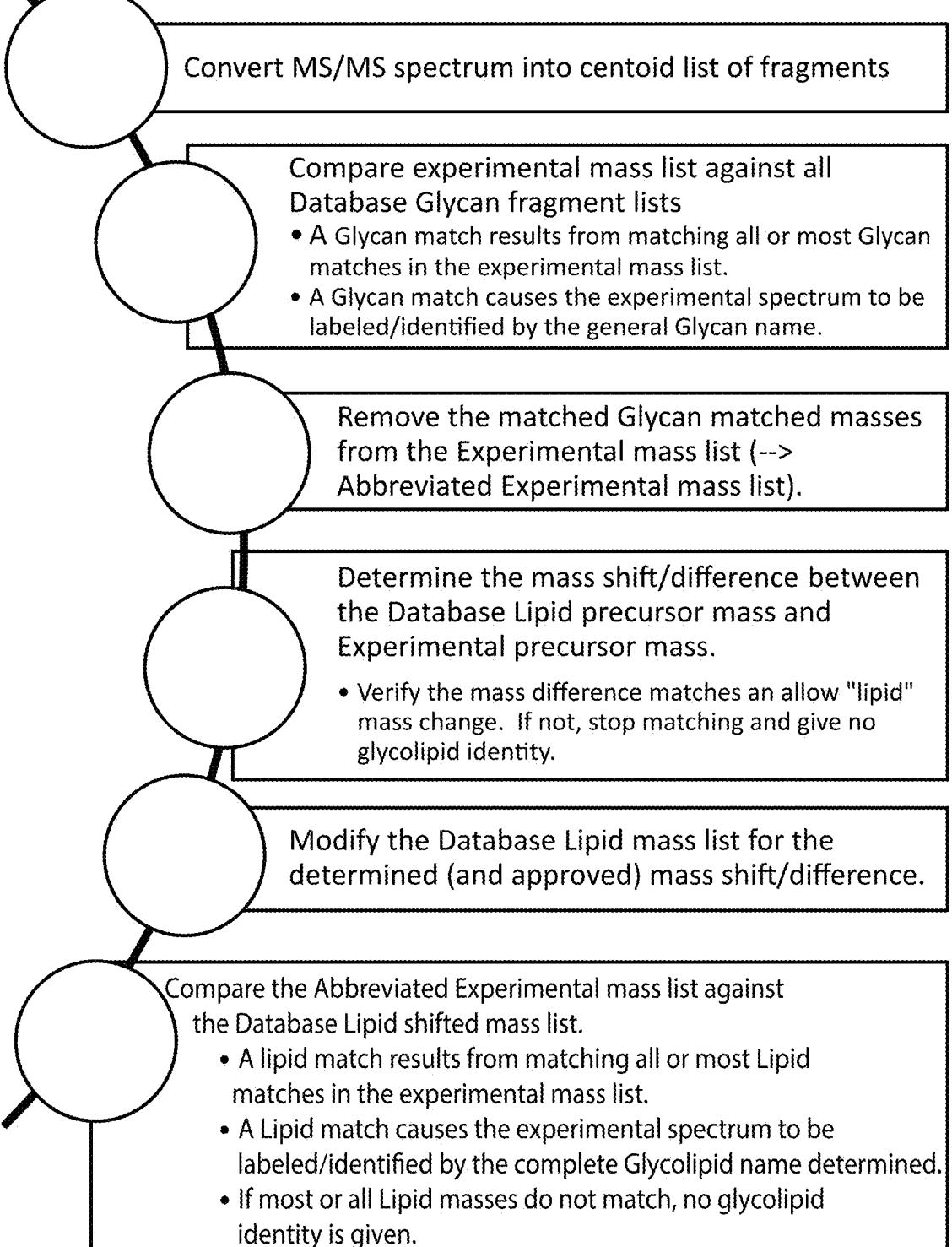

Convert MS/MS spectrum into centoid list of fragments

Compare experimental mass list against all Database Glycan fragment lists
• A Glycan match results from matching all or most Glycan matches in the experimental mass list.
• A Glycan match causes the experimental spectrum to be labeled/identified by the general Glycan name.

Remove the matched Glycan matched masses from the Experimental mass list (--> Abbreviated Experimental mass list).

Determine the mass shift/difference between the Database Lipid precursor mass and Experimental precursor mass.
• Verify the mass difference matches an allow "lipid" mass change. If not, stop matching and give no glycolipid identity.

Modify the Database Lipid mass list for the determined (and approved) mass shift/difference.

Compare the Abbreviated Experimental mass list against the Database Lipid shifted mass list.
• A lipid match results from matching all or most Lipid matches in the experimental mass list.
• A Lipid match causes the experimental spectrum to be labeled/identified by the complete Glycolipid name determined.
• If most or all Lipid masses do not match, no glycolipid identity is given.

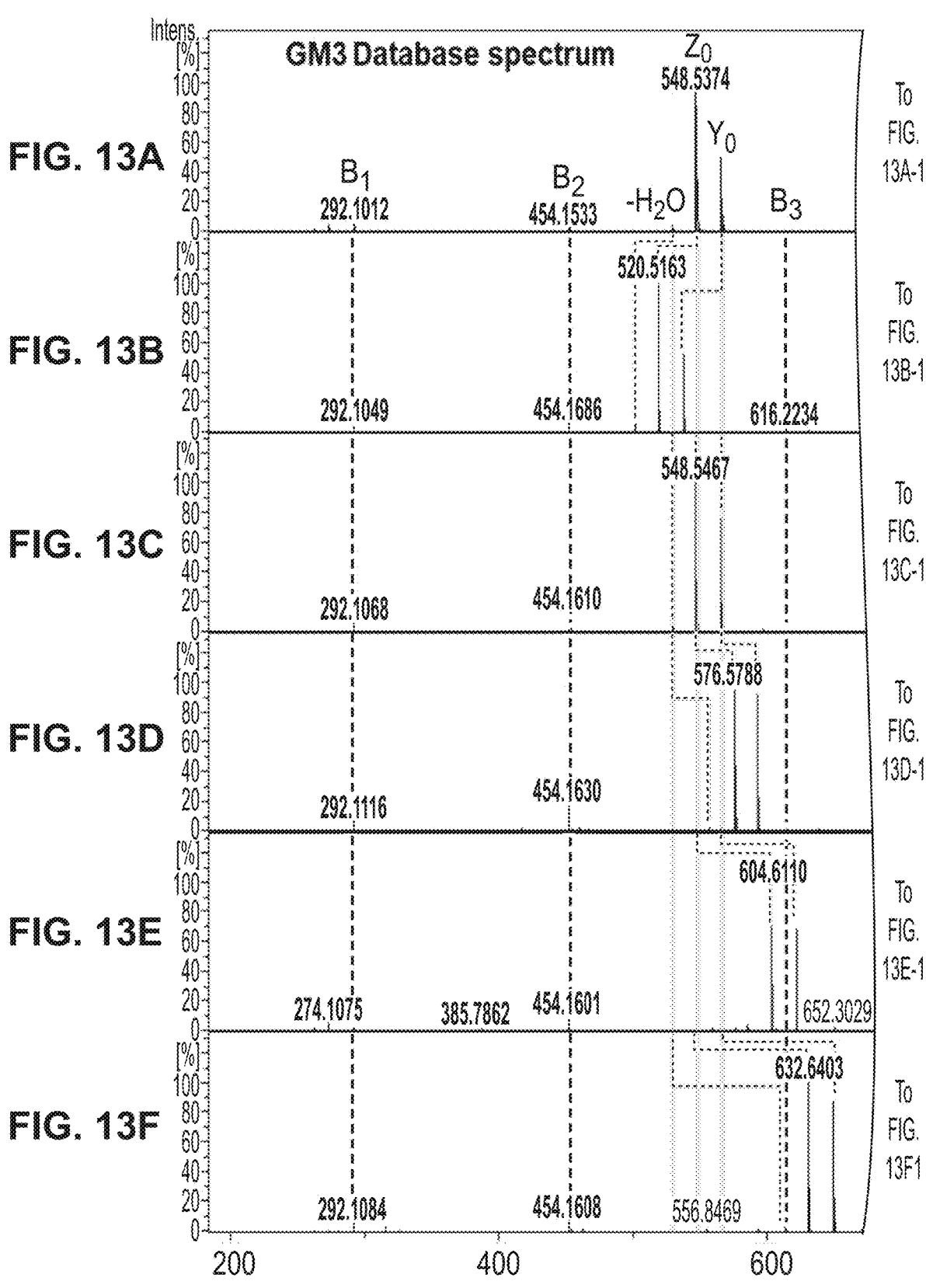

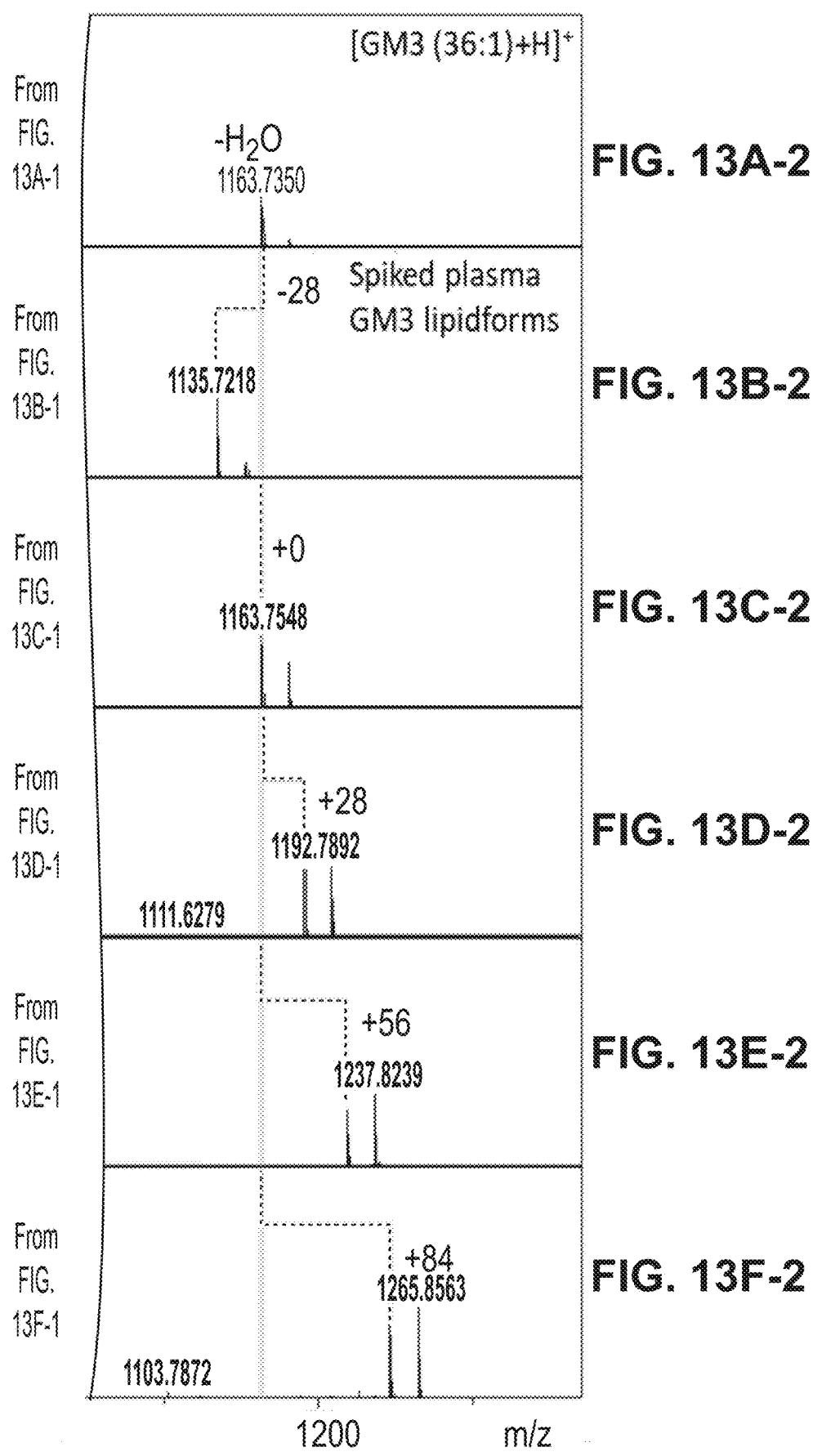
From FIG. 13A-1    FIG. 13A-2
From FIG. 13B-1    FIG. 13B-2
From FIG. 13C-1    FIG. 13C-2
From FIG. 13D-1    FIG. 13D-2
From FIG. 13E-1    FIG. 13E-2
From FIG. 13F-1    FIG. 13F-2

LC-IMS-MS/MS of GD1a/b mix standard
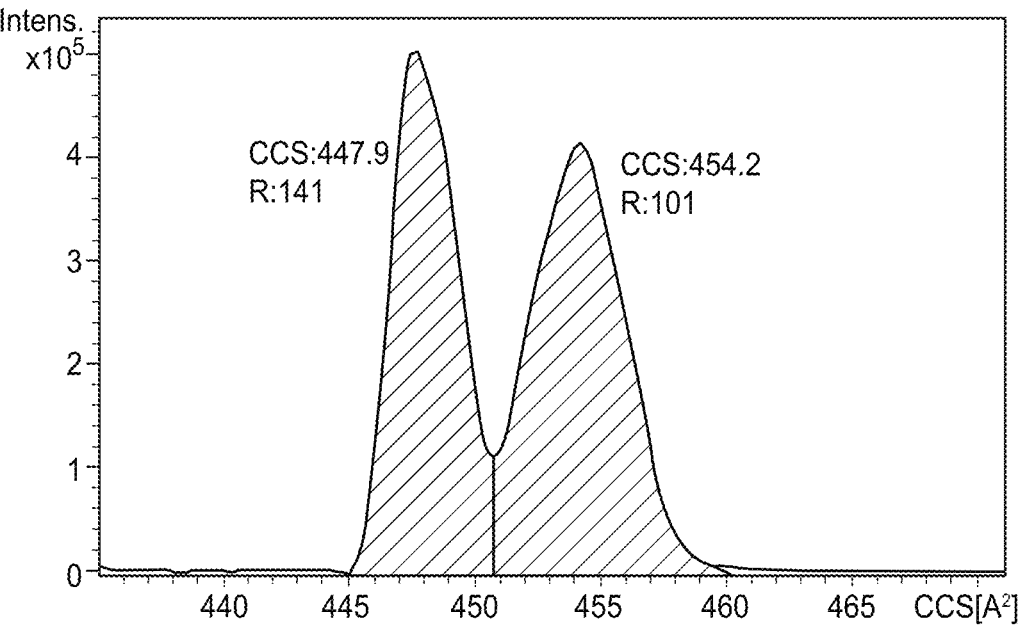
Glycolipid - GD1a and GD1b
MS/MS
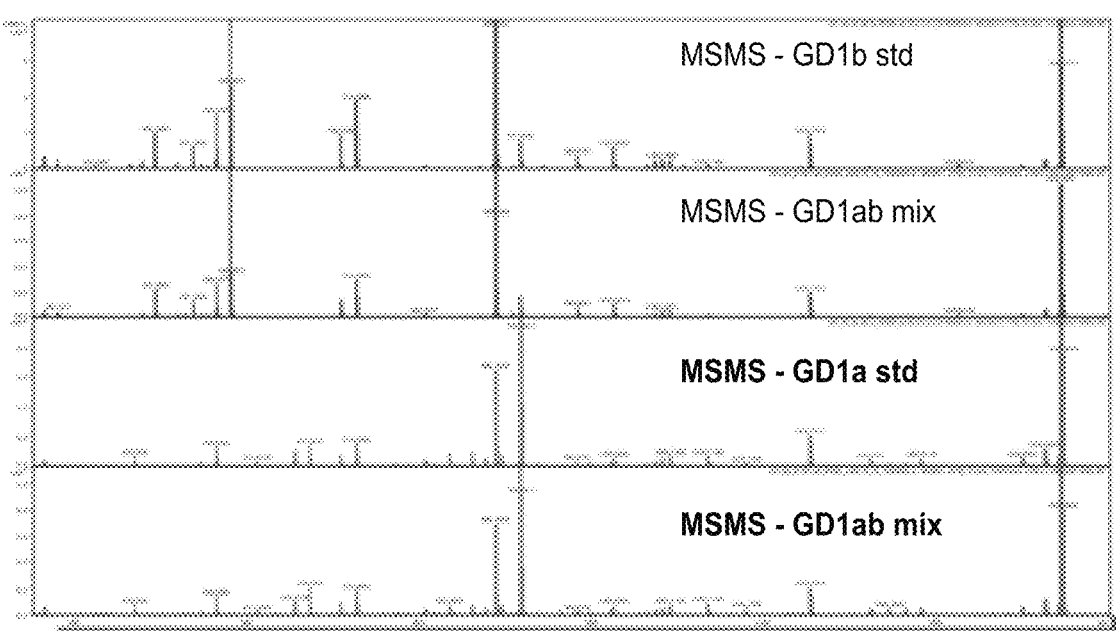
FIG. 15

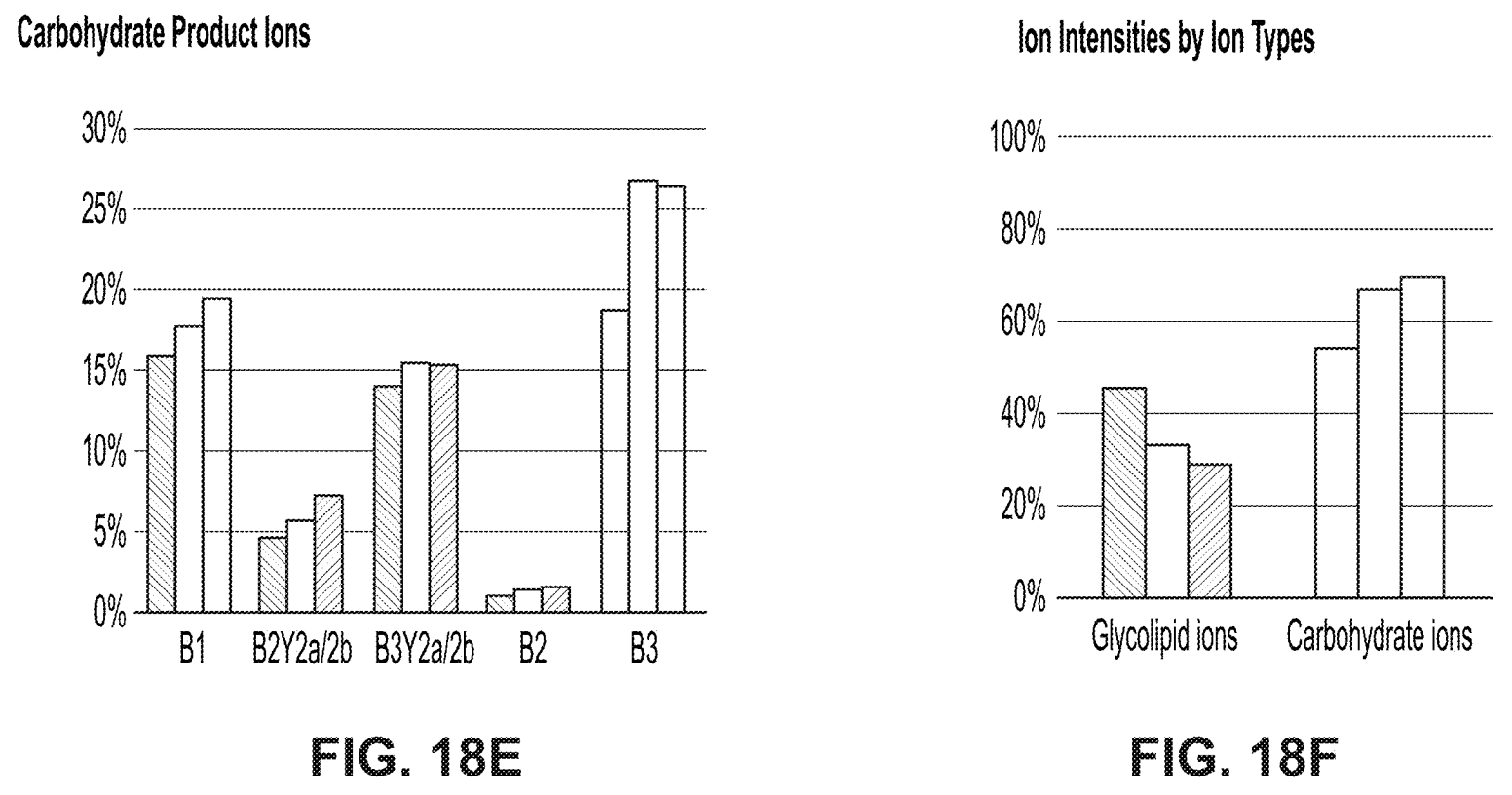

Ion Intensities by Ion Types

100%

80%

60%

40%

20%

0%

Glycolipid ions    Carbohydrate ions

FIG. 18F

Carbohydrate Product Ions

MASS SPECTROMETRY BASED SYSTEMS AND METHODS FOR IMPLEMENTING MULTISTAGE MS/MS ANALYSIS FOR IDENTIFICATION OF EXPERIMENTAL GLYCOLIPID SAMPLES

CROSS-REFERENCE TO RELATED APPLICATIONS

This application is a continuation-in-part of PCT Application No. PCT/US21/44799, filed Aug. 5, 2021, which claims the benefit under 35 U.S.C. § 119(e) of U.S. Provisional Application No. 63/061,524, filed Aug. 5, 2020, the entire disclosures of which are hereby incorporated by reference.

STATEMENT OF GOVERNMENT SUPPORT

This invention was made with government support under Grant No. 1800279, awarded by the National Science Foundation. The government has certain rights in this invention.

FIELD OF THE DISCLOSURE

The present disclosure generally relates to mass spectrometry (MS) based systems and methods, and, more particularly, to MS based systems and methods for implementing multistage MS/MS analysis for identification of experimental glycolipid samples.

BACKGROUND

Glycan-lipid conjugates, known as glycolipids, are found at cell membranes and play an important role in various physiological and pathological processes. Glycolipids of cells in the central nervous system are related to many diseases such as cancer, Alzheimer's disease, and depression, among others. Accordingly, the ability to analyze and identify glycolipids in bodily fluids, such as plasma, and in tissues would be useful to identify specific molecular biomarkers useful for disease diagnosis and therapy.

Currently, the analysis of glycolipids remains a formidable challenge due to their unique physical and chemical properties. In particular, glycolipids are highly diverse in both the glycan and the lipid compositions, making their structural characterization extremely complicated. The typical process for liquid chromatography tandem mass spectrometry (LC-MS/MS)-based glycolipid analysis of unknown samples is: glycolipids are isolated from biological sources and then subjected to LC-MS/MS; the resultant experimental spectra are finally uploaded to a program to be compared to spectra in a database of known glycolipids. To identify a positive match, a product spectrum needs to be physically present in the database. These matches (or annotated identities) are further scored based on how well the experimental MS/MS spectrum matches the database (or references) MS/MS spectrum. The better the match, the higher the identification score, indicating a high probability that the experimental glycolipid is the glycolipid from the database. Current libraries/databases contain only a fractional number of MS/MS spectra for glycolipids, resulting in many natural glycolipids going unmatched and unidentified. However, the countless possible glycan-lipid combinations make a comprehensive library/database difficult to attain.

It is well known that the totality of lipids in a biological system (lipidome) is immense and access to all lipid forms is a daunting or nearly impossible task. But the predictable nature of lipid fragmentation patterns has provided a unique and creative solution to this challenge. Rule-based libraries and related matching programs, such as LipdMatch (R A Yost, et al. *BMC Bioinformatics* 2017, 18, 331), are applied. In short, these matching programs can operate by containing only a small reference library (e.g., a few examples of each lipid class), and any lipid forms that are not physically present in the database are projected for experimental spectral matching through uniformly shifting the reference fragment masses by a certain number. However, this strategy is not applicable to glycolipids because of the presence of the glycan. In particular, current rule-based methodology shifts all ions in the reference spectrum by a defined lipid mass to provide the projected rule-based reference spectrum. When the rule-based reference spectrum of a glycolipid is compared to the experimental spectrum, only partial spectral match is observed (i.e., fragment ions containing the lipid moiety) because glycans follow different fragmentation rules than lipids. The ultimate result is a low matching score and no identification of the glycolipid.

For the foregoing reasons, there is a need for MS based systems and methods for implementing MS/MS analysis for identification of experimental glycolipid samples.

BRIEF SUMMARY

The systems and methods of the disclosure can advantageously be used to identify and analyze unknown glycolipid samples, without the need for a comprehensive glycolipid library/database. Further advantageously, the systems and methods of the disclosure can be used to increase the number of known glycolipid structures that can be added to a glycolipid library/database for use in traditional MS/MS methods. The ability to identify unknown glycolipids and expand the libraries of known glycolipids can advantageously facilitate identification of new specific molecular biomarkers useful for disease diagnosis and therapy.

Accordingly, in various embodiments, the present disclosure describes a mass spectrometry (MS) based system configured to implement multi-stage MS, MS/MS analysis for identification of experimental glycolipid samples. The MS based system may include a mass spectrometer configured to receive and analyze an experimental glycolipid sample to determine experimental MS/MS spectral data of the experimental glycolipid sample. The MS based system may further include a reference spectral database configured to store a plurality of reference glycolipid datasets, each of the reference glycolipid datasets corresponding to a reference glycolipid and comprising at least (a) reference glycan fragment data defining MS/MS spectra of a glycan portion of the reference glycolipid, and (b) reference lipid/glycolipid fragment data defining MS/MS spectra of a lipid portion of the reference glycolipid. The MS based system may further include a memory storing program instructions. The MS based system may further include a processor communicatively coupled to the memory and the reference spectral database. In various embodiments, the processor may be configured to execute the program instructions to cause the processor to: (1) implement a first stage analysis of glycan fragment data comprising: determining, from the experimental MS/MS spectral data, experimental glycan fragment data defining MS/MS spectra of a glycan portion of the experimental glycolipid sample, identifying a matching reference glycan of a candidate reference glycolipid selected from the reference spectral database, wherein fragment data of the matching reference glycan comprises one or more MS/MS spectral values that correspond to one or more MS/MS spectral values of the experimental glycan fragment data, determining, based on the matching reference glycan of the candidate reference glycolipid, a glycan structure of the glycan portion of the experimental glycolipid. The processor may further be configured to execute the program instructions to cause the processor to: (2) implement a second stage analysis of lipid/glycolipid fragment data comprising: determining, from the experimental MS/MS spectral data, experimental lipid fragment data defining MS/MS spectra of a lipid portion of the experimental glycolipid sample, shifting one or more mass values of the reference lipid/glycolipid fragment data of the candidate reference glycolipid to generate shifted reference lipid/glycolipid fragment data, performing a spectral comparison of one or more MS/MS spectral values of the shifted reference lipid/glycolipid fragment data with one or more MS/MS spectral values of the experimental lipid fragment data, and determining, based on reference lipid/glycolipid fragment data of the candidate reference glycolipid, a lipid structure of the lipid portion of the experimental glycolipid. Based on the spectral comparison, the experimental glycolipid sample is determined to be of a same glycolipid species as the candidate reference glycolipid, the lipid structure of the lipid portion of the experimental glycolipid being different from a lipid structure of the candidate reference glycolipid as characterized by a difference between the experimental lipid/glycolipid fragment data and the reference lipid/glycolipid fragment data.

Additionally, in various embodiments, the present disclosure describes a mass spectrometry (MS) based method of implementing multi-stage MS/MS analysis for identification of experimental glycolipid samples. The MS based method includes (1) implementing, by a processor communicatively coupled to a memory and a reference spectral database, a first stage analysis of glycan fragment data comprising: determining, from experimental MS/MS spectral data of an experimental glycolipid sample as analyzed by a mass spectrometer, experimental glycan fragment data defining MS/MS spectra of a glycan portion of the experimental glycolipid sample, identifying a matching reference glycan of a candidate reference glycolipid selected from the reference spectral database. The spectral database may store a plurality of reference glycolipid datasets, each of the reference glycolipid datasets corresponding to a reference glycolipid and comprising at least (a) reference glycan fragment data defining MS/MS spectra of a glycan portion of the reference glycolipid, and (b) reference lipid/glycolipid fragment data defining MS/MS spectra of a lipid portion of the reference glycolipid, and wherein fragment data of the matching reference glycan comprises one or more MS/MS spectral values that correspond to one or more MS/MS spectral values of the experimental glycan fragment data, and determining, based on the matching reference glycan of the candidate reference glycolipid, a glycan structure of the glycan portion of the experimental glycolipid. The MS based method may further include (2) implementing, by the processor, a second stage analysis of lipid/glycolipid fragment data comprising: determining, from the experimental MS/MS spectral data, experimental lipid/glycolipid fragment data defining MS/MS spectra of a lipid portion of the experimental glycolipid sample, shifting one or more mass values of the reference lipid/glycolipid fragment data of the candidate reference glycolipid to generate shifted reference lipid/glycolipid fragment data, performing a spectral comparison of one or more MS/MS spectral values of the shifted reference lipid/glycolipid fragment data with one or more MS/MS spectral values of the experimental lipid/glycolipid fragment data, and determining, based on reference lipid/glycolipid fragment data of the candidate reference glycolipid, a lipid structure of the lipid portion of the experimental glycolipid. Based on the spectral comparison, the experimental glycolipid sample may be determined to be of a same glycolipid species as the candidate reference glycolipid, the lipid structure of the lipid portion of the experimental glycolipid being different from a lipid structure of the candidate reference glycolipid as characterized by a difference between the experimental lipid/glycolipid fragment data and the reference lipid/glycolipid fragment data.

In various embodiments, a combination of the determined glycan structure and lipid structure gives the structure of each specific glycolipid in the experimental glycolipid sample. It can be of a same glycolipid species as the candidate reference glycolipid or a glycolipid species containing a different lipid from that of the candidate reference glycolipid.

Advantages will become more apparent to those of ordinary skill in the art from the following description of the preferred embodiments, which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein.

US 12,644,896 B2

5

Figure 6:
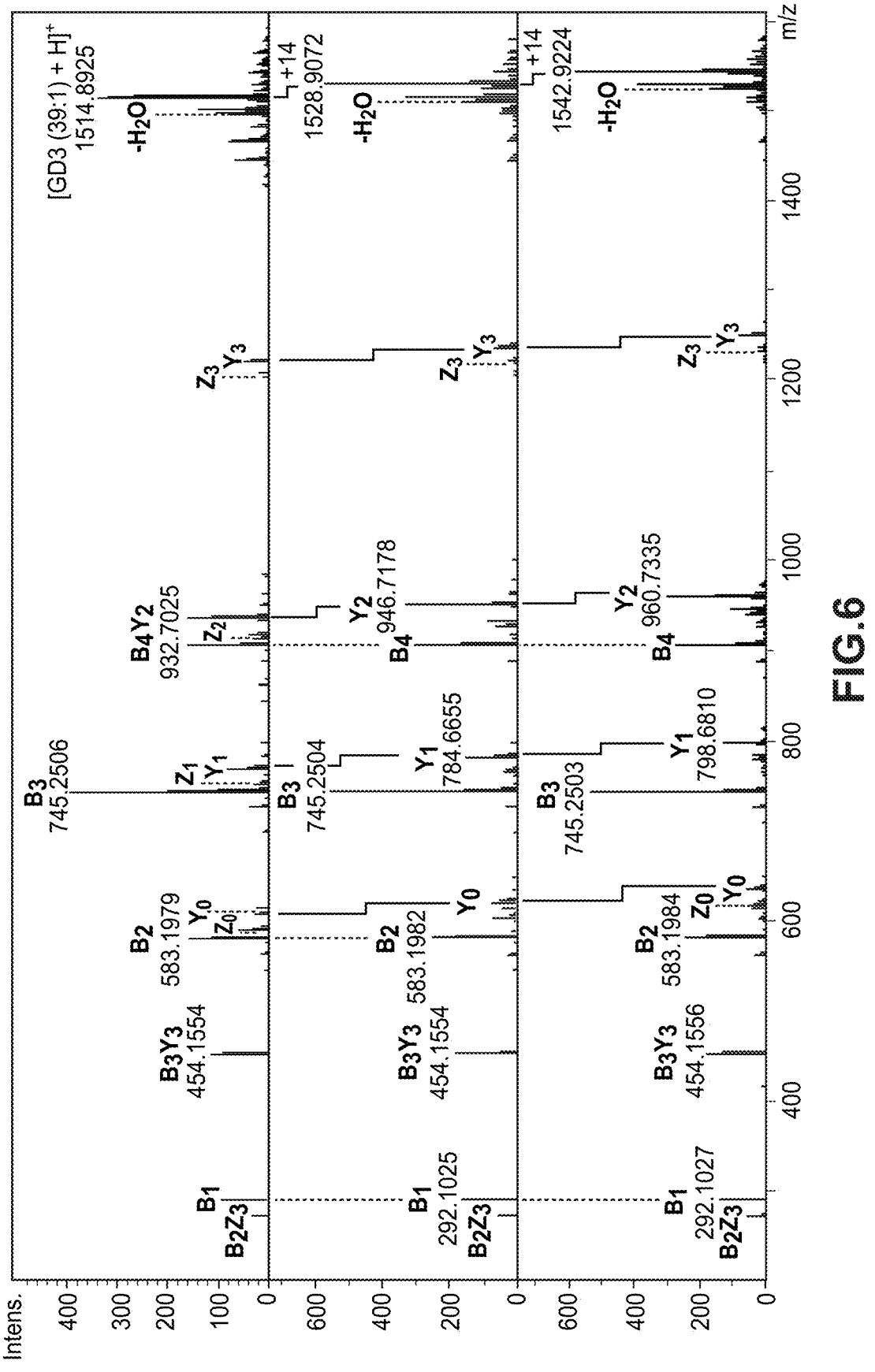

FIG. 6 illustrates a comparison of the MS/MS spectra of different lipid forms of GD3: (39:1) (top), (40:1) middle, and (41:1) (bottom).

Figure 7:
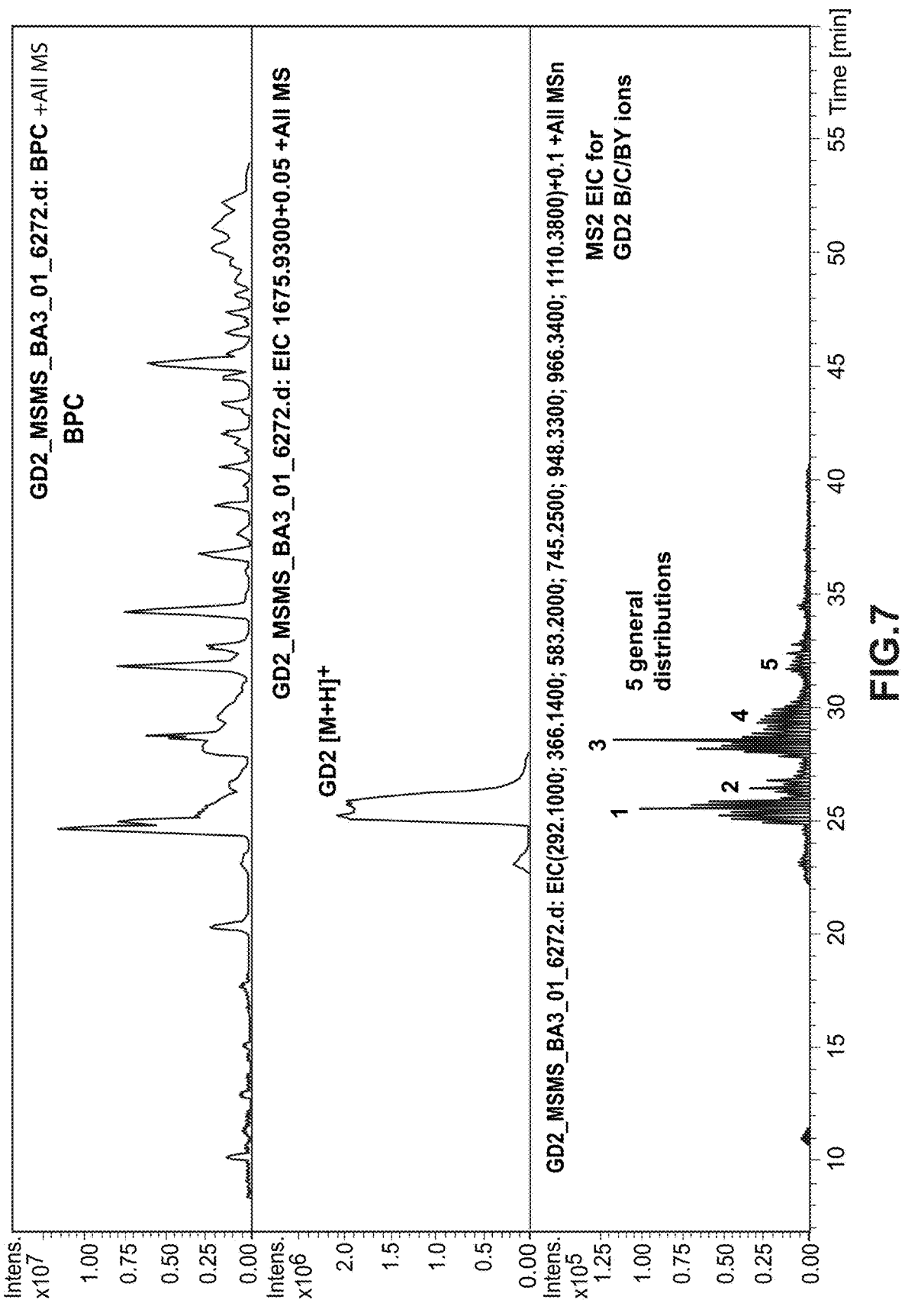

FIG. 7 illustrates LC-MS/MS chromatographic traces of a commercial GD2 sample, showing the base peak chromatogram (top), the search results using traditional methods and libraries (middle), and the search results using methods in accordance with various embodiments disclosed herein (bottom).

Figure 8:
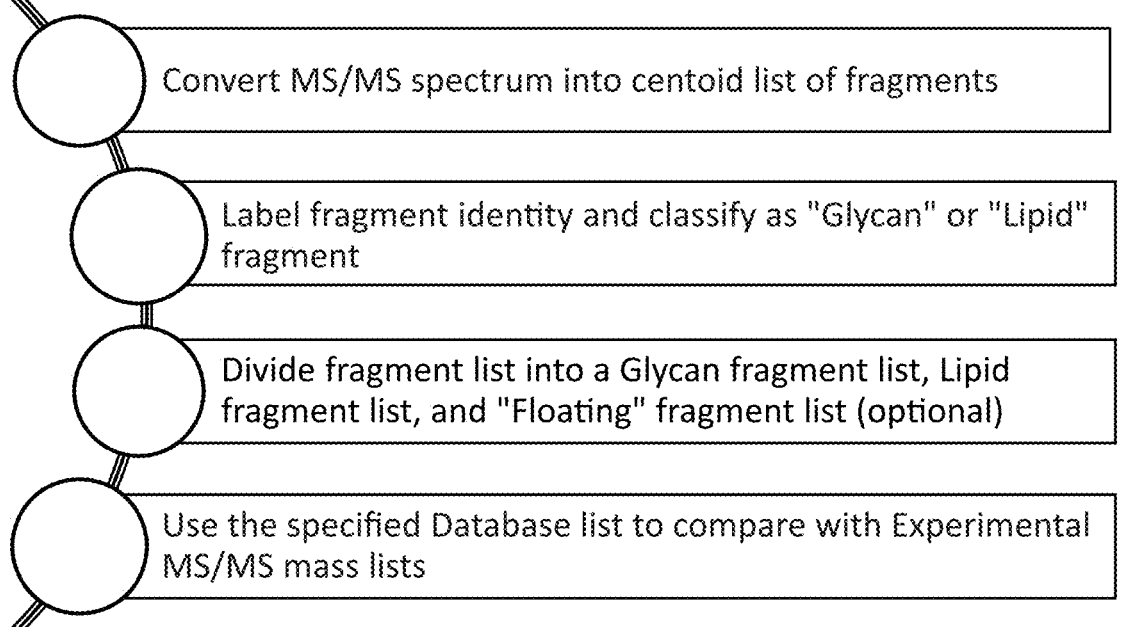

FIG. 8 illustrates a workflow for database entry, in accordance with various embodiments disclosed herein.

FIG. 9 illustrates a workflow for experimental glycolipid searching, in accordance with various embodiments disclosed herein.

Figure 10:
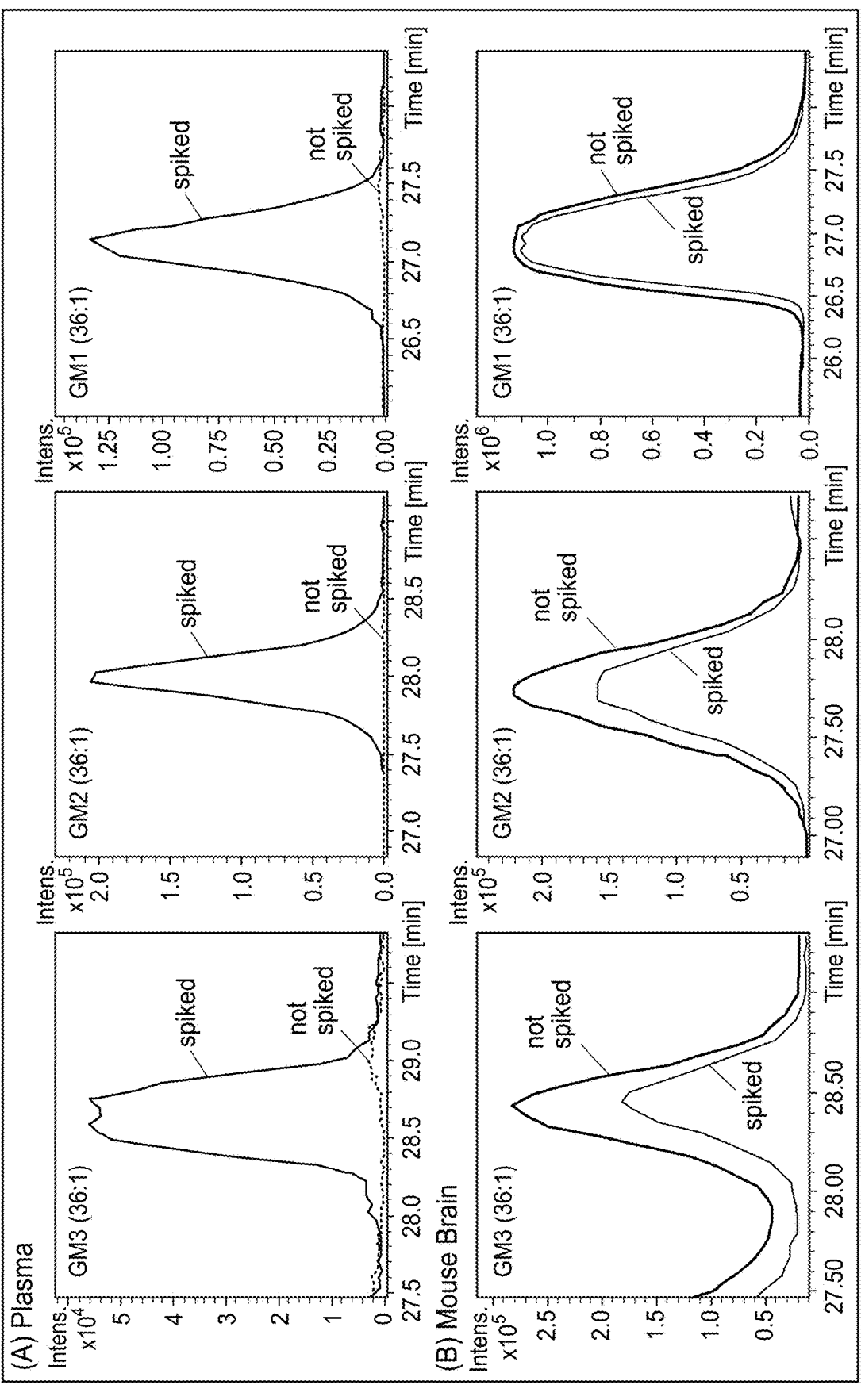

FIG. 10 illustrates an extracted ion chromatogram (EIC) of GM3, GM2, and GM1 in plasma (top) and mouse brain (bottom).

Figures 11A, 11B, 11C:
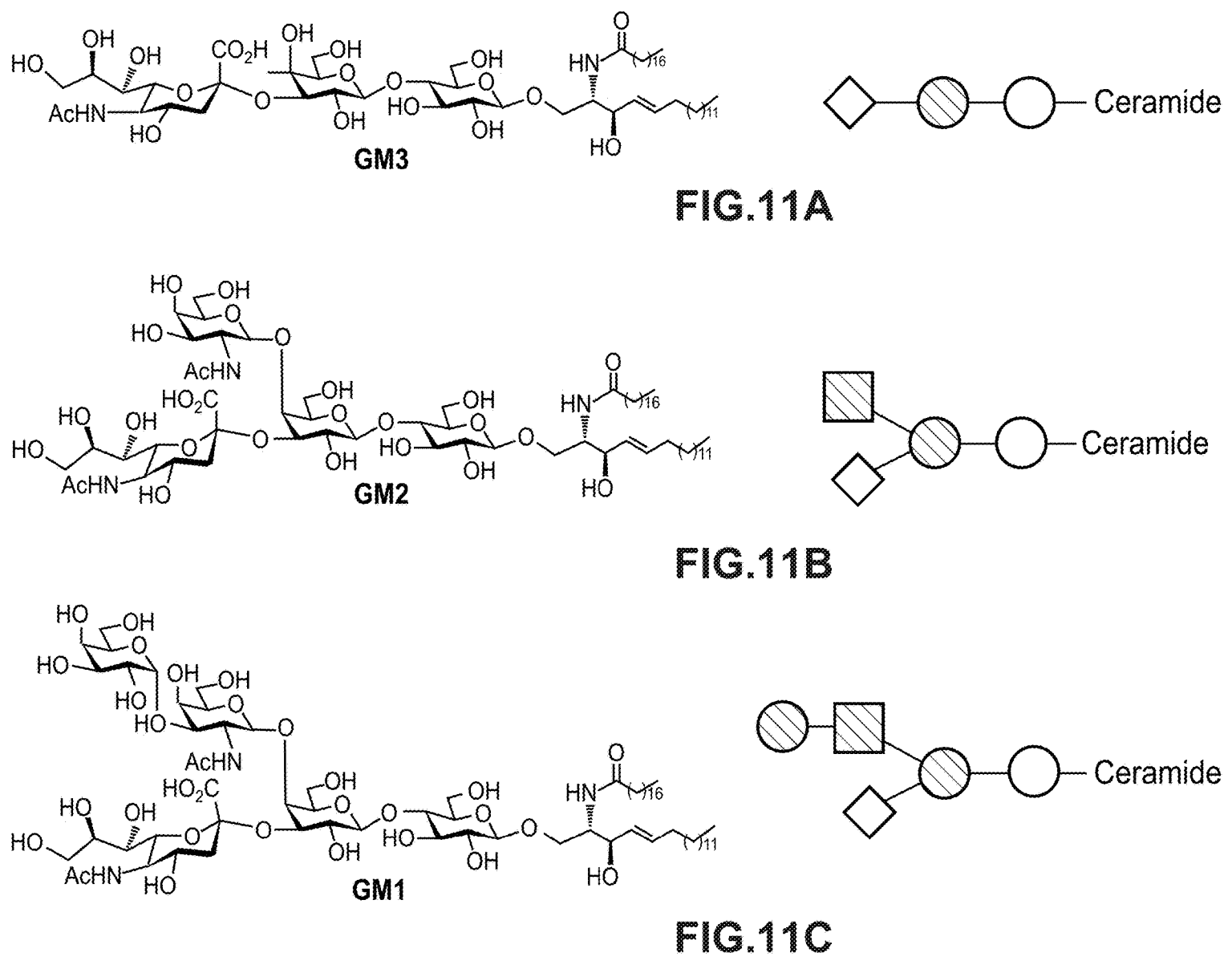

FIG. 11A illustrates GM3 chemically and using carbohydrate symbolic representations.

FIG. 11B illustrates GM2 chemically and using carbohydrate symbolic representations.

FIG. 11C illustrates GM1 chemically and using carbohydrate symbolic representations.

Figure 12:
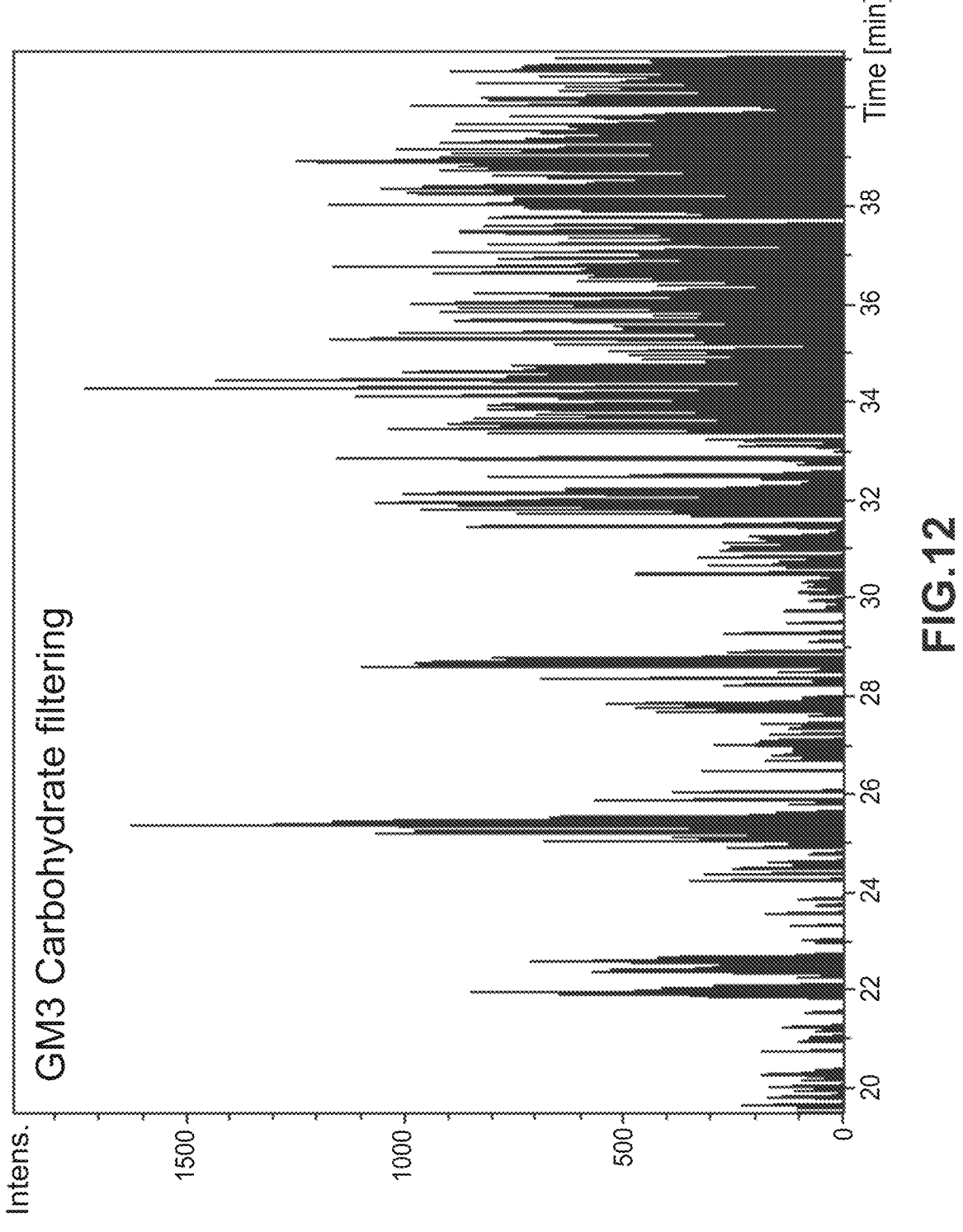

FIG. 12 is a MSMS EIC spectra containing the GM3 carbohydrate ion masses m/z 292.10, 454.15, and 616.20+/−0.05.

Figures 1, 13A, 13B, 13C, 13D, 13E, 13F:
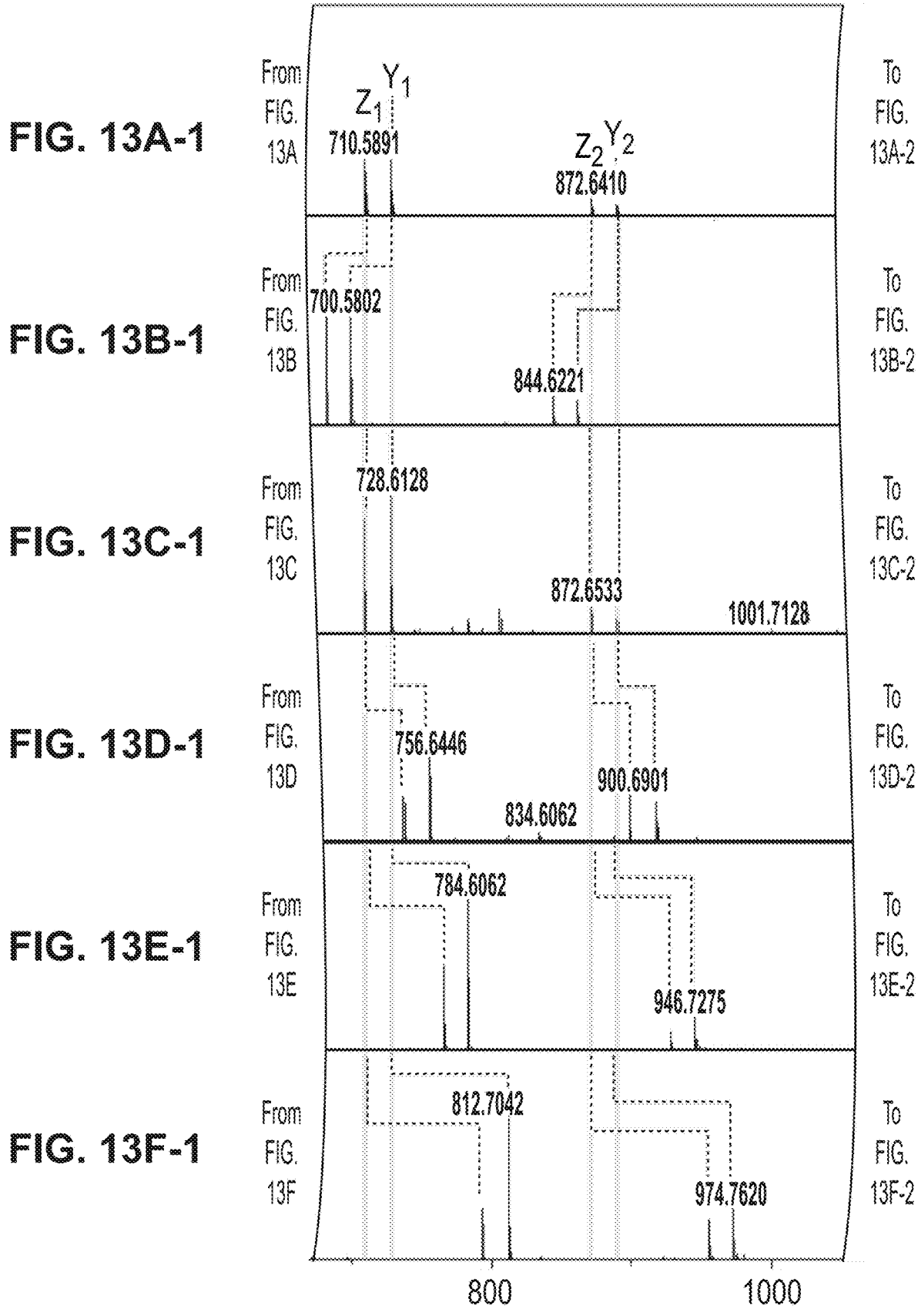

FIG. 13A is a MSMS spectrum of GM3 (36:1) from a reference data base.

FIG. 13B is MSMS spectrum of a GSL from a spiked plasma sample, showing glycolipid ions shifted −28 m/z from the reference spectrum in FIG. 13A, identifying the GSL as GM3 (34:1).

FIG. 13C is MSMS spectrum of a GSL from a spiked plasma sample, showing glycolipid ions shifted 0 m/z from the reference spectrum in FIG. 13A, identifying the GSL as GM3 (36:1).

FIG. 13D is MSMS spectrum of a GSL from a spiked plasma sample, showing glycolipid ions shifted +28 m/z from the reference spectrum in FIG. 13A, identifying the GSL as GM3 (38:1).

FIG. 13E is MSMS spectrum of a GSL from a spiked plasma sample, showing glycolipid ions shifted +56 m/z from the reference spectrum in FIG. 13A, identifying the GSL as GM3 (40:1).

FIG. 13F is MSMS spectrum of a GSL from a spiked plasma sample, showing glycolipid ions shifted +84 m/z from the reference spectrum in FIG. 13A, identifying the GSL as GM3 (42:1).

Figure 14:
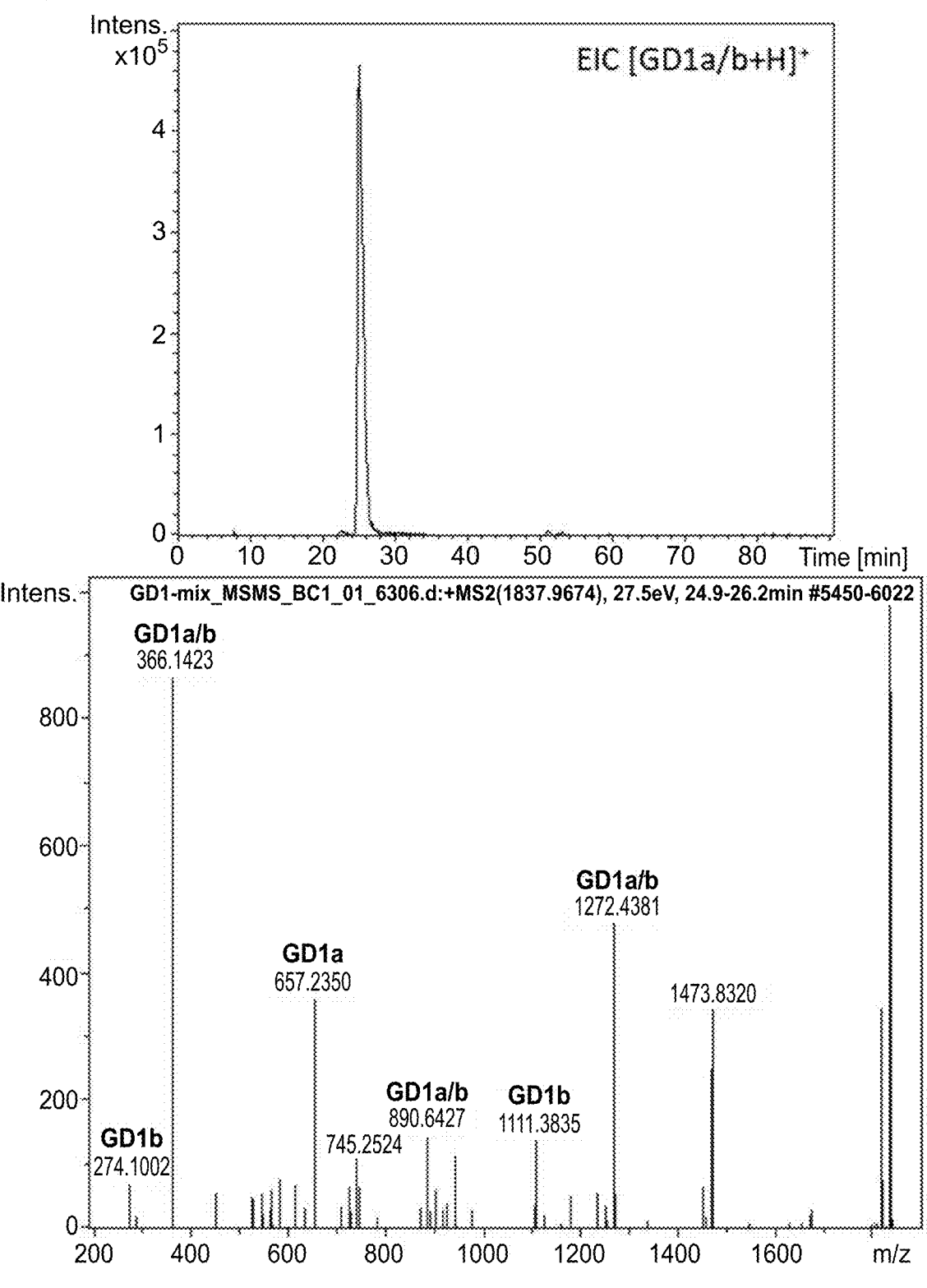

FIG. 14 is an LC-MS/MS analysis of a chromatographically unresolved GD1a and GD1b peak (top) which results in an overlapping product spectrum containing product ions from both precursors (bottom).

FIG. 15 is an LC-IMS-MS/MS chromatogram showing GD1a and GD1b isobar separation (top) and MS/MS spectra for each isomer (bottom).

Figures 16, 17:
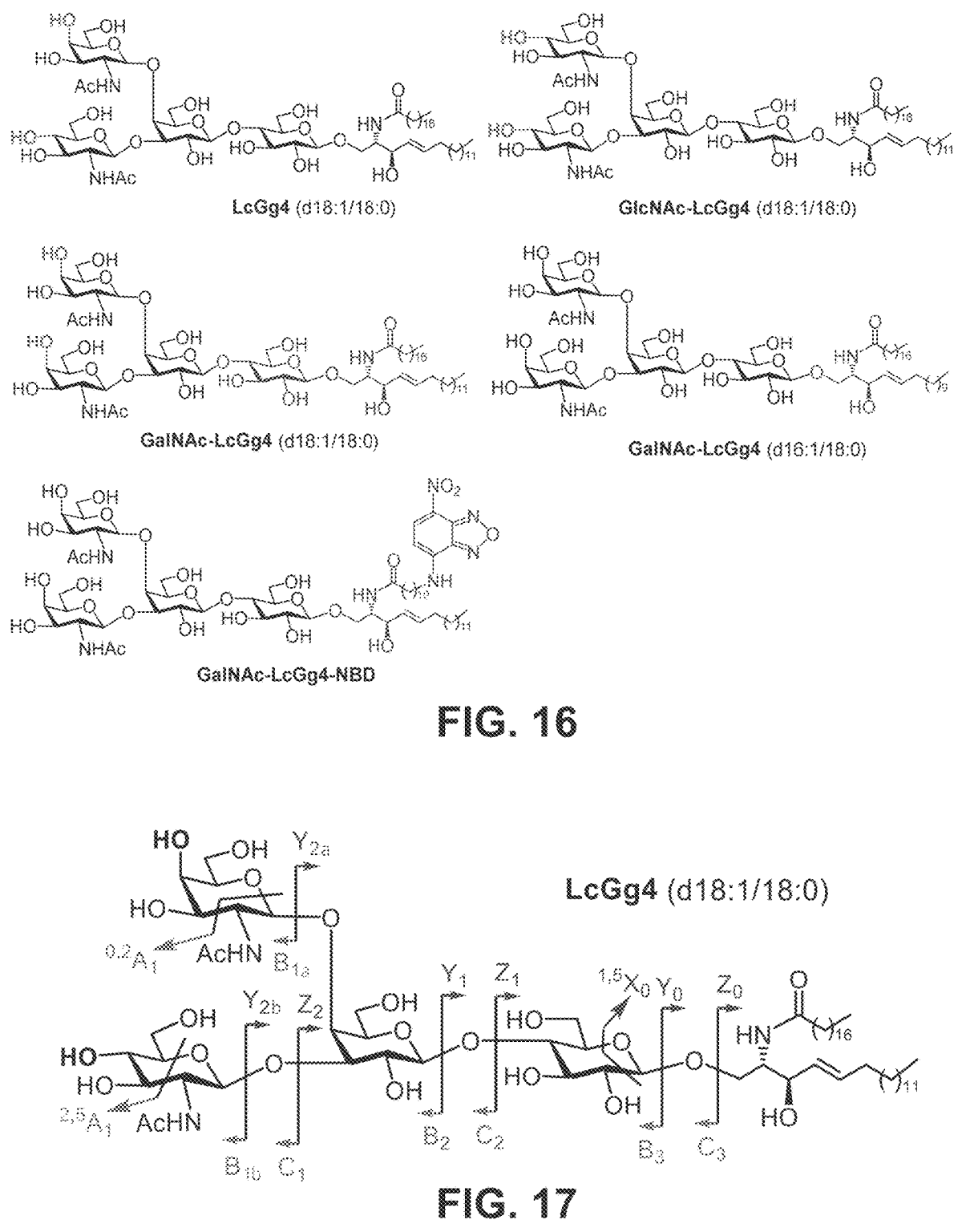

FIG. 16 shows five (5) synthetic GSLs.

FIG. 17 shows representative MS/MS product ions of LcGg4 following the common fragmentation patterns of GSLs, as well as their nomenclature. The line indicates bond cleavage, and the arrow shows the direction of charge retention. The subscript number indicates the number of sugar residues retained in the product ion, while superscript numbers indicate the two cleaved bonds within a sugar ring (for A and X fragments only). A, B, and C ions contain only the glycan fragments, while X, Y, and Z ions contain both the glycan fragments and the ceramide.

6

Figures 18A, 18B:
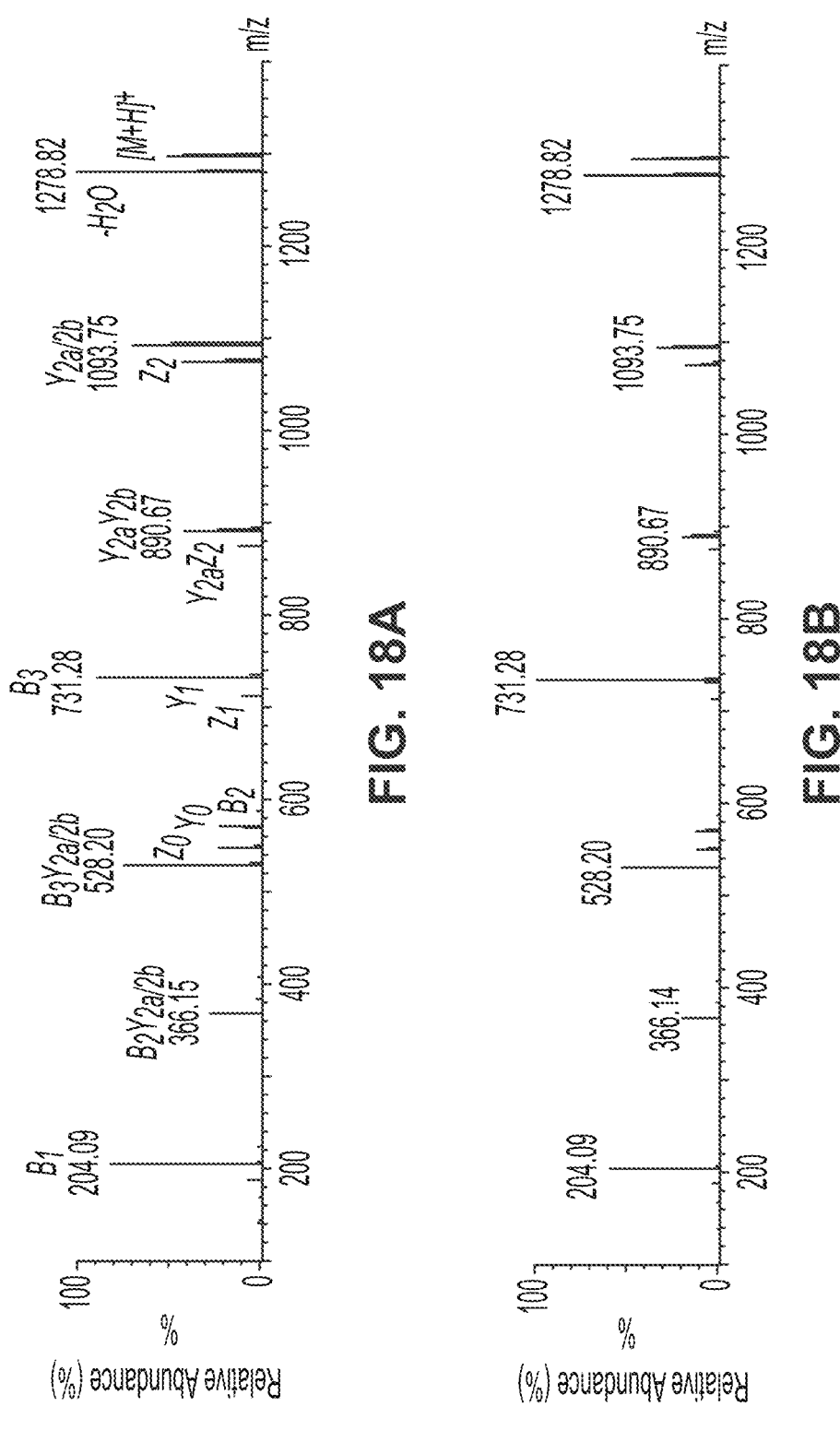

FIG. 18A shows the MS/MS spectra of GalNAc-LcGg4, with a collision energy of 25 eV with [M+H]+ as the parent ion.

FIG. 18B shows the MS/MS spectra of LcGg4, with a collision energy of 25 eV with [M+H]+ as the parent ion.

Figure 18C:
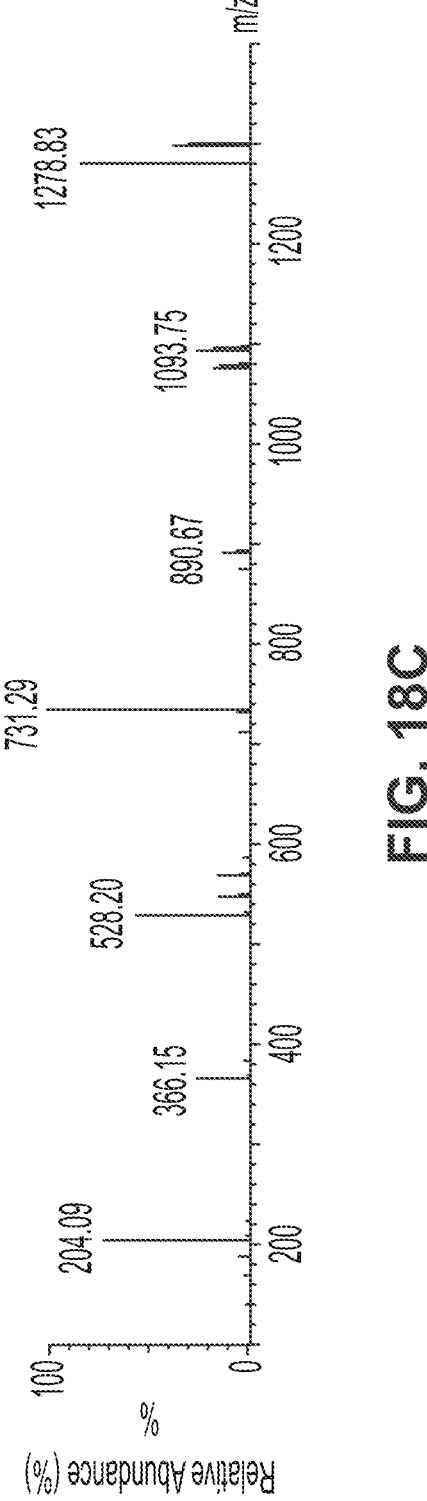

FIG. 18C shows the MS/MS spectra of GlcNAc-LcGg4, with a collision energy of 25 eV with [M+H]+ as the parent ion.

Figure 18D:
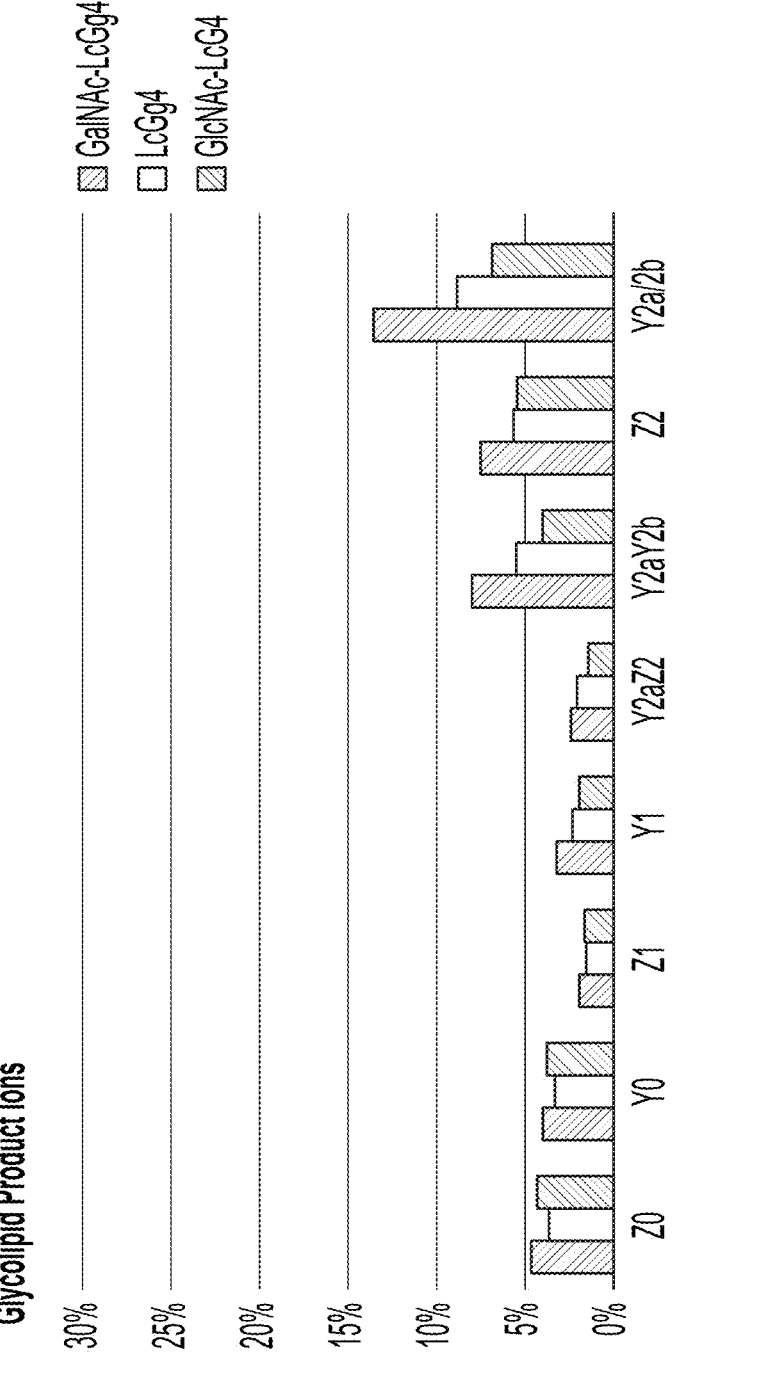

FIG. 18D shows the relative intensities of glycolipid product ions (Y and Z) for GalNac-LcGg4, LcGg4, and GlcNAc-LcGg4 (left, middle, and right bars, respectively) in the MS/MS spectra. The vertical axis shows the percentage of each ion or each type of ions against the combination of all identified carbohydrate and glycolipid ions.

FIG. 18E shows the relative intensities of carbohydrate product ions (B and BY) for GalNAc-LcGg4, LcGg4, and GlcNAc-LcGg4 (left, middle, and right bars, respectively) in the MS/MS spectra. The vertical axis shows the percentage of each ion or each type of ions against the combination of all identified carbohydrate and glycolipid ions.

FIG. 18F shows the relative intensities of the combined carbohydrate product ions and combined glycolipid product ions (B and BY) for GalNAc-LcGg4, LcGg4, and GlcNAc-LcGg4 (left, middle, and right bars, respectively) in the MS/MS spectra. The vertical axis shows the percentage of each ion or each type of ions against the combination of all identified carbohydrate and glycolipid ions.

Figures 19A, 19B:
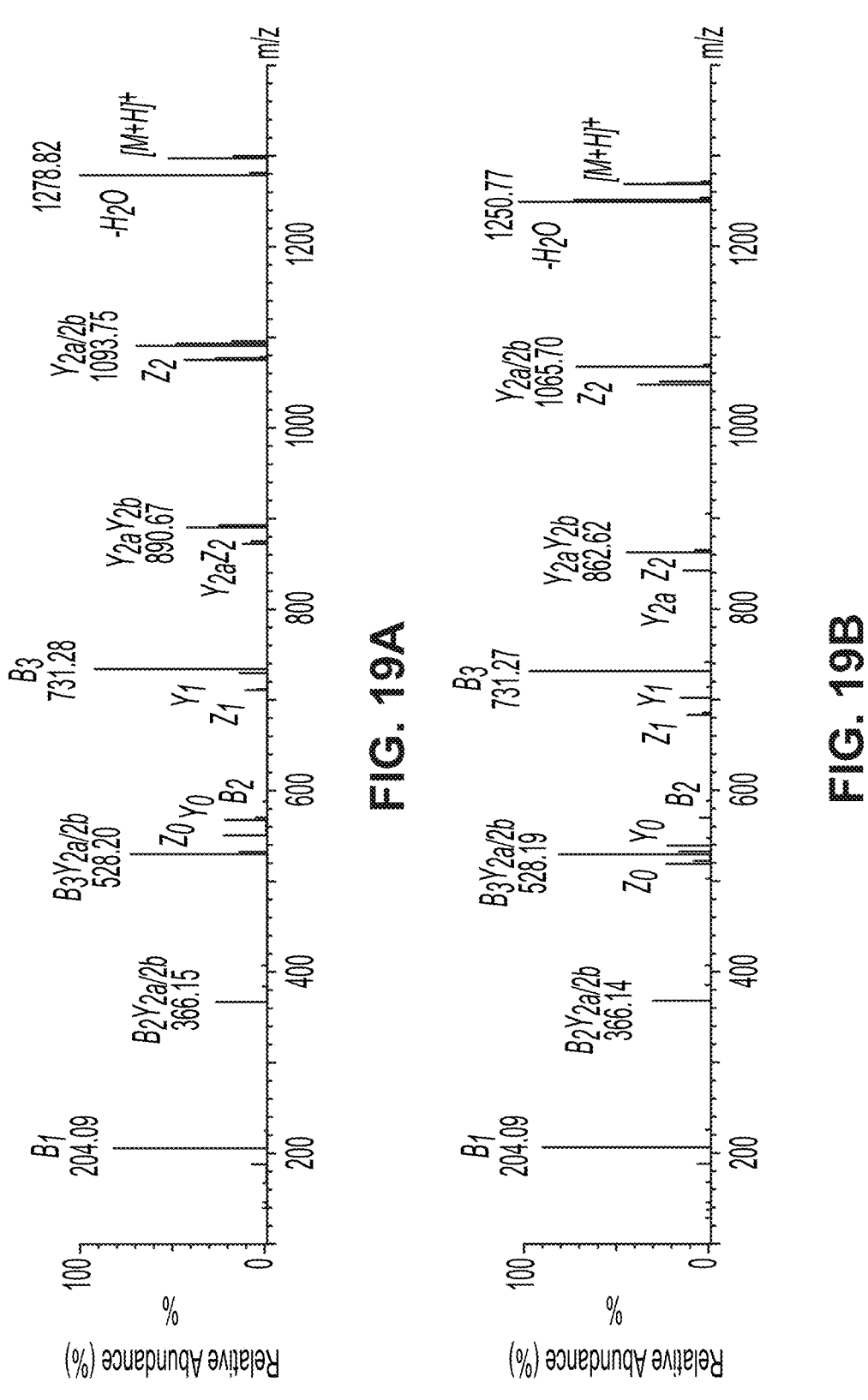

FIG. 19A shows the MS/MS spectra of GalNAc-LcGg4 (d18:1/18:0), with a collision energy of 25 eV with [M+H]+ as the parent ion.

FIG. 19B shows the MS/MS spectra of GalNAc-LcGg4 (d16:1/18:0), with a collision energy of 25 eV with [M+H]+ as the parent ion.

Figure 19C:
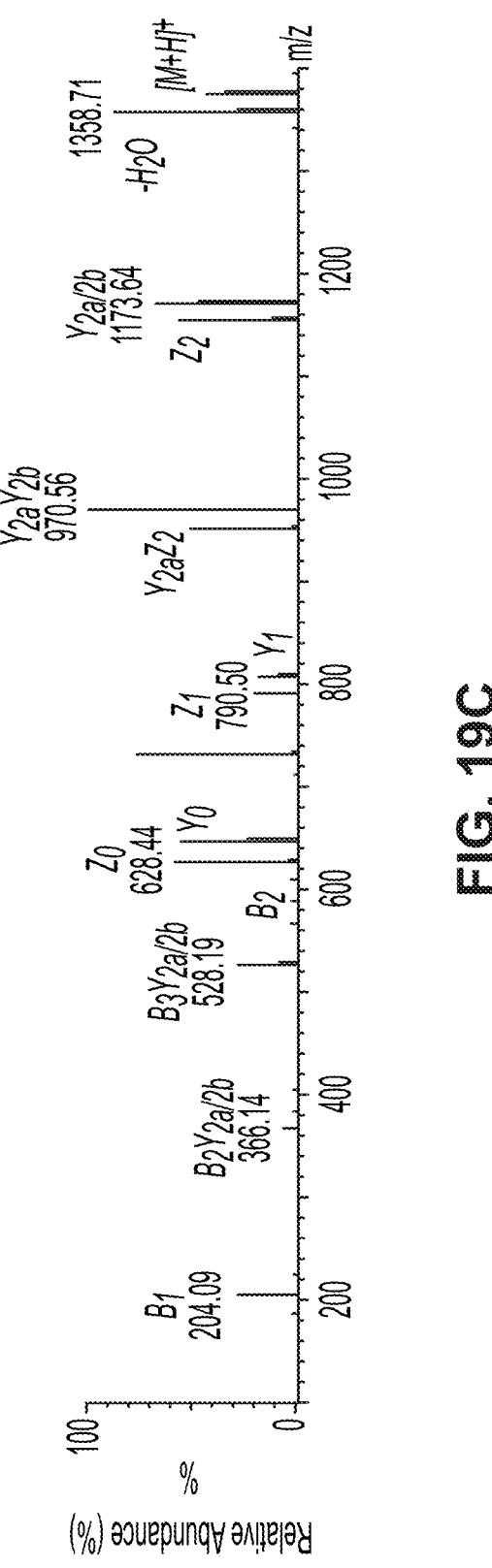

FIG. 19C shows the MS/MS spectra of GalNAc-LcGg4-NBD, with a collision energy of 25 eV with [M+H]+ as the parent ion.

Figure 19D:
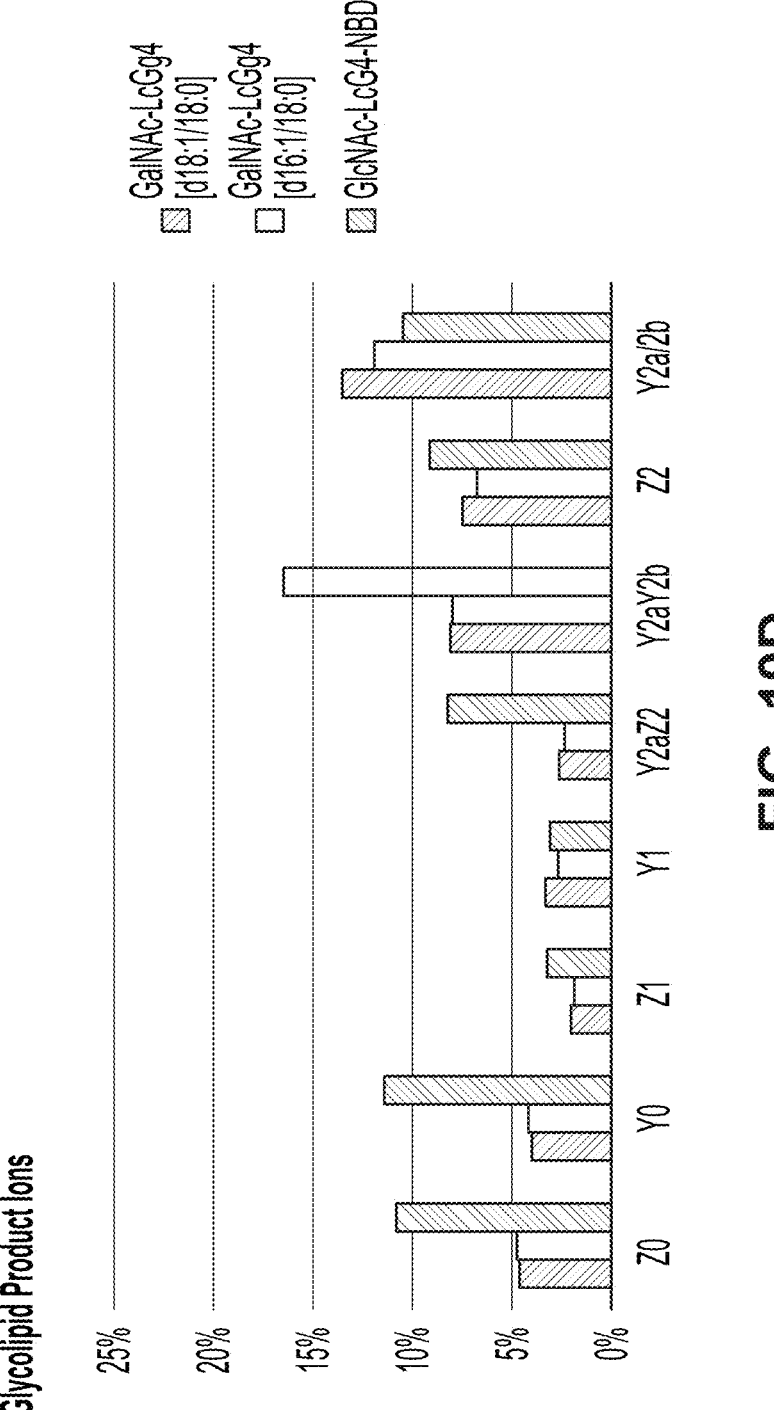

FIG. 19D shows the relative intensities of glycolipid ions Y and Z for GalNAc-LcGg4 (d18:1/18:0), GalNAc-LcGg4 (d16:1/18:0), and GalNAc-LcGg4-NBD (left, middle, right bars, respectively). The vertical axis shows the percentage of each ion or each type of ions against the combination of all identified carbohydrate and glycolipid ions.

Figure 19F:
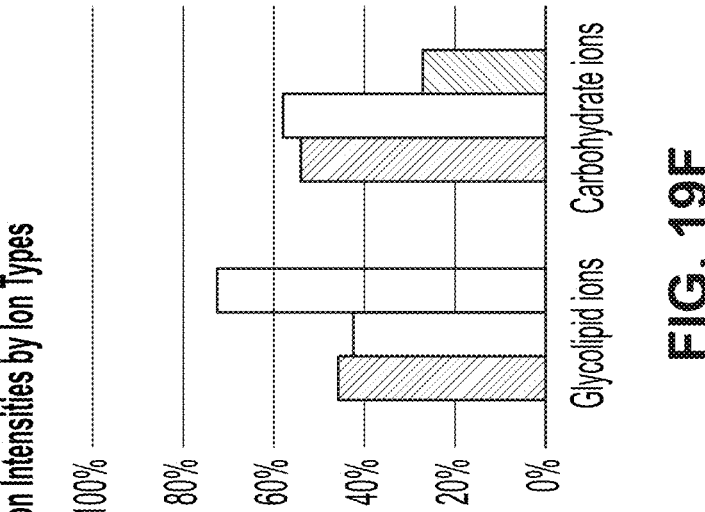
Figure 19E:
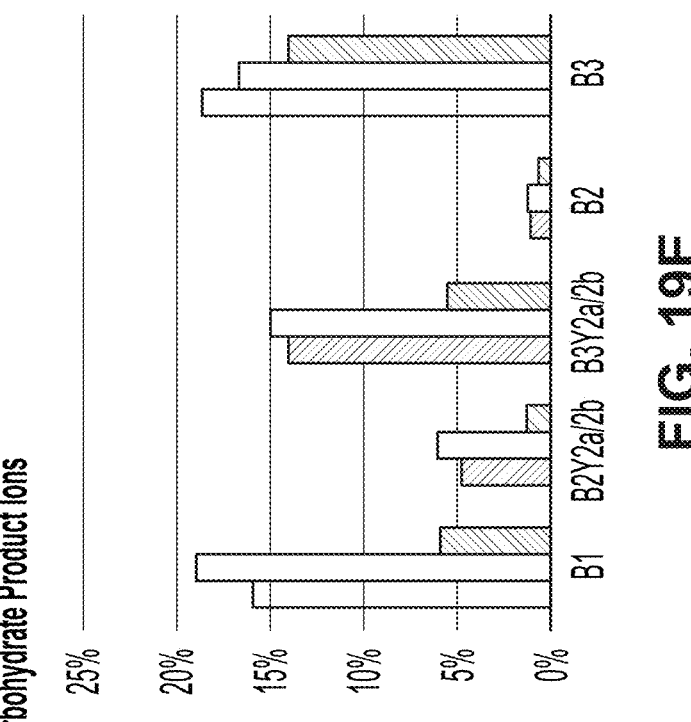

FIG. 19E shows the relative intensities of carbohydrate ions B and BY for GalNAc-LcGg4 (d18:1/18:0), GalNAc-LcGg4 (d16:1/18:0), and GalNAc-LcGg4-NBD (left, middle, right bars, respectively). The vertical axis shows the percentage of each ion or each type of ions against the combination of all identified carbohydrate and glycolipid ions.

FIG. 19F shows the relative intensities of combined carbohydrate product ions and combined glycolipid product ions for GalNAc-LcGg4 (d18:1/18:0), GalNAc-LcGg4 (d16:1/18:0), and GalNAc-LcGg4-NBD (left, middle, right bars, respectively). The vertical axis shows the percentage of each ion or each type of ions against the combination of all identified carbohydrate and glycolipid ions.

The Figures depict preferred embodiments for purposes of illustration only. Alternative embodiments of the systems and methods illustrated herein may be employed without departing from the principles of the invention described herein.

DETAILED DESCRIPTION

Figure 1:
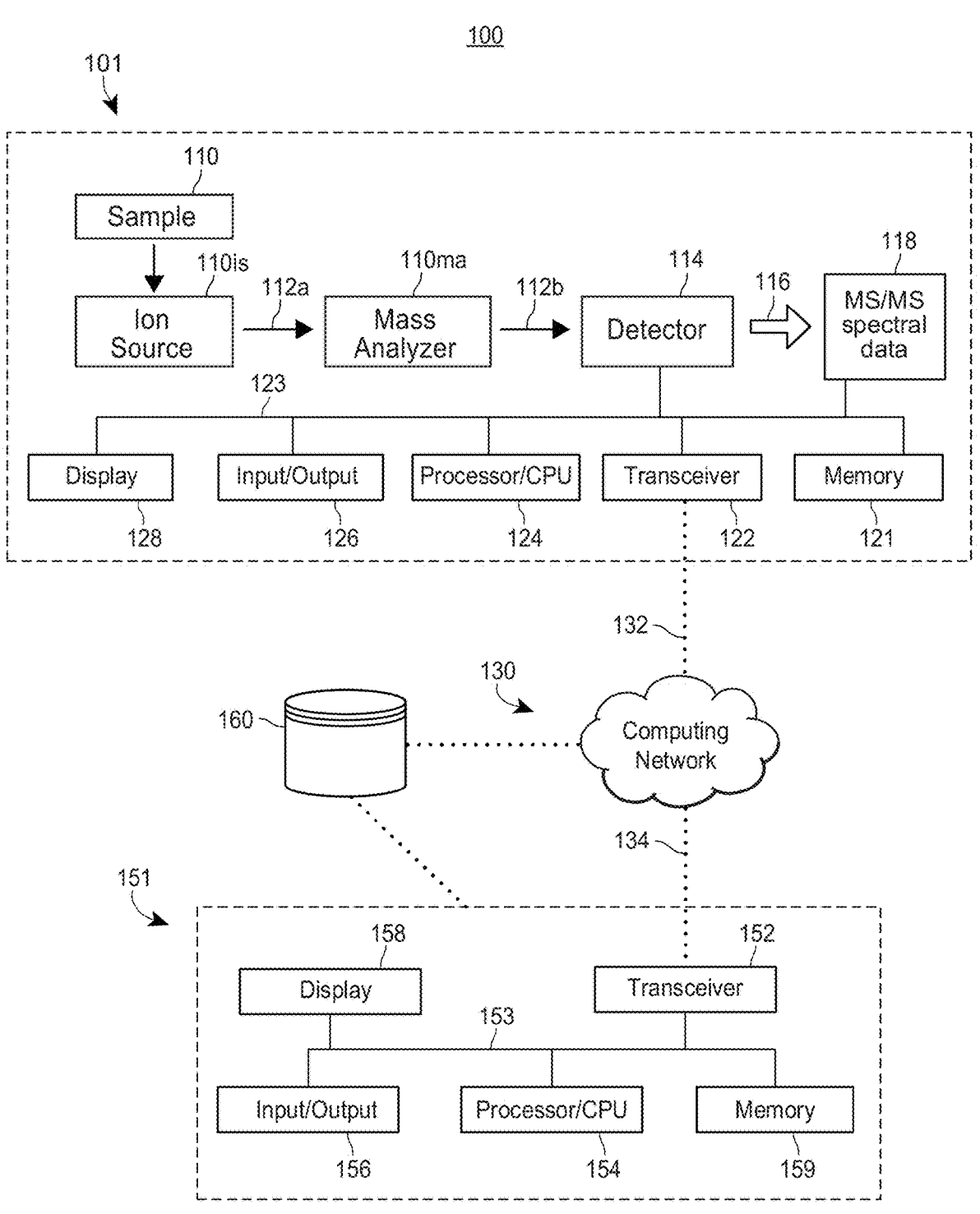
FIG. 1 illustrates an example MS based system configured to implement multi-stage MS/MS analysis for identification of experimental glycolipid samples, in accordance with various embodiments disclosed herein.

FIG. 1 illustrates an example MS based system 100 configured to implement multi-stage MS/MS analysis for identification of experimental glycolipid samples, in accordance with various embodiments disclosed herein. In various embodiments, system 100 may comprise a mass spectrometry instrument 101, which can be a mass spectrometer configured to capture product ion spectral data by MS/MS.

Mass spectrometry instrument 101 may include a sample holder operable to receive, hold, or position a glycolipid sample. Sample 110 may be configured to hold at least a portion of, a vial, sample plate, other container for encapsulating the glycolipid sample. Sample 110 may be operatively coupled to an auto-sampler, and related liquid or gas chromatographic system, configured to inject at least a portion of the sample into an ionization source 110*is*. Mass spectrometry instrumentation 101 may include an ionization source 110*is* for generating one or more precursor ions 112*a* from a sample 110. Mass spectrometry instrument 101 may include a mass analyzer 110*ma* for generating one or more product ions 112*b* from the one or more precursor ions 112*a*, where mass analyzer 110*ma* separates the one or more product ions 112*b* according to their respective mass-to-charge ratio (m/z) for detection. Detector 114 may then detect and record the relative abundance of each ion. The relative abundance and mass-to-charge ratio (m/z) may be stored as product ion MS/MS spectral data 118.

Detector 114 may be communicatively coupled via bus 123 (i.e., an electronic communications bus) to various components 121 to 128 of mass spectrometry instrument 101. For example, detector 114 may be communicatively coupled to processor 124. Processor 124 may be a microprocessor, or central processing unit (CPU) such as an INTEL®-based, AMD®-based, or other such microprocessor. Processor 124 may be responsible for the control of the various components communicatively coupled via bus 123. For example, processor 124 may control output 116 of detector 114 as MS/MS spectral data 118, which, in one embodiment, is stored in memory 121. In addition, processor 124 may receive commands or other instructions from input/output component 126. Input/output component 126 may be interfaced with, or otherwise connected to, various input/output devices, such as keyboard, mouse, or similar components. Such components may be used to access or otherwise manipulate or retrieve MS/MS spectral data 118 (e.g., in memory 121) as output 116 detector 116. Processor 124 may also be communicatively connected to display 128. Display 128 may be a display screen, where processor 124 would render a representation, such as a two-dimensional (2D), three-dimensional (3D), or other representation of MS/MS spectral data 118 on the display screen of display 128.

Processor 124 may further be communicatively connected, via bus 123, to transceiver 122. Processor 124, via transceiver 122, may be communicatively coupled over computing network 130 to computing device 151. In the displayed embodiment, computing device 151 may send 134 and receive 132 data (e.g., such as MS/MS spectral data 118) via computer network 130, via a remote processor 154 and remote transceiver 152 of computing device 151. Remote processor 154 and remote transceiver 152 may be communicatively coupled to one another via bus 153 (e.g., an electronic communications bus). Computing device 151 may further include remote memory 159, communicatively coupled via bus 153, to store data (e.g., MS/MS spectral data 118) as received via remote transceiver 152. Computing device 151 may further include display 158 and input/output component 156, communicatively coupled via bus 153, to facilitate input/output operations, e.g., such as receiving commands via touchscreens, keyboards, etc. and display data, e.g., MS/MS spectral data 118, on a screen of display

158. In this way, computing device 151 includes a remote processor 154 and a remote memory 159 that may be used to store and/or process MS/MS spectral data 118 remotely from mass spectrometry instrument 101.

In the embodiment of FIG. 1, memory 121 and/or remote memory 159 may store program instructions to cause either one or both of processors 124 and/or 154 to execute the program instructions to implement the mass spectrometry (MS) based method(s) described herein. The program instructions may be program code in a programming language such as Python, Java, C#, or other programming language. In some embodiments, the program instructions may be client-server based, where remote processor 154 communicates as a client to processor 124 as a server over computing network 130. In such embodiments, remote processor 154 may request data, such as MS/MS spectral data 118 (e.g., as stored in memory 121 or as newly output 116 by detector 114) to be transmitted from mass spectrometry instrument 101 to computing device 151. The MS/MS spectral data 118 may be requested by remote processor 154 via an online application programming interface (API) such as representational state transfer (RESTful) API, where processor 124 implements the API to receive requests from remote processor 154 and responds by providing MS/MS spectral data 118 via computer network 130. In other embodiments, mass spectrometry instrument 101 may implement a push-based interface, where newly generated and/or output 116 MS/MS spectral data 118 is transmitted via computer network 130 to computing device 151. In still further embodiments, a user of either mass spectrometer instrument 101 or computing device 151 may, via input/output 126 or 156, receive or extract MS/MS spectral data on an external storage device (not shown), such as a disk or thumb drive.

In various embodiments, processor 154 of computing device 151 is communicatively coupled to a reference spectral database 160. In some embodiments, processor 154 of computing device 151 may be communicatively coupled to reference spectral database 160 via a local connection (e.g., where reference spectral database 160 is implemented or stored on memory 159). In other embodiments, processor 154 of computing device 151 may be communicatively coupled to reference spectral database 160 either via remote connection (e.g., where reference spectral database 160 is implemented or stored in or via a cloud server an accessible via computer network 130). Generally, reference spectral database 160 stores MS/MS spectral data or values (e.g., relative intensity values and/or m/z values, such as MS/MS spectral data 118) of glycolipids. In various embodiments, reference spectral database 160 stores a plurality of reference glycolipid datasets, each dataset corresponding to a reference glycolipid and comprising at least (a) a glycan fragment dataset defining MS/MS spectra of a glycan portion of the reference glycolipid, and (b) a lipid/glycolipid fragment dataset defining MS/MS spectra of a lipid portion of the reference glycolipid.

The present disclosure provides a mass spectrometry (MS) based system configured to implement multi-stage MS, MS/MS analysis for identification of experimental glycolipid samples. The MS based system may include a mass spectrometer configured to receive and analyze an experimental glycolipid sample to determine experimental MS/MS spectral data of the experimental glycolipid sample. The MS based system may further include a reference spectral database configured to store a plurality of reference glycolipid datasets, each of the reference glycolipid datasets corresponding to a reference glycolipid and comprising at least (a) reference glycan fragment data defining MS/MS spectra of a glycan portion of the reference glycolipid, and (b) reference lipid/glycolipid fragment data defining MS/MS spectra of a lipid portion of the reference glycolipid. The MS based system may further include a memory storing program instructions. The MS based system may further include a processor communicatively coupled to the memory and the reference spectral database. In various embodiments, the processor may be configured to execute the program instructions to cause the processor to: (1) implement a first stage analysis of glycan fragment data comprising determining, from the experimental MS/MS spectral data, experimental glycan fragment data defining MS/MS spectra of a glycan portion of the experimental glycolipid sample. The first stage analysis may further include identifying a matching reference glycan of a candidate reference glycolipid selected from the reference spectral database, wherein fragment data of the matching reference glycan comprises one or more MS/MS spectral values that correspond to one or more MS/MS spectral values of the experimental glycan fragment data. The first stage analysis may further include determining, based on the matching reference glycan of the candidate reference glycolipid, a glycan structure of the glycan portion of the experimental glycolipid. The processor may further be configured to execute the program instructions to cause the processor to (2) implement a second stage analysis of lipid/glycolipid fragment data comprising determining, from the experimental MS/MS spectral data, experimental lipid/glycolipid fragment data defining MS/MS spectra of a lipid portion of the experimental glycolipid sample. The second stage analysis may further include shifting one or more mass values of the reference lipid/glycolipid fragment data of the candidate reference glycolipid to generate shifted reference lipid/glycolipid fragment data. The second stage analysis may further include performing a spectral comparison of one or more MS/MS spectral values of the shifted reference lipid/glycolipid fragment data with one or more MS/MS spectral values of the experimental lipid/glycolipid fragment data. The second stage analysis may further include determining, based on reference lipid/glycolipid fragment data of the candidate reference glycolipid, a lipid structure of the lipid portion of the experimental glycolipid. Based on the spectral comparison, the experimental glycolipid sample is determined to be of a same glycolipid species as the candidate reference glycolipid, the lipid structure of the lipid portion of the experimental glycolipid being different from a lipid structure of the candidate reference glycolipid as characterized by a difference between the experimental lipid/glycolipid fragment data and the reference lipid/glycolipid fragment data.

In some embodiments, processor (e.g., processor 154) may be communicatively coupled to a mass spectrometry instrument (MSI) (e.g., mass spectrometry instrument 101). In such embodiments, the processor may further configured to receive the MS/MS spectral data (e.g., MS/MS spectral data 118) of the experimental glycolipid sample from the mass spectrometer.

In general, ionization source 110*is* ionizes the sample. In embodiments, ionization source 110*is* can comprise electrospray ionization (ESI), desorption electrospray ionization (DESI), atmospheric pressure chemical ionization (APCI), atmospheric pressure photoionization (APPI), matrix assisted laser desorption ionization (MALDI), electron impact (EI) ionization, or chemical ionization (CI). For example, in some embodiments, ionization source 110*is* comprises ESI.

In embodiments, the MSI includes an isolation mass analyzer, an activation (or dissociation) region, and a detection mass analyzer. In embodiments, the isolation, activation (or dissociation) of the ions 112*a*, and the detection of the ions 112*b* occur in tandem in a single mass analyzer. In embodiments, the isolation of the ions 112*a* and detection of the ions 112*b* occur in tandem in a single mass analyzer with ion activation occurring in a collision cell (not shown) outside either mass analyzer. In embodiments, the isolation of the ions 112*a* and detection of the ions 112*b* occur in tandem in two separate mass analyzers with ion activation occurring in a collision cell (not shown) outside either mass analyzer (such that precursor ions 112*a* are first transferred to the collision cell from the mass analyzer and resulting fragment ions 112*b* are then transferred to the mass analyzer from the collision cell). The MSI may be a MSI including two mass analyzers or a MSI including a mass analyzer (e.g., mass analyzer 110*ma*) capable of performing tandem MS experiments. In embodiments, the MSI includes a mass analyzer (e.g., mass analyzer 110*ma*) capable of performing tandem MS experiments. In embodiments, the MSI includes two mass analyzers (e.g., two of mass analyzers 110*ma*) capable of performing tandem MS experiments. The mass analyzer (e.g., mass analyzer 110*ma*) can comprise a quadrupole, time-of-flight (TOF), orbitrap, Fourier-transform ion cyclotron resonance (FT-ICR) cell, quadrupole/linear ion trap (QIT/LIT) or a combination thereof. In embodiments, the MSI comprises a hybrid instrument comprising a quadrupole, TOF, and a collision cell (not shown). In embodiments, activation is performed in a collision cell (not shown) located between a quadrupole and a TOF.

In general, the ions 112*a* can be activated using any activation means known in the art. In embodiments, the activation means is a low energy activation means. In embodiments, activation of the ions 112*a* comprises collision-induced dissociation (CID), higher energy collisional dissociation (HCD), infrared multiple photon dissociation (IRMPD), electron transfer dissociation (ETD), electron capture dissociation (ECD), ultraviolet photodissociation (UVPD), or a combination thereof. In embodiments, activation of the ions 112*a* comprises CID, HCD, IRMPD, or a combination thereof. In embodiments, activation of the ions 112*a* comprises CID. In embodiments, activation of the ions 112*a* comprises ETD, ECD, UVPD, or a combination thereof.

Processor 124 or 154 may be configured to execute program instructions to cause the processor to implement a first stage analysis of glycan fragment data and a second stage analysis of lipid/glycolipid fragment data. In embodiments, the processor implements the first stage analysis and then the second stage analysis. In embodiments, the processor implements the second stage analysis and then the first stage analysis. In embodiments, the processor implements the first and second stage analyses in tandem.

The present disclosure further provides a mass spectrometry (MS) based method of implementing multi-stage MS/MS analysis for identification of experimental glycolipid samples. The MS based method includes (1) implementing, by a processor communicatively coupled to a memory and a reference spectral database, a first stage analysis of glycan fragment data comprising: determining, from experimental MS/MS spectral data of an experimental glycolipid sample as analyzed by a mass spectrometer, experimental glycan fragment data defining MS/MS spectra of a glycan portion of the experimental glycolipid sample, identifying a matching reference glycan of a candidate reference glycolipid selected from the reference spectral database. The spectral database may store a plurality of reference glycolipid datasets, each of the reference glycolipid datasets corresponding to a reference glycolipid and comprising at least (a) reference glycan fragment data defining MS/MS spectra of a glycan portion of the reference glycolipid, and (b) reference lipid/glycolipid fragment data defining MS/MS spectra of a lipid portion of the reference glycolipid, and wherein fragment data of the matching reference glycan comprises one or more MS/MS spectral values that correspond to one or more MS/MS spectral values of the experimental glycan fragment data, and determining, based on the matching reference glycan of the candidate reference glycolipid, a glycan structure of the glycan portion of the experimental glycolipid. The MS based method may further include (2) implementing, by the processor, a second stage analysis of lipid/glycolipid fragment data comprising: determining, from the experimental MS/MS spectral data, experimental lipid/glycolipid fragment data defining MS/MS spectra of a lipid portion of the experimental glycolipid sample, shifting one or more mass values of the reference lipid/glycolipid fragment data of the candidate reference glycolipid to generate shifted reference lipid/glycolipid fragment data, performing a spectral comparison of one or more MS/MS spectral values of the shifted reference lipid/glycolipid fragment data with one or more MS/MS spectral values of the experimental lipid fragment data, and determining, based on reference lipid/glycolipid fragment data of the candidate reference glycolipid, a lipid structure of the lipid portion of the experimental glycolipid. Based on the spectral comparison, the experimental glycolipid sample may be determined to be of a same glycolipid species as the candidate reference glycolipid, the lipid structure of the lipid portion of the experimental glycolipid being different from a lipid structure of the candidate reference glycolipid as characterized by a difference between the experimental lipid/glycolipid fragment data and the reference lipid/glycolipid fragment data.

Glycan fragment data and lipid/glycolipid fragment data can be distinguished from each other depending on whether the charge resides on the non-reducing end (glycan) or on the reducing end (lipid). The inventors advantageously found that for a given glycan species, the glycan fragment data will be the substantially the same in terms of m/z and relative intensity, regardless of the lipid form of the glycolipid, e.g., the glycan will fragment in the same way, having the same m/z and same relative intensities, even when conjugated to different lipids. As described in the specific embodiments below, the experimental MS/MS spectral data defining the MS/MS spectra of the glycan portion of various glycolipids including the glycan species ganglioside D3 (GD3) was the same when the glycolipid analyzed was GD3 (39:1), GD3 (40:1), or GD3 (41:1). As used herein, and unless specified otherwise, the lipid chains are identified with standard lipid nomenclature, using (X:Y) to indicate the number of carbons in the lipid (number X before the colon) and the number of carbon-carbon double bonds in the lipid (number Y after the colon). Thus, a glycolipid identified as GD3 (39:1) refers to a glycolipid having a GD3 glycan and a lipid having 39 carbon atoms and 1 carbon-carbon double bond.

The systems and methods of the disclosure provide a multi-stage MS/MS analysis for the identification of experimental glycolipid samples.

The first stage analysis comprises determining, from the experimental MS/MS spectral data, experimental glycan fragment data defining MS/MS spectra of a glycan portion of the experimental glycolipid sample, identifying a matching reference glycan of a candidate reference glycolipid selected from the reference spectral database, wherein fragment data of the matching reference glycan comprises one or more MS/MS spectral values that correspond to one or more MS/MS spectral values of the experimental glycan fragment data, determining, based on the matching reference glycan of the candidate reference glycolipid, a glycan structure of the glycan portion of the experimental glycolipid.

The determination of the experimental glycan fragment data defining MS/MS spectra of a glycan portion of the experimental glycan fragment data can include identifying the fragment data where the charge resides on the non-reducing end of the fragment. The identifying a matching reference glycan of a candidate reference glycolipid selected from the reference spectral database can include comparing the identified experimental glycan fragment data with one or more candidate reference glycolipids from the reference spectral database and determining a match when the candidate reference glycolipid includes one or more MS/MS spectral values that corresponds to one or more MS/MS spectral values of the experimental glycan fragment data. The experimental glycan fragment data can be compared with as many candidate references as needed until a match is found. In embodiments, a match is present when one or more of the high relative intensity MS/MS spectral values of the experimental fragment data is found in the candidate reference spectra, if one or more of the intensities of the MS/MS spectral values of the experimental fragment data match or nearly match the intensities of the MS/MS spectral values of the candidate reference spectra, or both. In embodiments, a match is present when more than half of the high relative intensity MS/MS spectral values of the experimental fragment data is found in the candidate reference spectra, if more than half of the intensities of the MS/MS spectral values of the experimental fragment data match or nearly match the intensities of the MS/MS spectral values of the candidate reference spectra, or both.

Figure 2:
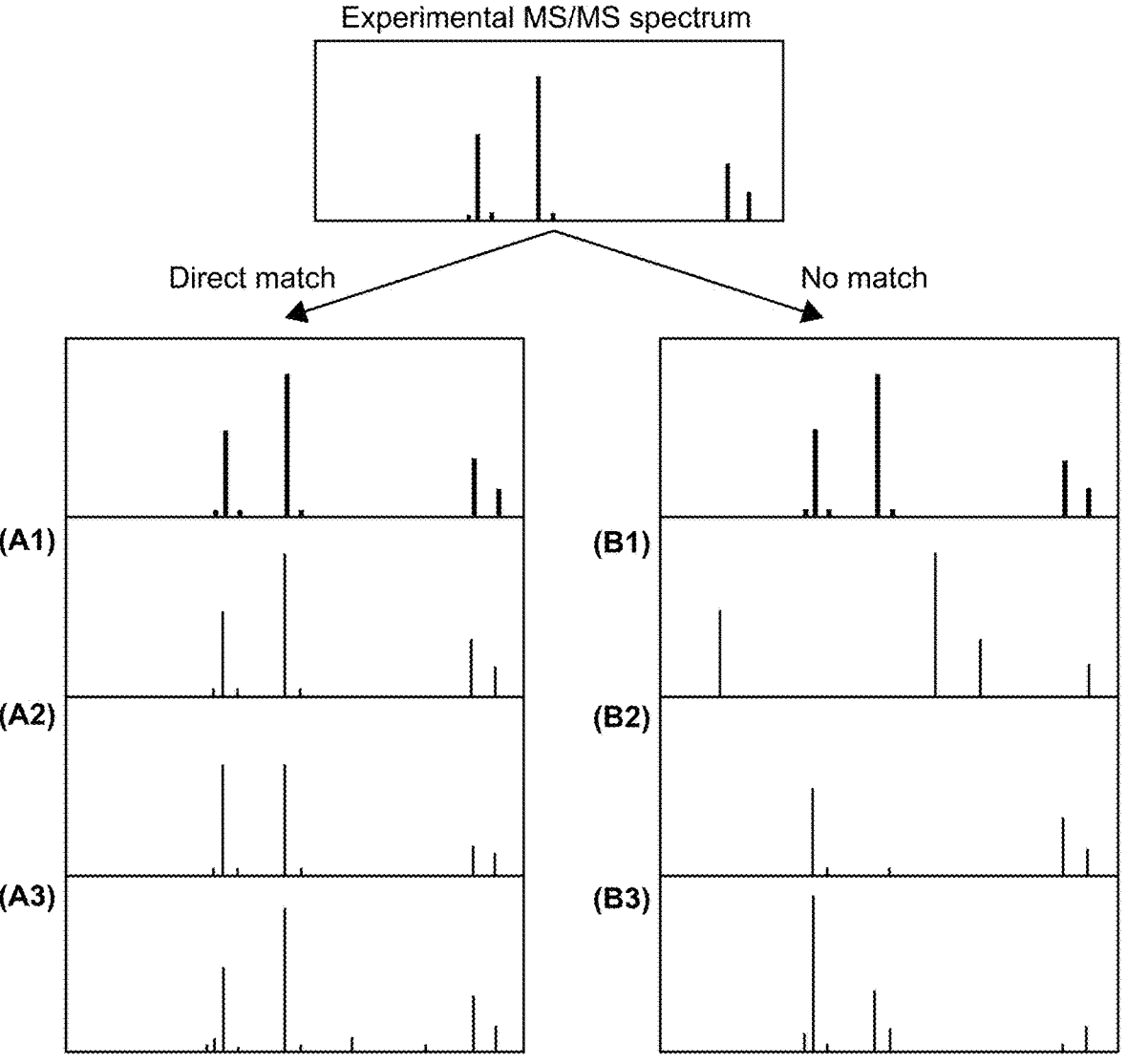
FIG. 2 illustrates results of typical one-stage MS/MS database searches resulting in spectral matches and resulting in no match.

FIG. 2 illustrates example results of a typical database search for an experimental MS/MS spectra. In the optimal case, the experimental MS/MS spectrum matches exactly with the spectrum in the database (FIG. 2 (A1)), in both the location (i.e., mass to charge ratio, m/z) and the relative intensities of the product ion(s). A high matching score can also be assigned if the relative intensities of fragments nearly match (FIG. 2 (A2)) or if most of the fragments are observed (FIG. 2 (A3)). Otherwise, a low identification score (no match) is given, e.g., if no fragments match (FIG. 2 (B1)), multiple high relative intensity fragments are missing (FIG. 2 (B2)), or the relative intensities are greatly dissimilar (FIG. 2 (B3)).

Figures 3A, 3B, 3C:
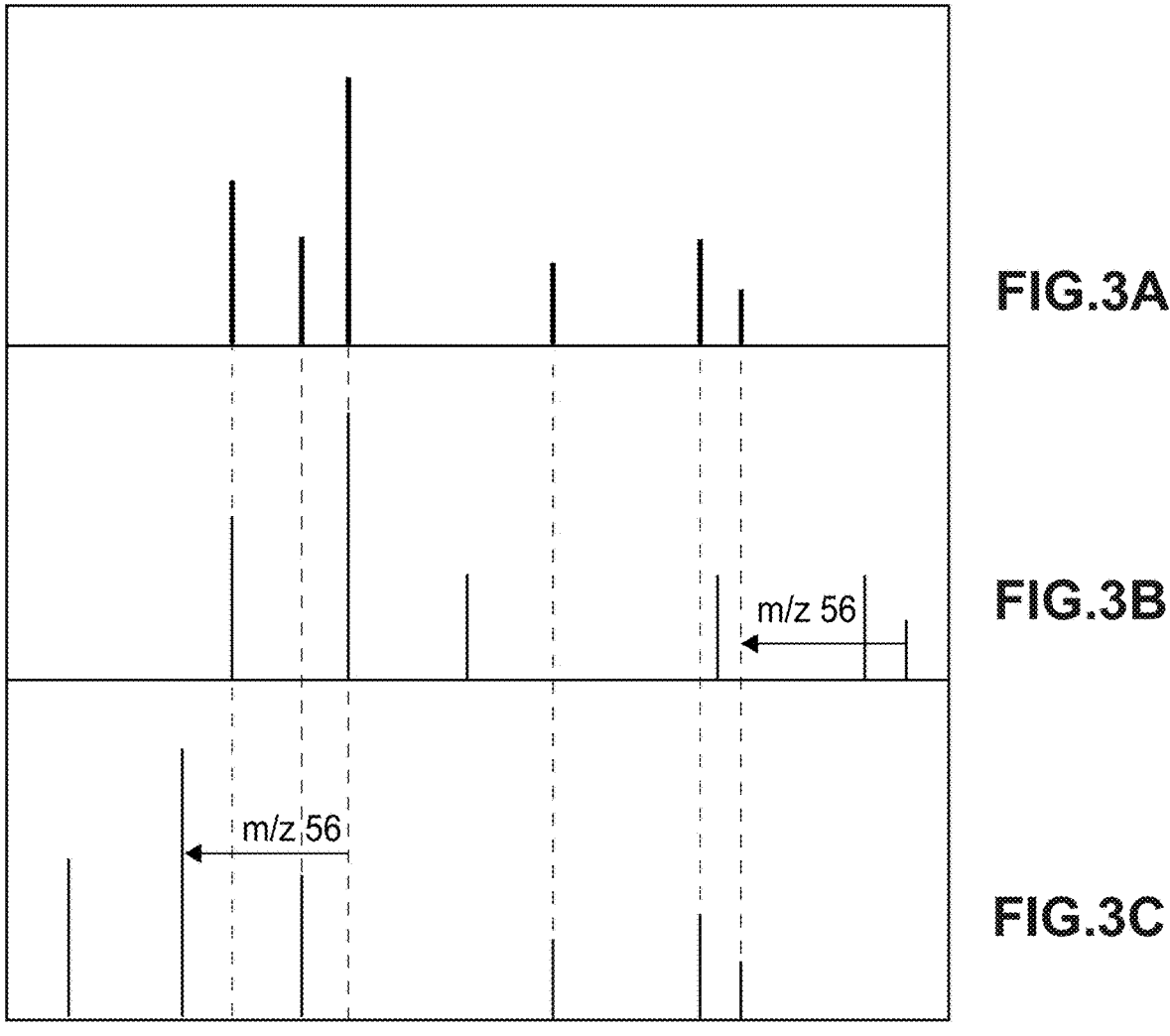
FIG. 3A illustrates an experimental glycolipid MS/MS spectrum.
FIG. 3B illustrates a reference glycolipid MS/MS spectrum physically present in a library.
FIG. 3C illustrates a projected MS/MS spectrum using prior art rule-based methodology, resulting in matching of lipid peaks but mismatching of glycan peaks.

FIG. 3 illustrates the result of glycolipid spectral matching using conventional lipid rule-based methods. FIG. 3A provides an example of an experimental glycolipid MS/MS spectrum. A reference glycolipid MS/MS spectrum physically present in a database is shown in FIG. 3B. It can be seen that there is a partial match (2 fragments) between the experimental glycolipid MS/MS spectrum and the reference glycolipid MS/MS spectrum, and the remaining fragments would align if the reference glycolipid MS/MS spectrum were shifted by an m/z value of 56. As shown in FIG. 3C, using the conventional rule-based methodology, uniform shifting of the reference spectrum by a lipid mass to match the ions in the experimental spectrum (FIG. 3A) moves ALL ions to give the rule-based spectrum (FIG. 3C). When the rule-based spectrum is compared to the experimental spectrum, only a partial match (4 fragments) would be observed between the rule-based spectrum and the experimental glycolipid spectrum, to ultimately generate a low matching score and the experimental glycolipid would go unidentified.

Figures 4A, 4B, 4C:
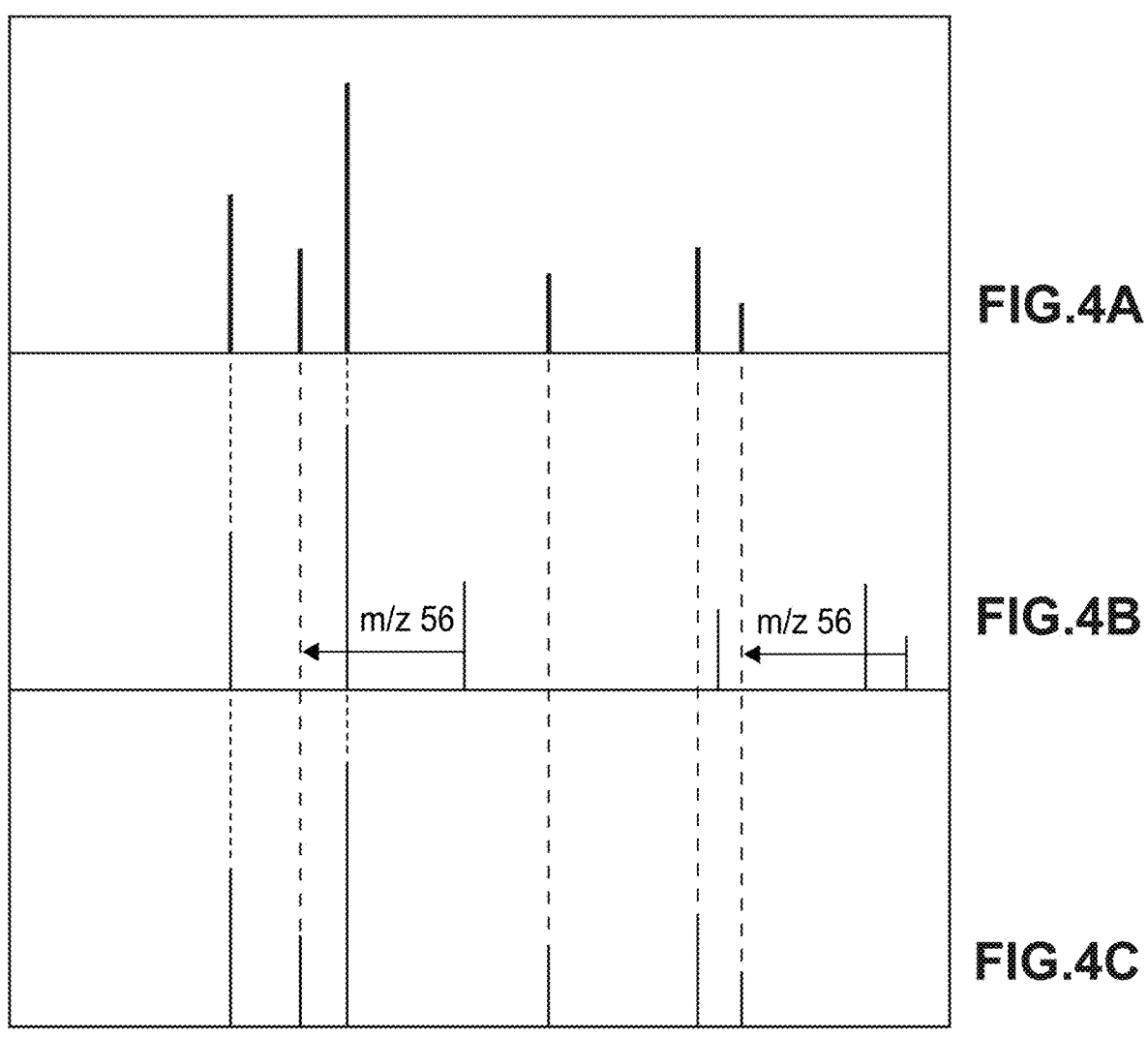
FIG. 4A illustrates an experimental glycolipid MS/MS spectrum.
FIG. 4B illustrates a reference glycolipid MS/MS spectrum physically present in a library.
FIG. 4C illustrates a projected glycolipid MS/MS spectrum after second-stage rule-based shifting of only the fragments containing the lipid moiety, in accordance with various embodiments disclosed herein.

FIG. 4 illustrates an embodiment of the disclosure herein. FIG. 4A illustrates an experimental glycolipid sample that is the same as in FIG. 3A. FIG. 4B illustrates a matching reference glycan of a candidate reference glycolipid, wherein the fragment data of the matching reference glycan comprises one or more MS/MS spectral values that correspond to one or more MS/MS spectral values of the experimental glycan fragment, thereby identifying a glycan structure of the glycan portion of the experimental glycolipid. FIG. 4C illustrates a projected glycolipid MS/MS spectrum after rule-based shifting of one or more mass values of the candidate reference lipid/glycolipid fragment data to generate shifted reference lipid/glycolipid fragment data that defines MS/MS spectra of the lipid portion of the reference glycolipid sample, in accordance with various embodiments disclosed herein. The projected glycolipid MS/MS spectrum identifies a lipid structure of the lipid portion of the experimental glycolipid characterized by a difference between the experimental lipid/glycolipid fragment data, and the reference lipid/glycolipid fragment data.

FIG. 4 illustrates the result of analyzing the glycolipid spectrum using the two-stage method with various embodiments disclosed herein. The first stage analysis of glycan fragment data (FIG. 4B) comprises determining, based on the matching reference glycan of the candidate reference glycolipid, a glycan structure of the glycan portion of the experimental glycolipid is the natural result of the identification of a matching reference glycan of a candidate reference glycolipid because, as described herein, the glycan fragment data for a glycan portion of a glycolipid is an intrinsic feature of the glycan. In embodiments, the glycan structure can be identified by outputting to a screen of a display or printed out on a printer. In embodiments, the glycan structure can be identified as the name of the glycan, a picture of the structure, or both.

The second stage analysis of lipid/glycolipid fragment data (FIG. 4C) comprises determining, from the experimental MS/MS spectral data, experimental lipid/glycolipid fragment data defining MS/MS spectra of a lipid portion of the experimental glycolipid sample, shifting one or more mass values of the reference lipid/glycolipid fragment data of the candidate reference glycolipid to generate shifted reference lipid/glycolipid fragment data, performing a spectral comparison of one or more MS/MS spectral values of the shifted reference lipid/glycolipid fragment data with one or more MS/MS spectral values of the experimental lipid/glycolipid fragment data, and determining, based on reference lipid/glycolipid fragment data of the candidate reference glycolipid, a lipid structure of the lipid portion of the experimental glycolipid. Based on the spectral comparison, the experimental glycolipid sample may be determined to be of a same glycolipid species as the candidate reference glycolipid, the lipid structure of the lipid portion of the experimental glycolipid being different from a lipid structure of the candidate reference glycolipid as characterized by a difference between the experimental lipid/glycolipid fragment data and the reference lipid/glycolipid fragment data.

The determination of the experimental lipid/glycolipid fragment data defining MS/MS spectra of a lipid portion of the experimental glycan fragment data can include identifying the fragment data where the charge resides on the reducing end of the fragment.

The shifting of the one or more mass values of the reference lipid/glycolipid fragment data to generate shifted reference lipid/glycolipid fragment data that defines MS/MS spectra of the lipid portion of the reference glycolipid sample can be by a known value. In embodiments, the shifting of the one or more mass values of the reference lipid/glycolipid fragment data to generate shifted reference lipid/glycolipid fragment data that defines MS/MS spectra of the lipid portion of the reference glycolipid can be by an m/z value of $\pm 14n$, $\pm 2n'$, or a combination of both, wherein n and n' are integers. Each 14n represents a $CH_2$ group in the lipid chain and each 2n' represents a carbon-carbon double bond in the lipid chain. Thus, for example, if the reference lipid/glycolipid fragment data is shifted by an m/z value that is a positive multiple of 14, then the shifted reference fragment data has a longer lipid chain than the reference lipid/glycolipid fragment data, if the reference lipid/glycolipid fragment data is shifted by an m/z value that is a negative multiple of 2, then the shifted reference fragment data has a lipid chain with more carbon-carbon double bonds than the reference lipid/glycolipid fragment data, and if the reference lipid/glycolipid fragment data is shifted by an m/z value that is a positive multiple of 14 and a positive multiple of 2, then the shifted reference fragment data has a longer lipid chain and fewer carbon-carbon bonds than the reference lipid/glycolipid fragment data.

Although the description herein refers to shifting of the reference lipid/glycolipid fragment of the candidate reference glycolipid, one of ordinary skill in the art will readily recognize that the mass values of the experimental lipid/glycolipid fragment can also be shifted. For example, if a matching reference glycan of a candidate reference glycolipid has been identified from the reference spectral database, the one or more mass values of the experimental lipid/glycolipid fragment data can be shifted to match the lipid/glycolipid fragment data of the candidate reference glycolipid or one or more mass values of the lipid/glycolipid fragment data of the candidate reference glycolipid can be shifted to match the experimental lipid/glycolipid fragment data. In either case, the absolute value of the shift will be the same; however, the sign of the shift (positive or negative) will depend on which lipid/glycolipid fragment data is shifted.

Advantageously, only one or more mass values of the reference lipid/glycolipid fragment data are shifted. In such embodiments, the experimental glycan fragment data may not be shifted, so as to maintain the original m/z values. Unlike conventional spectral matching using lipid rule-based methods (FIG. 3), where all fragments are shifted, the systems and methods of the disclosure allows shifting of only the lipid/glycolipid fragments, thereby allowing identification of new, unknown, glycolipids that are not already present in a library or database.

Performing a spectral comparison of one or more MS/MS spectral values of the shifted reference lipid/glycolipid fragment data of the candidate reference glycolipid with one or more MS/MS spectral values of experimental lipid/glycolipid fragment data, can include comparing MS/MS spectral values of the reference lipid/glycolipid fragment data of the candidate reference glycolipid identified in the first stage analysis. The spectral comparison can include determining if the one or more MS/MS spectral values of the shifted reference lipid/glycolipid fragment data have suitable m/z values and intensities to match with the experimental glycolipid.

Determining, based on the matching reference lipid/glycolipid fragment data of the candidate reference glycolipid, a lipid structure of the lipid portion of the experimental glycolipid includes identifying the structure of the matching reference lipid/glycolipid fragment data of the candidate reference glycolipid and adjusting the lipid structure to include account for the shift of the lipid/glycolipid fragment data of the reference glycolipid. In embodiments, the lipid structure can be identified by outputting to a screen of a display or printed out on a printer. In embodiments, the lipid structure can be identified with standard lipid nomenclature, a picture of the structure, or both.

Thus, the systems and methods of the disclosure can, based on the spectral comparison, determine the experimental glycolipid sample to be of a same glycolipid species as the candidate reference glycolipid, where the lipid structure of the lipid portion of the experimental glycolipid being different from a lipid structure of the candidate reference glycolipid as characterized by a difference between the experimental lipid/glycolipid fragment data and the reference lipid/glycolipid fragment data.

In FIG. 4C, the difference between the experimental lipid/glycolipid fragment data and reference lipid/glycolipid fragment data is 56 m/z, or 14n when n is 4. Thus, the difference between the lipid structure of the experimental lipid and the structure of the shifted lipid is 4 $CH_2$ units.

In general, the experimental glycolipid sample can be any experimental glycolipid sample. In embodiments, the experimental glycolipid sample is an unidentified glycolipid sample. In embodiments, the experimental glycolipid sample is a natural glycolipid. In embodiments, the experimental glycolipid sample is a natural glycolipid sample comprising a human or animal bodily fluid or tissue based glycolipid sample. In embodiments, the experimental glycolipid sample is a synthetic glycolipid sample. In embodiments, the experimental glycolipid sample is a natural or synthetic glycolipid having a modified glycan. In such embodiments, the experimental glycan fragment data of the glycolipid sample having a modified glycan can match with the glycan fragment data of a candidate reference spectrum of a glycolipid having the same modification. In embodiments, the experimental glycolipid sample is a natural or synthetic glycolipid having a modified lipid. In embodiments, the experimental glycolipid sample is a natural or synthetic glycolipid having a modified glycan and a modified lipid. In embodiments, the experimental glycolipid sample includes one or more unidentified glycolipids as one or more corresponding biomarkers. In refinements of the foregoing embodiment, the one or more biomarkers comprise biomarkers for cancer, Alzheimer's disease, depression, or a combination thereof.

In embodiments, the one or more MS/MS spectral values of the matching reference glycan fragment data correspond to one or more MS/MS spectral values of the experimental glycan fragment data by at least a glycan based intensity threshold value. As used herein, and unless specified otherwise, a "glycan based intensity threshold value" refers to a minimum relative intensity value, above which the relative intensities of the matching reference glycan fragment data and the experimental glycan fragment data are considered to match. The glycan based intensity threshold value can be about 50% for a low matching score or, for a high matching score, at least about 70%, i.e., if the less intense of the matching reference glycan fragment data and the experimental glycan fragment data is at least 70% of the other of the experimental glycan fragment data and the matching reference glycan fragment data, the two are considered a match. In embodiments, the glycan based intensity threshold value can be about 70%, about 75%, about 80%, about 85%, about 90%, about 92%, about 95%, or about 98%. It will be understood that the intensities of the experimental glycan fragment data and the matching reference glycan fragment data may not be an exact match due to instrumental (e.g., QTOF vs Orbitrap vs LIT), experimental (e.g., LC-MS mobile phases and gradients), and sample differences (e.g., sample preparations, extractions, and salt concentrations). The relative intensities of the experimental glycan fragment data and the matching reference glycan fragment data can be determined by numerical relative intensity comparison and/or overlay comparison.

In embodiments, the one or more MS/MS spectral values of the matching reference lipid/glycolipid fragment data corresponds to one of more MS/MS spectral values of the experimental lipid/glycolipid fragment data or the shifted reference lipid/glycolipid fragment data by at least a lipid based intensity threshold value. As used herein, and unless specified otherwise, a "lipid based intensity threshold value" refers to a minimum relative intensity value, above which the relative intensities of the experimental lipid/glycolipid fragment data and the (shifted) reference lipid/glycolipid fragment data are considered to match. The lipid based intensity threshold value can be about 50% for a low matching score or, for a high matching score, at least about 70%, i.e., if the less intense of the experimental lipid/glycolipid fragment data and the (shifted) reference lipid/glycolipid fragment data is at least 70% of the other of the (shifted) reference lipid/glycolipid fragment data and the experimental lipid/glycolipid fragment data, the two are considered a match. In embodiments, the lipid based intensity threshold value can be about 70%, about 75%, about 80%, about 85%, about 90%, about 92%, about 95%, or about 98%. It will be understood that the intensities of the experimental lipid/glycolipid fragment data and the matching reference lipid/glycolipid fragment data may not be an exact match due to, instrumental, experimental, and sample differences. The relative intensities of the experimental lipid/glycolipid fragment data and the matching reference lipid/glycolipid fragment data can be determined by numerical relative intensity comparison and/or overlay comparison.

In various embodiments, the one or more MS/MS spectral values of the experimental lipid/glycolipid fragment data may correspond to one or more MS/MS spectral values of the reference lipid/glycolipid fragment data or the shifted reference lipid/glycolipid fragment data by at least a lipid based intensity threshold value.

The systems and methods of the disclosure can further comprise generating a matching score for the experimental glycolipid sample based on a comparison of MS/MS spectra of (1) the reference glycan fragment data and either the shifted reference lipid/glycolipid fragment data or the reference lipid/glycolipid fragment data, with (2) the experimental glycan fragment data and the experimental lipid/glycolipid fragment data.

The systems and method of the disclosure can further comprise updating the reference spectral database with a new glycolipid dataset corresponding to the experimental glycolipid sample, the new glycolipid dataset stored in the reference spectra database, and the new glycolipid dataset comprising at least (a) the experimental glycan fragment data, and (b) the experimental lipid/glycolipid fragment data.

Specific Embodiments

The following embodiments are for illustrative purposes only and should not be considered limiting to the disclosure in any way.

MS fragmentation of glycolipids can occur on both the lipid and the glycan moieties to result in complex product spectra. Glycolipid fragments are represented by capitalized letters: A, B, C, X, Y, and Z. A, B, and C fragments designate cleavages where the charge resides on the non-reducing end. X, Y, and Z fragments designates cleavages where the charge resides on the reducing end. Subscript numbers indicate the number of sugar residues in the fragment. For example, a $B_1$ fragment would contain a single sugar residue, while a $B_3$ fragment would contain three sugar residues. Y and Z fragments are named similarly, but their numbering appears differently. While B and C fragments begin their numbering at 1, Y and Z numbering begins at 0. The $Y_0/Z_0$ fragments result from cleavage of the glycosidic bond between the glycan and lipid parts of the molecule, resulting in 0 sugar residues in the fragment.

Although MS fragmentation of glycolipids can be very complex, the main focus here are the B/C and Y/Z fragments, instead of A/X fragments. A and X ions are formed via cross-ring cleavages, whereas B, C, Y, and Z ions are formed from glycoside bond cleavage. As such, A and X ions are typically observed during high-energy activation events (e.g., UVPD, ETD/ECD, etc.) because 2 $\sigma$ bonds (including at least 1 C—C bond) must be broken for these fragmentations to occur. Conversely, the glycoside cleavages (form B/C and Y/Z ions) are more abundant during low-energy activation, such as from collision induced dissociation (CID). Therefore, these experimental MS/MS spectra were only searched for these fragments, not cross-ring cleavages.

The challenge with identifying glycolipids through the existing rule-based method is that they give rise to two different types of fragments, one type containing only the glycan (e.g., B, C, and internal fragments) regardless of the lipid form and the other type also containing the lipid, which follow the patterns predictable by rule-based methods. By shifting all fragment ions uniformly, the information inherent to the reference glycan is lost and only partial spectral matches can be made.

To address this issue, a new searching methodology where the glycan and lipid/glycolipid fragments of glycolipid MS/MS spectra are characterized independently is disclosed. Accordingly, fragments from each reference spectrum are divided into two types: (1) those containing only the glycan (i.e., A, B, C, and internal glycan fragments), and (2) those containing also the lipid (i.e., X, Y, Z, and neutral loss fragments). The fragments containing only the glycan can be referred to as the "glycan fragment," "carbohydrate fragment," "carbohydrate product ion(s)," "glycan product ion(s)," "glycan ion" and/or "carbohydrate ion." The fragments containing lipid can be referred to as the "lipid fragment," "glycolipid fragment," "glycolipid product ion (s)," "lipid product ion(s)," "lipid ion," and/or "glycolipid ion." The new methodology uses a two-stage searching process. First, a search is performed to identify the fragments matching those containing only the glycan, thereby providing the glycolipid class match (e.g., GM4, GD2, etc.) and glycan identity. Once the glycolipid class matches, the second set of fragments, containing the lipid chain, are shifted by a predictable lipid mass to yield the lipid identity, in much the same way as other rule-based methods. However, in our case, only select fragments are shifted, while other fragments (the first set of fragments) are not manipulated. The resultant spectrum, as shown FIG. 4C, would match the experimental spectrum to give a high matching score. The precursor match after an m/z 56 mass shift shown in FIG. 4 indicates that the experimental lipid is $4\times CH_2$ lighter than the reference glycolipid.

Figure 5:
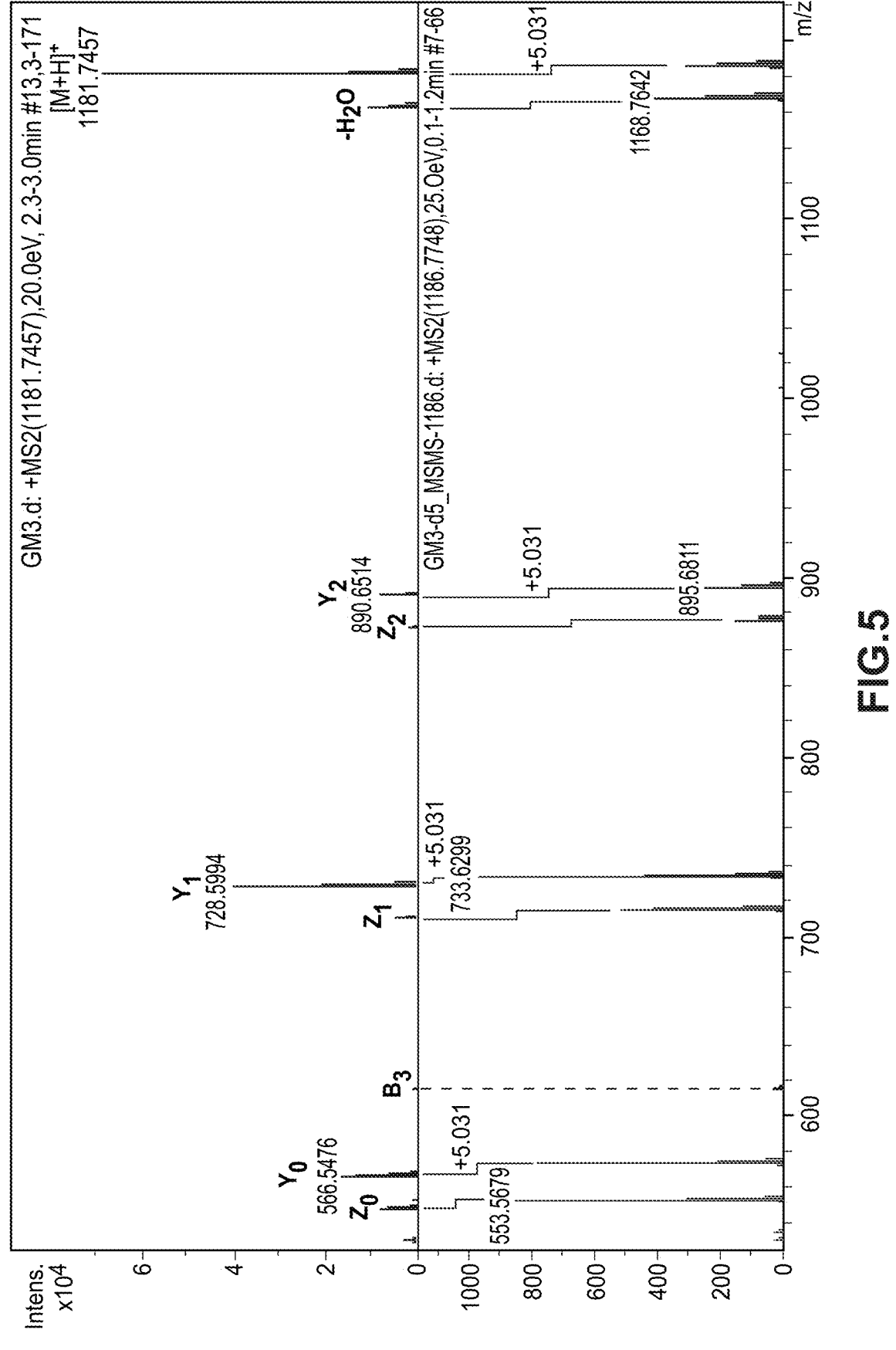
FIG. 5 illustrates a comparison of the MS/MS spectra of GM3 (top) and GM3-d5 (bottom).

A first example is the MS/MS spectra of a commercial and a synthetic, isotope-labeled monosialodihexosylganglioside (GM3) samples. GM3 is a simple glycolipid with a linear trisaccharide and a 36:1 ceramide moiety of two lipid chains (18:0 and 18:1). The synthetic, isotope-labeled GM3 (GM3-d5) sample contains a deuterium-labeled lipid chain and is thus 5.031 Da heavier than that of its non-labeled counterpart. The MS/MS spectrum of GM3-d5 (FIG. 5, bottom) very similar to that of GM3 (FIG. 5, top). In fact, they had the same B and C-fragments, while fragments containing the lipid moiety exhibited an m/z 5.031 difference between the two spectra, reflecting the isotopic labels.

A second example is the MS/MS spectra of a commercial GD3 sample isolated from natural sources, which contains different lipids. Full B- and Y-fragment coverages (3 C-fragments and 2 Z-fragments) were observed for GD3 (39:1) in addition to a few internal fragments, notably $B_2Z_3$ and $B_3Y_3$. Although the commercial GD3 sample was claimed to be "pure", it was found to be one of the more "impure" GSL standards tested. However, this "impure" sample allowed the detection of many different lipid forms of GD3. Overall, the MS/MS spectra of the two other lipid forms of GD3, (40:1) and (41:1), exhibited similar fragmentation patterns as that of GD3 (39:1) (FIG. 6). In particular, fragments that do not retain the lipid (B, C, BY, BZ fragments) are conserved among all of the three MS/MS spectra. However, as GD3 produced more fragment ions, the difference between its non-reducing and reducing end fragments is more striking. As a result, fragments that retain the lipid (Y and Z fragments and with neutral water loss) are shifted to show the different lipid masses, that is, 14 mass unit difference between GD3 (39:1) and GD3 (40:1) and 28 mass units between GD3 (39:1) and GD3 (41:1).

Both examples above, as well as other glycolipids studied so far, showed that for the MS/MS spectra of glycolipids having the same glycan but different lipids the glycan fragments were essentially the same, but the fragments containing the lipid showed a predictable mass shift. This mass shift is typically 14n ($n\times CH_2$) and/or 2n' ($n'\times H_2$) (where n and n' are each an integer). One can thus utilize the fragmentation patterns of glycans to characterize both different glycolipid classes (e.g., GD3 vs. GM3) and various lipid forms of the same glycolipid class (i.e., glycolipids containing the same glycan but different lipids). Therefore, an MS/MS database of glycolipids can be useful for analyzing and gaining insights into both the glycoforms and the lipid profiles of glycolipids derived from natural sources.

A study was conducted on a commercial sample of "pure" GD2 derived from biological sources (FIG. 7, top). Using traditional methods, namely searching precursor masses and/or known fragment ions, only a single distribution was found at retention time (Rt) of 25.3 min (FIG. 7, middle). In this case, the available reference spectrum was GD2 (36:1) and the LC-MS/MS data was searched for that precursor ion. However, when the data was analyzed using the B-glycan fragments of GD2, including $B_{1a}$, $B_3Y_{2a}$, $B_{2a}$, $B_3Y_{2b}$, $B_3$ and $B_4$, as in the first stage of our two-stage searching process, five distributions were observed at Rt of 25.3, 26.7, 29.4 and 31.8 min (FIG. 7, bottom). After evaluation of the precursor and Y-ion mass shifts from the reference spectrum of GD2 (36:1), as in the second stage of our two-stage searching process, the downstream distributions were found to be various lipid forms of GD2 (36:1), including GD2 (36:2) at 26.7 min, GD2 (38:1) at 28.6 min, GD2 (38:2) at 29.4 min, and GD2 (40:1) at 31.8 min. This short study demonstrated that glycolipids not physically present in the database can be identified using our searching method, and, by searching specifically for glycoforms additional glycolipids previously undiscovered may be identified.

The data collection and analysis of GM3 (32:1) was as follows. The corresponding MS/MS spectrum was acquired at a specific retention time from the LC-MS/MS data set. Preferably, the data was acquired in centroid mode. However, data acquired in profile mode can be converted into the appropriate centroid format. After reviewing the data and determining the level at which the true ion signal rises out of the noise, the threshold for the ion signal is set. After removing the noise below the threshold signal, the resulting stick spectrum shows only true signal. Isotope peaks can also be removed so that only the main monoisotopic mass (generally the first and most abundant isotopic peak/mass) is used for all characterization.

The peaks are then labeled based on fragment identity and classified as "glycan fragment" or "lipid fragment". Glycan fragments are defined as fragmentation of the glycoside bond resulting in charge retention on the glycan portion of the fragment. In this case, no part of the lipid chain would be retained. Lipid/glycolipid fragments are defined as fragmentation of the glycoside bond resulting in charge retention on the glycolipid portion of the fragment (the charge may reside on either the glycan or lipid moiety). In this case, the fragment would contain all or some of the lipid chain as well as some of the glycan. These fragments can also result in cleavages of the lipid portion, in which glycan cleavages did not occur. The most common "non-glycan" cleavages observed are water loss (that may occur on the sphingolipid head or on the glycan) or cleavages around the lipid head group. While pure "lipid" cleavages (aside from neutral water loss) have not been observed in the glycolipid standards to a significant degree, these cleavages should not be discounted entirely. The program is automated to regard lipid containing fragments (i.e., [M–H$_2$O], Y, Z, etc.) as "lipid" fragments, and non-lipid containing fragments (i.e., B, C, BC, BY, BZ, CY, CZ, BB, CC, etc.) as "glycan" fragments.

GM3 (32:1) MS/MS peaks with user defined fragment identification are shown in Table 1, below. The "in program filing" is defined based on the "fragment ID" given by the user. Only a partial list is shown. Some fragments may not be labeled. In that case, these fragments either would be neglected from matching entirely, or may float between "shifting" and "not shifting" fragment lists to assist in helping determine the fragment's identity. A first attempt will try to match with the "non-shifting" fragments. If the fragments are not conserved (i.e., the fragment mass does not appear at the same mass observed), then a second attempt will try to match them with the "shifted" fragments.

TABLE 1

| In program filing | Fragment ID | m/z | Intensity (counts) |
|---|---|---|---|
| | | 274.0907 | 377 |
| Glycan | B1 | 292.1012 | 1250 |
| Glycan | B2 | 454.1531 | 3745 |
| | | 530.5264 | 314 |
| | | 531.4048 | 1719 |
| Lipid | Z0 | 548.5372 | 8358 |
| | | 553.3866 | 621 |
| Lipid | Y0 | 566.5476 | 16658 |
| | | 569.5629 | 341 |
| Glycan | B3 | 616.2051 | 908 |
| Lipid | Z1 | 710.5888 | 5360 |
| Lipid | Y1 | 728.5994 | 40525 |
| Lipid | Z2 | 872.6405 | 1697 |
| Lipid | Y2 | 890.6514 | 8685 |
| | | 1019.6930 | 337 |
| Lipid | M—H20 | 1163.7350 | 11459 |
| Lipid (M) | M + H | 1181.7460 | 68778 |

The fragment list is then divided into a "glycan" fragment list and a "lipid" fragment list. Since the exact intensities may or may not be observed in the experimental data, the intensity values should also be converted to relative ratios. Although this example includes M ([M+H]$^+$) in the relative intensity calculations, this intensity may want to be neglected from database relative intensity determinations. As fragmentation occurs, the precursor ions (e.g., [M+H]$^+$) is used up to generate the observed fragment ions. If one increases the activation energy, more precursor ion would be used (precursor ion intensity decreases), which would generate more fragments. In this case, the relative intensities between the fragment ions would remain fairly stable, but the precursor ion intensity would be reduced, and its intensity relative to the fragment ions would not be the same. For this reason, the precursor ion ([M+H]$^+$, [M+NH$_4$]$^+$, etc.) can be omitted from relative intensity conversions and ion intensity matching.

The Glycan fragment list would be searched directly. No mass shifting would be applied. The Lipid/glycolipid fragment list would have the option of uniformly shifting the masses for direct matching to experimental data. The Non-labeled fragments can be generated into a "floating" list, separate from the Glycan and Lipid/glycolipid fragment lists, or it may be neglected from matching entirely. This "floating" list would attempt first a direct match, as with the Glycan fragment list. Those masses conserved would be labeled as Glycan (with an indication that the program assigned the general "glycan" match from this "floating" list). Those masses not conserved would attempt a shifting match, as with the Lipid/glycolipid fragment list. Those masses matched with the other Lipid/glycolipid fragments would be labeled as Lipid (indicating a "lipid" match from the "floating" list). The application of a "floating" list would be necessary if the user would want to input their own glycolipid database data (allowing for the possibility of impure sources and/or isobaric fragmentation interference.

Glycan Fragment Matching List for GM3 (32:1)

| Fragment ID | m/z | Relative Intensity (%) |
|---|---|---|
| B1 | 292.1012 | 3 |
| B2 | 454.1531 | 9 |
| B3 | 616.2051 | 2 |

Lipid/Glycolipid Fragment Matching List for GM3 (32:1)

| In program filing | Fragment ID | m/z | Relative Intensity (%) |
|---|---|---|---|
| Lipid | Z0 | 548.5372 | 21 |
| Lipid | Y0 | 566.5476 | 41 |
| Lipid | Z1 | 710.5888 | 13 |
| Lipid | Y1 | 728.5994 | 100 |
| Lipid | Z2 | 872.6405 | 4 |
| Lipid | Y2 | 890.6514 | 21 |
| Lipid | M- H2O | 1163.7350 | 28 |
| Lipid (M) | M + H | 1181.7460 | |

"Floating" Fragment Matching List for GM3 (32:1)

| In program filing | Fragment ID | m/z | Relative Intensity (%) |
|---|---|---|---|
| | | 274.0907 | 1 |
| | | 530.5264 | 1 |
| | | 531.4048 | 4 |
| | | 553.3866 | 2 |
| | | 569.5629 | 1 |
| | | 1019.6930 | 1 |

For searching experimental data, the Database Glycan lists would first be searched against the experimental list. Spectra that match a Glycan list would be given the Glycan name. This spectrum would then be searched against the Lipid list for that given Glycan list. Spectra that do not match any of the Glycan lists would not be labeled. Additional mass matching would not be required. The feature would then remain unidentified. This step also includes some evaluation of fragment relative intensities. Perfect matches here are not necessary, just a general comparison of intensity ranges.

GM3 Glycan List (Given from the Examples Above)

| Fragment ID | m/z | Relative Intensity (%) |
|---|---|---|
| B1 | 292.1012 | 2 |
| B2 | 454.1531 | 5 |
| B3 | 616.2051 | 1 |

GM1 Glycan List

| Fragment ID | m/z | Relative Intensity (%) |
|---|---|---|
| B1b | 292.1017 | 1 |
| B2a | 366.1383 | 100 |
| B3Y2a | 454.1540 | 2 |
| B3Y2b | 528.1907 | 1 |
| B3Y3a | 657.2323 | 2 |
| B3 | 819.2845 | 3 |
| C3 | 837.3038 | 0.2 |
| B4 | 981.3377 | 12 |

GD3 Glycan List

| Fragment ID | m/z | Relative Intensity (%) |
|---|---|---|
| B2Z3 | 274.0925 | 10 |
| B1 | 292.1025 | 25 |
| B3Z3 | 436.1410 | 1 |
| B3Y3 | 454.1554 | 31 |
| B2 | 583.1979 | 41 |
| B3 | 745.2506 | 100 |
| C3 | 763.2606 | 2 |
| B4 | 907.3031 | 41 |

The MS/MS of an unknown sample, "Unknown 1", was collected. The precursor had an m/z of 1186.77 and was tentatively assigned $[M+H]^+$. Tentative precursor assignment is based on user defined/possible adducts and mass differences in MS1 spectra at similar retention times. Since this is an experimental list, all masses from the MS/MS spectrum need to be transferred in and the exact ion intensities should be converted to relative intensities. As with the database relative intensities, the precursor ion should be neglected from relative intensity calculations. Unlike with database entries, "Glycan" and "Lipid" determinations will be automated based on spectra searching.

| m/z | Relative Intensity |
|---|---|
| 264.2700 | 1 |
| 274.0900 | 3 |
| 282.2800 | 0.2 |
| 292.1000 | 9 |
| 310.1100 | 0.2 |
| 325.1100 | 0.1 |
| 418.1300 | 0.4 |
| 454.1500 | 15 |
| 523.5600 | 0.5 |
| 531.4000 | 3 |
| 535.5600 | 3 |
| 553.5679 | 87 |
| 571.5783 | 78 |
| 580.1816 | 0.3 |
| 616.2043 | 2 |
| 624.6239 | 0.2 |
| 656.6125 | 1 |
| 663.4494 | 0.3 |
| 697.6104 | 0.2 |
| 715.6196 | 51 |
| 733.6299 | 100 |
| 844.6613 | 0.2 |
| 845.665 | 0.1 |
| 862.6714 | 0.3 |
| 877.6714 | 16 |
| 895.6811 | 28 |
| 1006.715 | 1 |
| 1024.722 | 1 |
| 1168.764 | 42 |
| 1184.836 | 4 |
| 1186.775 | |

To illustrate matching and non-matching ions/fragments, matched fragments will be labeled "MATCH". If a fragment from a Glycan list is not observed, a null entry will be added to the experimental list and the non-matched mass will be shown in the appropriate Glycan list column. To assist in match/non-match evaluations, matches will be indicated with MATCH (the MATCH notation in GM3 indicates matches to the "floating" list). The below is an illustration for understanding. This step is not visualized in the program. A Glycan match would result from all or most Glycan mass matches. Some low relative intensity Glycan fragments may not be observed (this should be reflected in the scoring). If most of the Glycan fragment masses do not match, this will result in a non-match for that Glycan.

| Exp'tal m/z | GM3 Glycan list | GM1 Glycan list | GD3 Glycan list |
|---|---|---|---|
| 264.2700 | | | |
| 274.0900 | *MATCH* | | MATCH |
| 282.2800 | | | |
| 292.1000 | MATCH | MATCH | MATCH |
| 310.1100 | | | |
| 325.1100 | | | |
| 418.1300 | | 366.1383 | |
| 454.1500 | MATCH | MATCH | 436.1410 MATCH |
| 523.5600 | | | |
| 531.4000 | *MATCH* | 528.1907 | |
| 535.5600 | | | |
| 553.5679 | | | |

-continued

| Exp'tal m/z | GM3 Glycan list | GM1 Glycan list | GD3 Glycan list |
|---|---|---|---|
| 571.5783 | | | |
| 580.1816 | | | |
| | | | 583.1989 |
| 616.2043 | MATCH | | |
| 624.6239 | | | |
| 656.6125 | | | |
| | | 657.2323 | |
| 663.4494 | | | |
| 697.6104 | | | |
| 715.6196 | | | |
| 733.6299 | | | |
| | | | 745.2506 |
| | | | 763.2606 |
| | | 819.2845 | |
| | | 837.3038 | |
| 844.6613 | | | |
| 845.665 | | | |
| 862.6714 | | | |
| 877.6714 | | | |
| 895.6811 | | | |
| | | | 907.3031 |
| | | 981.3377 | |
| 1006.715 | | | |
| 1024.722 | | | |
| 1168.764 | | | |
| 1184.836 | | | |
| 1186.775 | | | |

In this case, GM3 yielded a 100% Glycan fragment match and a nominal relative intensity match, which would result in fragment identification (of the matched Glycan fragments) and labeling the Unknown 1 a GM3 glycolipid. Since GM1 matched 2 fragments but did not match 6 fragments, this would result in a no match with GM1. Similarly, GD3 matched 3 fragments but did not match 5 fragments, resulting in a no match with GD3.

The Glycan fragment matches would then be removed from the Experimental mass list. This abbreviated list can be compared to the Lipid list from the matched Glycan. Italicized masses indicate a Glycan mass match with the "floating" Database list.

| m/z | Relative Intensity |
|---|---|
| 264.2700 | 1 |
| *274.0900* | *3* |
| 282.2800 | 0.2 |
| 310.1100 | 0.2 |
| 325.1100 | 0.1 |
| 418.1300 | 0.4 |
| 523.5600 | 0.5 |
| *531.4000* | *3* |
| 535.5600 | 3 |
| 553.5679 | 87 |
| 571.5783 | 78 |
| 580.1816 | 0.3 |
| 624.6239 | 0.2 |
| 656.6125 | 1 |
| 663.4494 | 0.3 |
| 697.6104 | 0.2 |
| 715.6196 | 51 |
| 733.6299 | 100 |
| 844.6613 | 0.2 |
| 845.665 | 0.1 |
| 862.6714 | 0.3 |
| 877.6714 | 16 |
| 895.6811 | 28 |
| 1006.715 | 1 |
| 1024.722 | 1 |

-continued

| m/z | Relative Intensity |
|---|---|
| 1168.764 | 42 |
| 1184.836 | 4 |
| 1186.775 | |

For searching experimental data, the Database Lipid precursor ion for the matched Glycan would be compared to the Experimental precursor ion. Once a mass difference has been established, the lists can be compared.

If (Experimental Unknown 1 precursor mass)>(Database Lipid precursor mass), then, (High mass shift)=(Experimental Unknown 1 precursor mass)−(Database Lipid precursor mass), and (Database Lipid list masses)+(High mass shift)=(New Database List).

If (Experimental Unknown 1 precursor mass)<(Database Lipid precursor mass), then, (Low mass shift)=(Database Lipid precursor mass)−(Experimental Unknown 1 precursor mass), and (Database Lipid list masses)−(Low mass shift)=(New Database List).

The (New Databased List) is used to compare/match with the (Abbreviated Experimental Unknown list).

Lipid precursor ion/mass for GM3 (32:1)= $[M+H]^+$=1181.7460 and the experimental Unknown 1 precursor mass=$[M+H]^+$=1186.7750, thus the experimental unknown precursor mass is greater than the database lipid precursor match and the high mass shift is 5.0291 (1186.7750-1181.7460).

The "new m/z" column indicates the new masses that would be compared to the Abbreviated mass list. The Fragment ID and relative intensity would not be affected by this action.

| In program filing | Fragment ID | m/z | Relative Intensity (%) | New m/z |
|---|---|---|---|---|
| Lipid | Z0 | 548.5372 | 21 | 553.5663 |
| Lipid | Y0 | 566.5476 | 41 | 571.5767 |
| Lipid | Z1 | 710.5888 | 13 | 715.6179 |
| Lipid | Y1 | 728.5994 | 100 | 733.6285 |
| Lipid | Z2 | 872.6405 | 4 | 877.6696 |
| Lipid | Y2 | 890.6514 | 21 | 895.6805 |
| Lipid | M- H2O | 1163.7350 | 28 | 1168.7641 |
| Lipid (M) | M + H | 1181.7460 | | 1186.7751 |

Considerations for this step.

When comparing precursor masses, other adduct masses should also be considered. Adducts serve to change the ion mass even if the molecule is unchanged. For example, GD3 has a neutral mass of 1180, but in order for the MS to manipulate it (move, isolate, activate, detect, etc.), GD3 need a charge carrier, or adduct, that adds mass to the molecule. For example, a mass difference (high mass shift) of 17.0265 would indicate an ammoniated ion of the same precursor (i.e., $[M+NH_4]^+$). For the example of GD3 as the precursor, the mass would be appear to be around 1197 (1180+17.0265). In general, the fragmentation pattern does not change with adducts, so $[GD3+Na_4]^+$ would have the same fragment masses and intensities as the reference $[GD3+H]^+$. In this case, the precursor mass would not be identical, but many of the fragment masses would, depending how the fragments are charged. The Database glycolipid lists are mostly protonated. Meaning, the precursor ion is protonated and all the fragments are protonated. In general, adducts can include $H^+$, $NH_4^+$, $Na^+$, $K^+$, and $(-H_2O+H)^+$. Users can also select their own adducts.

Only select mass differences should be allowed. Lipids can grow or shrink by 1 CH2 group=14.0165. Commonly, lipid changes occur in twos, $C_2H_4$=28.0313. By default, changes of $C_2H_4$ may only be allowed unless single methyl changes ($CH_2$) are selected to be allowed. Lipids can also have multiple unsaturation points (i.e., C—C double bonds=2.0157). Most of the Database lipids have 1 point of unsaturation (1 double bond). A loss of 1 unsaturation (−2.0157) would be allowed, and additional unsaturation (+2.0157) may be allowed.

Database GM3 unsaturation=1 (32:1)

Database GM3 carbons=32 (32:1)

Low limitation=1−1=0→No more unsaturation allowed
    1 (−2.0157) low mass shift allowed High limitation=based on the number of carbons Additional mass differences may be allowed based on user input. Often, lipids may be isotopically modified or chemically modified. Chemical modifications are not particularly limited and can include, but are not limited to, covalent tags (e.g., fluorescence tags or the like), biological modifications, or modifications that are preparatory in origin (e.g., oxidation or methylation). Options of deuteration, carbon-13, nitrogen-15, and oxygen-18 (most common isotope tags) are allowable by the user. Additional isotopes, modifications, and/or tags may be selected by the user (via a user-defined option). This option would not be default. The user must select isotope, modification, or tag mass options. Otherwise, observed mass differences matching these would not be labeled.

In this example, the mass difference was determined to be 5 deuterations with a mass accuracy matching of 1.9 ppm. Mass accuracy windows are user defined and are generally asset to a range of about 3 to 7 ppm (i.e., matches occurring for 0-3 ppm or 0-7 ppm) for high-resolution instrumentation. However, mass accuracy windows will depend on the user's instrument and analytical conditions. For example, low-resolution instrumentation (e.g., quadrupolar based detectors, including quadrupoles and ion traps) would require wider mass accuracy windows (typically between 0.5-1 Da), while higher resolution instrumentation (e.g., time-of-flight and orbitrap analyzers) could have narrower mass accuracy windows (e.g., <50 ppm). Assuming the user has selected to allow deuteration mass matching, this assignment would be allowed. If the user has not allowed deuteration mass matching, the lipid could not be assigned.

Once the mass shift has been assigned an identity and the New Database List made to correspond to the mass shift, the New Database Lipid list can be compared to the Abbreviated Experimental list.

GM3 (32:1)+(High mass shift)=GM3 (32:1)−d5

GM3 (32:1)−d5 Database Lipid list

| In program filing | Fragment ID | m/z | Relative Intensity (%) |
|---|---|---|---|
| Lipid | Z0 | 553.5663 | 21 |
| Lipid | Y0 | 571.5767 | 41 |
| Lipid | Z1 | 715.6179 | 13 |
| Lipid | Y1 | 733.6285 | 100 |
| Lipid | Z2 | 877.6696 | 4 |
| Lipid | Y2 | 895.6805 | 21 |
| Lipid | M- H2O | 1168.7641 | 28 |
| Lipid (M) | M + H | 1186.7751 | |

Comparison of abbreviated experimental spectral list against New Database Lipid list. To illustrate matching and non-matching ions/fragments, matched fragments will be labeled "MATCH". If a fragment from a Lipid list is not observed, a null entry will be added to the experimental list and the non-matched mass will be shown in the appropriate Lipid list column. The italicized masses indicate masses that had a Glycan match from the "floating" list. The MATCH notation in GM3 list indicates a lipid match to the "floating" list. This step is visualized for understanding and does not need to be visualized in the program. A Lipid match would result from all or most New Lipid mass matches. Some low relative intensity Lipid/glycolipid fragments may not be observed (this should be reflected in the scoring). If most of the Lipid/glycolipid fragment masses do not match, this will result in a non-match for that Glycolipid.

| m/z | Relative Intensity | GM3 (32:1)-d5 Lipid list |
|---|---|---|
| 264.2700 | 1 | |
| *274.0900* | *3* | |
| 282.2800 | 0.2 | |
| 310.1100 | 0.2 | |
| 325.1100 | 0.1 | |
| 418.1300 | 0.4 | |
| 523.5600 | 0.5 | |
| *531.4000* | *3* | |
| 535.5600 | 3 | *MATCH* |
| 553.5679 | 87 | MATCH |
| 571.5783 | 78 | MATCH |
| 580.1816 | 0.3 | |
| 624.6239 | 0.2 | |
| 656.6125 | 1 | |
| 663.4494 | 0.3 | |
| 697.6104 | 0.2 | |
| 715.6196 | 51 | MATCH |
| 733.6299 | 100 | MATCH |
| 844.6613 | 0.2 | |
| 845.665 | 0.1 | |
| 862.6714 | 0.3 | |
| 877.6714 | 16 | MATCH |
| 895.6811 | 28 | MATCH |
| 1006.715 | 1 | |
| 1024.722 | 1 | *MATCH* |
| 1168.764 | 42 | MATCH |
| 1184.836 | 4 | MATCH |
| 1186.775 | | |

Since all the Shifted Lipid masses (from the "New" database lipid list) were also observed in the Experimental Unknown mass list, this Unknown would be labeled "GM3" from the Glycan matching and "(32:1)−d5" from the Lipid matching to give the complete label: GM3 (32:1)−d5. The matching score here would still be high as the un-matched experimental fragments are all low relative intensity.

An embodiment of the process for database entry is shown in FIG. 8. An embodiment of the process for experimental glycolipid searching is shown in FIG. 9.

Determination of GSLs in Plasma and Tissue

Extraction of glycolipids from human plasma. Human plasma (50 µL) was mixed with 1800 µL of water, methanol and chloroform (3:4:2, v/v/v) in a glass centrifuge tube, and the mixture was vortexed vigorously at room temperature (rt, ~20-25° C.) for 10-30 sec. Thereafter, the mixture was incubated at −20° C. for 2 h, thawed at rt for 1-2 min, and then centrifuged at ~15k×g for 10 min. The mixture was separated into three layers. The top layer was transferred to a ½ dram glass vial. The remaining was extracted again by the same protocol using 900 µL of the same extraction solvent. The top layers were combined and dried using a SpeedVac concentrator for 0.5-2 hr until completely dried. The dried material in each vial was reconstituted in 150 μL 1% chloroform in methanol. The samples were transferred to a 2 mL-total recovery autosample vial for LC-MS/MS analysis. For experiments to test glycosphingolipid (GSL) recovery, a GSL mixture standard (30 μL) was added to the plasma sample before extraction. The GSL mix standard was prepared in methanol using equal GM3, GM2, and GM1 (Avanti Lipids) for a 10 ug/mL mix standard.

Extraction of glycolipids from tissue. A mass of tissue material (5-10 mg, mouse brain or human brain) was combined with 600 μL of water in a 2.0 mL tube prefilled with zirconium bead (1.5 mm, TriplePure M-Bio Grade). The tube was applied to a BeadBug homogenizer in 5-30, 30 sec bursts, resting 30 sec between each burst, until the tissue appeared fully liquefied. The homogenized material was transferred to a glass centrifuge tube and subjected to extraction in the same manner described above, except that no additional water was added. For experiments to test GSL recovery, a GSL mixture standard (5 μL) was added to the homogenized mouse brain sample before extraction.

Evaluation of spiked biological GSL samples. Biological matrices of human plasma, mouse brain, and human brain were extracted for GSLs. Because the abundance of natural GSLs are low in human plasma, a mixture of GSL standards was prepared and spiked into the plasma. Extracted ion chromatograms (EIC) of the most abundant GSL mix standard lipid forms (i.e., GM3 (36:1), GM2 (36:1), and GM1 (36:1)) are shown in FIG. 10 (top). Without the GSL spike standard, no mix GSLs were found in plasma. With the GSL spike standard, GSLs were detected. In parallel to this plasma spiking study, mouse brain homogenate was also analyzed with and without a GSL spike (FIG. 10, bottom); although, unlike plasma, which showed a lack of endogenous GSLs, mouse brain showed a natural GSL abundance. This observation matches the expectations of GSL presence in brain tissue. These plasma and brain extracts were then analyzed by LC-MS/MS and their GSL content evaluated using the previously described two-stage matching methodology.

Initial investigations focused on the exogenously spiked GSLs added to the plasma and mouse brain samples. Since the GSL mix contained three known GSL species (GM1, GM2, and GM3), the investigation could be streamlined to only those glycoforms and their various lipid forms. While these GSLs contain a similar structural composition, structural complexity increases from GM3 to GM2 to GM1 as the number of sugar residues increases (3 sugar residues for GM3, 4 sugar residues for GM2, and 5 sugar residues for GM1). Additionally, GM2 and GM1 correspond to branched GSL structures, while GM3 represents a linear GSL. These 3 GSL structures, represented chemically and using carbohydrate symbology, are shown in FIG. 11.

The first investigation focused on the linear trisaccharide GSL, GM3. Its principal component in the solution-based standard was GM3 (36:1) (m/z 1181.7517) and this lipid form was used for the in-house GSL database. Its product spectrum showed 3 carbohydrate ions (glycan fragments)— $B_1$, $B_2$, and $B_3$ (m/z 292.1027, 454.1555 and 616.2083, respectively)—and 8 glycolipid ions (lipid/glycolipid fragments)—$Y/Z_0$, $Z_0$—$H_2O$, $Y/Z_1$, $Y/Z_2$, and M—$H_2O$. Eluting at 28.6 min, the same lipid form was found in the spiked plasma, spiked mouse brain, and unspiked mouse brain at 28.6 min, 25.8 min, and 25.8 min, respectively (FIG. 10). Next, the first-stage of the searching method was applied. The results were searched for product spectra containing the 3 carbohydrate ions from the GM3 database spectrum. An example of these results is shown in FIG. 12 for the spiked plasma sample. Each line in the MSMS EIC represents a possible product spectrum that contains the GM3 carbohydrate ions and, thus, requires further evaluation. As demonstrated by these results, several product spectra in the GM3 elution range (i.e., 20-40 min based on retention similarity to GM3 (36:1)) contained at least one of the three product ions.

Next, the second-stage of the searching method was applied to the filtered results. The 8 GM3 database glycolipid ions (lipid/glycolipid fragments) were shifted by expected m/z increments of 28 (+/−$C_2H_4$) and/or 2 (+/−2H). GM3 lipid form matches resulted from product spectra containing appropriately shifted glycolipid ions masses that still retained the relative ion intensities displayed in the original database product spectrum. Spiked plasma GM3 lipid form matches are shown in FIG. 13. FIG. 13A shows the GM3 database MSMS spectrum, as acquired from the solution based standard. The $B_1$, $B_2$, and $B_3$ dashed drop lines illustrate the first matching stage—matching the carbohydrate ions (glycan fragments)—and the solid drop lines illustrate the original glycolipid product masses from the database spectrum. The $Z_0$, $Y_0$, $Z_1$, $Y_1$, $Z_2$, and $Y_2$ dashed drop lines indicate the uniform shift in the glycolipid ion masses as the lipid form changes. In the spiked plasma sample, 5 GM3 lipid forms could be identified: 34:1, 36:1, 38:1, 40:1, and 42:1 (FIG. 13B-F, respectively). Some variations in relative intensity are expected as fragmentation from additional isobaric lipids may influence product ion intensities. However, relative intensities should still be similar to the database spectrum. An example of this is shown in FIG. 13D, where the $Y_0$ relative intensity is more similar to the $Z_0$ relative intensity. Likely, an isobaric precursor contributed to the higher than expected $Y_0$ ion relative intensity. It should be noted, the $Y_0$ relative intensity is not greatly different from expected and the other ion relative intensities are also similarly matched to the database relative intensities. Finally, as anticipated, none of these lipid forms were detected in the unspiked plasma, which meant that all these lipids were added from the GSL spike.

Analysis of GM2 and GM1 were performed similarly. Both GSLs represented more structurally complex glycans, moving from GM3's linear glycan configuration to branched glycan configurations, while additionally increasing the overall number of sugar residues (FIG. 11). Correspondingly, the product spectra complexity increased as well. In addition to B, C, Y, and Z-type ions, internal fragments were observed for both the carbohydrate classified ions as well as the glycolipid ions. As previously defined, carbohydrate ions contain only the glycan moiety, and include carbohydrate internal ions (i.e., BY, CY, BZ, and CZ product ions) that result from two glycosidic bond cleavages instead of only one. Similarly, glycolipid internal ions (i.e., YZ, YY, or ZZ product ions) are the result of two glycosidic bond cleavages so that both the glycan and ceramide moiety are retained in the product ion. These ions served to increase the spectral specificity for each GSL species.

The GM2 database product spectrum showed 6 carbohydrate product ions that would be used for stage-one GM2 species filtering: $B_{1a}$, $B_2Y_{2a}$, $B_2Y_{2b}$, $B_2$, $C_2$, and $B_3$ ions at m/z 292.1027, 366.1427, 454.1582, 657.2360, 675.2455, and 819.2890, respectively. GM1 resulted in 7 carbohydrate product ions: $B_{1b}$, $B_{2a}$, $B_3Y_{2a}$, $B_3Y_{2b}$, $B_3Y_{3a}$, $B_3$, and $B_4$ ions at m/z 292.1017, 366.1383, 454.1540, 528.1907, 657.2323, 819.2845, and 981.3377, respectively. The second-stage GM2 lipid form matching would be performed by shifting the 9 glycolipid product ions: $Z_0$, $Y_0$, $Y_1$, $Y_{2b}Z_{2a}$, $Y_{2a}Y_{2b}$, $Z_{2a}$, $Y_{2a}$, $Z_{2b}$, and $Y_{2b}$. GM1 lipid form matching used 8 glycolipid product ions: $Z_0$, $Y_0$, $Z_1$, $Y_1$, $Y_{2a}Z_{2b}$, $Y_{2a}$, $Y_{2b}$, and $Y_{3a}$ ions. The two-stage GSL matching methodology was applied to a GSL spiked plasma sample, an unspiked plasma sample, a GSL spiked mouse brain sample, and an unspiked mouse brain sample. The results of the GSL matching, focusing on the GSL spiked species, are summarized in Table 2. Abbreviated standard results are provided for comparative purposes, including: lipid forms detected in the biological matrices, the simplest low mass lipid form, and the simplest high mass lipid form. The simplest being based on +/−28 m/z (e.g., $C_2H_2$), without considering different oxidative forms. Both the low mass and high mass standard lipid forms represent the least concentrated lipid forms possible for the spiked samples. Although not every standard lipid form was observed in the biological extracts, these results do indicate the extraction efficiency was sufficient to detect even some of the less abundant lipid forms. Table 2 is divided by GSL species (i.e., GM3, GM2, and GM1) and organized by increasing lipid form mass. Checks indicate the GSL was observed in the biological matrix and crosses indicate that the GSL was not detected, using the two-stage GSL MSMS matching of the disclosure. As a comparison, abbreviated results of GSL presence in the solvent-based standard LC-MS/MS results are also provided.

isobars) that the inventors have not been able to separate chromatographically. While these product spectra have been acquired separately and are entered as 2 separate GSL species database entries, the natural overlap of the experimental product spectra mean these GSLs are often identified as the more general "GD1", with "a" or "b" only being assigned if unique carbohydrate fragments are absent from the experimental product spectrum. An example of the non-resolved GD1 chromatogram and its hybrid product spectrum is shown in FIG. 14. It should also be noted, GD1a/b can be separated using ion mobility (IMS). Therefore, if the two-stage GSL matching methodology were applied to an LC-IMS-MS/MS data set, identification of GD1a and/or GD1b GSL species could be performed. An example of GD1a/b identification from a mixture is shown in FIG. 15 using data collected by Bruker using a timsTOF Pro. The two-stage matching methodology of the disclosure was applied manually to the brain samples. The GLS identification results are compared to traditional matching using spectral matching with SimLipid and LipidBlast libraries as well as assisted manual searching aided by MetaboScape's peak picking algorithm.

As already demonstrated from the Table 2 results, mouse brain contained several endogenous GSLs. However, GD3 and GD1 species were detected in the unspiked mouse brain, in addition to the GM3, GM2, and GM1 lipid forms already

TABLE 2

| GSL ID | Theoretical m/z | Solvent standard(s) | Plasma (spiked) | Plasma (unspiked) | Mouse brain (spiked) | Mouse brain (unspiked) |
|---|---|---|---|---|---|---|
| GM3 (32:1) | 1125.6892 | ✓ | ✗ | ✗ | ✗ | ✗ |
| GM3 (34:1) | 1153.7204 | ✓ | ✓ | ✗ | ✓ | ✗ |
| GM3 (36:1) | 1181.7517 | ✓ | ✓ | ✗ | ✓ | ✓ |
| GM3 (38:1) | 1209.7830 | ✓ | ✓ | ✗ | ✓ | ✗ |
| GM3 (40:1) | 1237.8143 | ✓ | ✓ | ✗ | ✓ | ✗ |
| GM3 (42:1) | 1265.8456 | ✓ | ✓ | ✗ | ✗ | ✗ |
| GM3 (44:1) | 1293.8144 | ✓ | ✗ | ✗ | ✗ | ✗ |
| GM2 (34:1) | 1356.7999 | ✓ | ✗ | ✗ | ✗ | ✗ |
| GM2 (36:1) | 1384.8310 | ✓ | ✓ | ✗ | ✓ | ✓ |
| GM2 (38:1) | 1412.8623 | ✓ | ✓ | ✗ | ✓ | ✓ |
| GM2 (40:1) | 1440.8938 | ✓ | ✗ | ✗ | ✗ | ✗ |
| GM1 (34:1) | 1518.8526 | ✓ | ✗ | ✗ | ✓ | ✓ |
| GM1 (36:2) | 1544.8695 | ✓ | ✗ | ✗ | ✓ | ✓ |
| GM1 (36:1) | 1546.8839 | ✓ | ✓ | ✗ | ✓ | ✓ |
| GM1 (38:1) | 1574.9152 | ✓ | ✓ | ✗ | ✓ | ✓ |
| GM1 (40:1) | 1602.9465 | ✓ | ✗ | ✗ | ✗ | ✗ |

The brain tissue samples were further evaluated using a slightly less targeted approach. LC-MS/MS results were analyzed using the two-stage GSL methodology of the disclosure for all GSLs in the in-house reference database, which allowed for identification of 8 total GSL species: GM1, GM2, GM3, GD1a, GD1b, GD2, GD3 and GB4. It should be noted that GD1a and GD1b are isomers (and, thus, noted. In total, 10 lipid forms across 5 GSL species were identified. The human brain sample(s) contained even more GSL species. Of those GSL species and lipid forms identified in mouse brain, only two of those lipid forms were not detected in human brain. Further, one additional GSL species, which were not found in mouse brain, could be identified in human brain. In total, human brain showed 13 lipid forms from 6 GSL species. These results are summarized in Table 3. Table 3 is divided by GSL species (e.g., GM3 and GD2) and organized by increasing lipid form mass. Checks indicate the GSL was observed in the biological sample and crosses indicate that the GSL was not detected in the biological sample, using the two-stage GSL MSMS matching of the disclosure.

TABLE 3

| GSL ID | Theoretical m/z | Mouse brain | Human brain |
|---|---|---|---|
| GM3 (36:1) | 1181.7517 | ✓ | ✓ |
| GM3 (38:1) | 1209.7830 | ✗ | ✓ |
| GM3 (40:1) | 1237.8143 | ✗ | ✓ |
| GM2 (36:1) | 1384.8310 | ✓ | ✓ |
| GM2 (38:1) | 1412.8623 | ✓ | ✓ |
| GM1 (34:1) | 1518.8526 | ✓ | ✗ |
| GM1 (36:2) | 1544.8695 | ✓ | ✗ |
| GM1 (36:1) | 1546.8839 | ✓ | ✓ |
| GM1 (38:1) | 1574.9152 | ✓ | ✓ |
| GD3 (36:1) | 1472.8471 | ✓ | ✓ |
| GD3 (38:1) | 1500.8784 | ✗ | ✓ |
| GD2 (36:1) | 1675.9265 | ✗ | ✓ |
| GD2 (38:1) | 1703.9578 | ✗ | ✓ |
| GD1 (36:1) | 1837.9793 | ✓ | ✓ |
| GD1 (38:1) | 1866.0106 | ✓ | ✓ |

The mouse and human brain samples were also processed using commercially available software. First, a more traditional annotation approach, SimLipid (Premier Biosoft International, v.6.05), was applied. This database program uses a proprietary lipid library, where each entry corresponds to a single lipid with a specific structural composition (i.e., specific lipid form), and each entry represents an individually acquired product spectrum. In the mouse brain sample, SimLipid yielded a 6 positive GSL identifications (GM3 (36:1), m/z 1181.7532; GM2 (36:1), m/z 1384.8334; GM1 (36:1), m/z 1546.8864; GD3 (36:1), m/z 1472.8501; GD1 (36:1), m/z 1837.9832; and GD1 (38:1), m/z 1866.0148). This is compared to the 10 GSLs positively identified using the two-stage methodology. Human brain resulted in slightly more GSL matches, with 10 GSL identifications (GM3 (36:1), m/z 1181.7528; GM3 (38:1), m/z 1209.7852; GM3 (40:1), m/z 1237.8164; GM2 (38:1), m/z 1412.8655; GM1 (36:1), m/z 1546.8882; GM1 (38:1), m/z 1574.9199; GD3 (36:1), m/z 1472.8508; GD3 (38:1), m/z 1500.8817; GD2 (38:1), m/z 1703.9631; and GD1 (38:1), m/z 1866.0176). In contrast, the two-stage methodology of the disclosure characterized 13 GSLs. Second, LipidBlast (v66) was used to annotate the data. LipidBlast, as previously noted, is a rules-based lipid library that predicts MSMS spectra based on the predictable shifting of product masses with changes in lipid chain structure. While spectra may initially be generated in vivo, all MSMS spectra have actually been experimentally verified for library entry. Therefore, while databased spectra do rely on initial in vivo rules-based generation, LipidBlast may also be considered a traditional annotation approach, where each entry corresponds to a single lipid form. In this case, LipidBlast searching resulted in no GSL annotations in either the mouse or human brain samples. Finally, manual searching was performed aided by peak picking from Metaboscape (v5.0). While ion searching was faster using this method, especially for evaluating multiple samples simultaneously, precursor and product ions of low abundance were easily missed during peak picking. Although missed precursor ions were expected—this is a common challenge in lipidomic analyses—the missing low abundance product ions were not expected. Metaboscape-aided searching could play a useful role in quickly evaluating GSL data, but modifications to the program would be necessary to make it as robust and reliable as pure, manual data excavation. Thus, the analysis using commercial software and prior art methods were unable to identify as many GSLs as the two-stage methodology of the disclosure, demonstrating the advantages of the two-stage methodology of the disclosure.

Instrumentation and Data Acquisition Parameters. For the biological samples (plasma and brain tissue), the following parameters were used to collect experimental data.

Mass spectrometry: Bruker Daltonics, Impact II Qq-TOF MS (or equivalent) using electrospray ionization (ESI), analyzed in positive mode, with a mid-mass optimized method (m/z 100-2500). The gas temperature was 200° C., the drying gas was nitrogen (4.0 L/min) and the nebulizer was 0.3 bar. The MS2 parameters included activation by collision induced dissociation (CID), data dependent activation (DDA) MSMS, and the inclusion mass range was m/z 500-2000.

| Nominal mass | Isolation range | Collision energy (CE) | Charge State (CS) |
|---|---|---|---|
| Base = m/z 800 | Window = ±m/z 2 | CE = 45 eV | CS = +1 |
| Base = m/z 1000 | Window = ±m/z 2 | CE = 30 eV | CS = +1 |
| Base = m/z 1100 | Window = ±m/z 2 | CE = 25 eV | CS = +1 |
| Base = m/z 1200 | Window = ±m/z 2 | CE = 25 eV | CS = +2 |

The injection system (for recalibration plug infusion) used a kd Scientific syringe pump (or equivalent) with a flow rate of 0.06 µL/hour.

Liquid chromatography was performed using a Thermo UltiMate 3000 series degasser (or equivalent), binary pump, column compartment, and autosampler as the injection system, with an injection volume of 5 µL.

Column: ThermoScientific Acclaim PepMap RSLC, C18 (300 µm×15 cm, 2 µm, 100 Å) (or equivilant)
    Loading pump trap—ThermoScientific C18 PepMap100µ-Precolumn (300 µm×5 mm, 5 µm, 100 Å) (or equivalent)
Column Temperature: 40° C.
The mobile phases were as follows:
NC pump: A=60/40 acetonitrile/water+10 mM ammonium formate+0.1% formic acid
    B=90/8/2 isopropanol/acetonitrile/water+10 mM ammonium formate+0.1% formic acid
Loading pump: A=water+0.1% formic acid
    B=acetonitrile+0.1% formic acid
Gradients for the LC-MS analysis were as follows:

| Time (min) | 0 | 5 | 15 | 60 | 80 | 100 | 105 | 140 |
|---|---|---|---|---|---|---|---|---|
| % B | 50 | 50 | 60 | 80 | 98 | 98 | 50 | 50 |
| % A | 50 | 50 | 40 | 20 | 2 | 2 | 50 | 50 |

Loading pump = 25 µL/min
NC pump = 5 µL/min

Bioinformatics and data processing was done with Bruker, Compass, v.5.1 (or equivalent), Bruker, Metaboscape v.4.0/v.5.0 (or equivalent), and Premier Biosoft International, SimLipid, v.6.05 (or equivalent).

All standards were received in solid form, usually in 1 mg quantities. All solid material was then dissolved in methanol for a stock solution of 1 mg/mL (1 mL volume of stock standard available). For LC-MS/MS analysis, standards were diluted to a final concentration of 10-50 µg/mL in methanol. Mixtures were prepared by combining select standards (from respective stock solutions) in methanol for a final concentration of 10-50 µg/mL (equal standard concentrations). The glycolipid spiking mixture contained GM3, GM2, and GM1.

Additional Considerations

Although the disclosure herein sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

Additional Examples

Structurally defined epimers, GlcNAc-LcGg4 and GalNAc-LcGg4, of the natural GSL antigen LcGg4 and different lipid forms of GalNAc-LcGg4, d16:1/18:0 and nitrobenzoxadiazole (NBD) (FIG. 16) were synthesized. The GalNAc- LcGg4-NBD lipid form represents a lipid form where 7 carbons on the N-acetylsphingosine (d18:1) is replaced by NBD functional group. The synthetic GSLs were subjected to MS/MS to study the impacts of epimeric glycans and various lipids including both natural and unnatural lipids. The LC retention time (Rt) of GalNAc-LcGg4 (d18:1/18:0), LcGg4 (d18:1/18:0), GlcNAc-LcGg4 (d18:1/18:0), GalNAc-LcGg4 (d16:1/18:0), and GalNAc-LcGg4-NBD were as follows, where all the m/z values correspond to [M+H]+ precursor ions:

| GSL ID | Rt (min) | Experimental (m/z) | Calculated (m/z) | Deviation (in ppm) |
|---|---|---|---|---|
| GalNAc-LcGg4 (d18:1/18:0) | 27.7 | 1296.8249 | 1296.8150 | 7.63 |
| LcGg4 (d18:1/18:0) | 27.7 | 1296.8249 | 1296.8150 | 7.63 |
| GlcNAc-LcGg4 (d18:1/18:0) | 27.7 | 1296.8249 | 1296.8150 | 7.63 |
| GalNAc-LcGg4 (d16:1/18:0) | 23.2 | 1268.7892 | 1268.7838 | 4.26 |
| GalNAc-LcGg4-NBD | 10.6 | 1376.7267 | 1376.7182 | 5.59 |

The fragmentation patterns and the nomenclature of product ions of LcGg4 are shown in FIG. 17. The collision energy was selected to be 25 eV, as it gave a relatively balanced distribution of all fragment ions. Under low collision energies, the relative intensities of large fragment ions such as B3 and Y2a/Y2b ions, increased, with the combined intensities of these two ions >70% and >57% of total intensities of all fragment ions at 15 and 20 eV, respectively. As a result, smaller fragment ions, such as B2, Z1, Y2aZ2 ions, were not formed in sufficient intensities. On the other hand, collision energies higher than 25 eV gave increased relative intensities of small fragment ions, such as B1 and Z0 ions, leading to a significant decrease in the relative intensity of large fragments ions. Therefore, a collision energy of 25 eV was chosen.

The MS/MS spectra of the isomers LcGg4, GalNAc-LcGg4, and GlcNAc-LcGg4, which differ only in the glycan structure, specifically, the two sugar residues on the glycan non-reducing end, were analyzed and compared. LcGg4 is a natural tumor-associated carbohydrate antigen and a marker of undifferentiated, malignant leukemia. It has N-acetylglucosamine (GlcNAc) and N-acetylgalactosamine (GalNAc) linked to the 3'- and 4'-O-positions of the core lactose, respectively. In GalNAc-LcGg4, the 3'-O-GlcNAc residue in LcGg4 was replaced with a GalNAc residue, whilst replacing the 4'-O-GalNAc residue with a GlcNAc resulted in GlcNAc-LcGg4. Hence, GalNAc-LcGg4 and GlcNAc-LcGg4 are epimers of LcGg4, i.e., different from LcGg4 only in the configuration of 4-OH group for one of the two non-reducing end sugar residues. All the major product ions in the MS/MS spectra of LcGg4, GalNAc-LcGg4, and GlcNAc-LcGg4 were characterized (FIG. 19). The carbohydrate product ions were mainly B and BY ions, including B1, B2Y2a/2b, B3Y2a/2b, B2 and B3 at m/z 204.09, 366.15, 528.20, 569.23, and 731.28, respectively. The results agreed well with the common observation that weak glycosidic bonds of carbohydrates are easily cleaved. For the same reason, the glycolipid product ions were mainly Z and Y ions, including Z0, Y0, Z1, Y1, Y2aZ2, Y2ab, Z2, and Y2a/Y2b at m/z 548.55, 566.56, 710.60, 728.62, 872.66, 890.67, 1075.74, and 1093.75, respectively. Clearly, the MS/MS spectra of all three GSLs are very similar.

To gain more insights into the differences in the fragmentation patterns of these epimeric GSLs, the product ions were compared. The relative intensities of the B and BY ions, as depicted in FIG. 18E, had the same pattern for all isomers, i.e., B3 ion being the most abundant followed by B1 and B3Y2a/2b ions, while B2 and B2Y2a/2b ions have relatively low intensities. FIG. 18D showed that the relative intensities of Y, Z, and other glycolipid ions also had the same pattern for all three isomers, i.e., Y2/Z2 ions being the most abundant followed by Z0/Y0 and then Z1/Y1 ions. The higher intensities of the combined B1 and Y2-related ions and combined B3- and Y0-related ions, as compared to those of the combined Y1 and B2-related ions, suggest that the glycosidic bond within the lactose motif is more stable than the glycosidic bonds of the non-reducing end GlcNAc and GalNAc residues and than that of the reducing end Glc residue under the current MS conditions. Another interesting finding was that the intensities of B1 ions (i.e., GlcNAc+ and/or GalNAc+) increased steadily from GalNAc-LcGg4 (with two GalNAc units) to LcGg4 (with a GalNAc and a GlcNAc units) to GlcNAc-LcGg4 (with two GlcNAc units). A plausible explanation for this result is that GlcNAc cleavage is easier than that of GalNAc or the GlcNAc+ cation is more stable than GalNAc+. The hypothesis is further supported by reduced relative intensities of the Y2aY2b and Y2a/2b ions from GalNAc-LcGg4 to LcGg4 and then to GlcNAc-LcGg4. FIG. 18F has also revealed an increase in the total carbohydrate product ion relative intensity and a decrease in the relative intensity of total glycolipid product ions from GalNAc-LcGg4 to LcGg4 and then GlcNAc-LcGg4, suggesting a similar trend for the glycosidic bond stability and the MS/MS fragmentation pattern as proposed.

Clearly, the MS/MS spectra of LcGg4, GalNAc-LcGg4, and GlcNAc-LcGg4 had the same fragmentation pattern and product ions. Although some minor differences in the relative intensities of their product ions were observed, these differences may not be sufficient to be utilized confidently for the characterization of specific stereoisomers, especially in complex mixtures, simply by MS/MS spectral analysis alone.

To understand the influences of lipid structures on the fragmentation pattern of natural GSLs, the MS/MS spectra of GalNAc-LcGg4 (d16:1/18:0), GalNAc-LcGg4 (d18:1/18:0), and GalNAc-LcGg4-NBD, which have the identical glycan but different ceramides, were probed and compared. As depicted in FIGS. 19A and B, the MS/MS spectra of GalNAc-LcGg4 (d16:1/18:0) and GalNAc-LcGg4 (d18:1/18:0) had the same fragmentation patterns, namely that they produced identical B and BY ions and the same types of Y and Z ions, which were uniformly different by m/z 28, equivalent to the mass difference of their lipids (by a —CH2CH2-unit). More significantly, the peak intensities of the corresponding glycolipid and carbohydrate product ions for these two GSLs, as shown in FIGS. 19D and E, were almost identical. FIG. 19F further demonstrated that the relative intensities of their total carbohydrate and total glycolipid product ions were also the same. These results confirmed that homologous lipids attached to a neutral GSL species would not have a significant impact on its MS/MS fragmentation patterns. Therefore, the MS/MS spectrum of one lipid form of a neutral GSL species may be used as the reference for the identification of its other natural lipid forms by the two-stage MS/MS spectral matching methodology.

Comparing the MS/MS spectra of GalNAc-LcGg4 (d18:1/18:0) and GalNAc-LcGg4-NBD that contains a fluorophore labeled lipid (FIGS. 19A and C) showed that they yielded identical B and BY ions and same type of Y and Z ions that were different by m/z 80—the molecular mass difference of lipids. These results suggested that GalNAc-LcGg4-NBD and GalNAc-LcGg4 had the same fragmentation pattern. However, the relative intensities of corresponding product ions (FIGS. 19D and E), as well as the relative intensities of their total carbohydrate and total glycolipid product ions (FIG. 19F), were different. For example, the intensities of the glycolipid product ions of GalNAc-LcGg4-NBD were much higher than that of GalNAc-LcGg4. The relative intensity increase of glycolipid product ions and the relative intensity decrease of carbohydrate product ions in the MS/MS spectra of NBD-modified GSL, compared to that of GSLs bearing aliphatic lipids, suggested that the presence of NBD had helped the formation of various glycolipid product ions. A plausible explanation for this result is that the aromatic substituent in NBD-modified LcGg4 may have stabilized the ions on lipid, thereby to elevate the formation of glycolipid product ions. Overall, these results have further validated that the types of ions produced by GSLs, i.e., their overall fragmentation patterns, are not significantly affected by the lipid structure; however, the relative intensities of various ions are affected by the lipid, if it can substantially stabilize product ions.

As the MS/MS spectra of isomeric LcGg4, GalNAc-LcGg4, and GlcNAc-LcGg4 are similar and cannot be directly used to differentiate them, these isomers were subsequently studied by means of LC-MS/MS. For this purpose, LcGg4, GalNAc-LcGg4, and GlcNAc-LcGg4, as well as the different lipid forms of GalNAc-LcGg4 including GalNAc-LcGg4-NBD, were mixed and subjected to reversed-phase (RP) LC-MS/MS analysis. The MS/MS data were evaluated by the two-step spectral matching method for GSL identification using the MS/MS spectra in FIGS. 18A-C and 19A-C as references, and the LC retention time (Rt) for each GSL is listed above. All different lipid forms of GalNAc-LcGg4, which were easily separable by RPLC, were unambiguously characterized and showed different Rt. However, the stereoisomers LcGg4, GalNAc-LcGg4, and GlcNAc-LcGg4, which were different only in the glycan structure, were inseparable by RPLC (co-elution at 27.7 min) and thus were not differentiable. Clearly, traditional LC-MS/MS may not be effective for the characterization of LcGg4, GalNAc-LcGg4, and GlcNAc-LcGg4, although GalNAc-LcGg4 and GlcNAc-LcGg4 have two different stereogenic centers.

In summary, this study demonstrated that variations in the lipid form of a neutral GSL species had nearly no impact on its fragmentation pattern and product ions. Thus, like gangliosides, the MS/MS spectrum of one lipid form of a neutral GSL species can also be utilized as the reference for identification of its other lipid forms by the method of two-stage MS/MS spectra matching. Further, careful analysis of the MS/MS spectra of LcGg4, GlcNAc-LcGg4, and GlcNAc-LcGg4 revealed that the glycosidic bond of GalNAc may be more stable than that of GlcNAc, which can be generally useful in carbohydrate research, including both MS studies of carbohydrates and their synthetic and biological applications. Further still, LC-MS/MS alone should be sufficient to distinguish lipid forms of a GSL but insufficient to differentiate stereoisomers, especially epimers, of GSLs. This work represents the first report on detailed MS studies of the epimers of a complex GSL carrying a branched tetrasaccharide and intact ceramide motifs, which was facilitated by our access to a series of synthetic and homogeneous GSLs with defined structures of the glycan and lipid. The results and conclusions of this work can be of general significance for MS analysis of the lipid forms and the isomers of other GSLs.

The synthesis and the analytical data of LcGg4, GalNAc-LcGg4, GlcNAc-LcGg4, GalNAc-LcGg4 (d16:1/18:0), and GalNAc-LcGg4-NBD were described in Rohokale et. al, J. Org. Chem., 2021, 86, 1633-1648. LcGg4 (2 mg), GalNAc-LcGg4 (1 mg), GalNAc-LcGg4 (d16:1/18:0) (1 mg), GalNAc-LcGg4-NBD (1 mg), and GlcNAc-LcGg4 (2 mg) were separately dissolved in methanol (1 mL) to form individual stock solutions with a GSL concentration of 1 and 2 mg mL$^{-1}$, respectively.

Each stock solution (50 µL) was added to methanol (1 mL) that contained 10 mM ammonium formate and 0.1% formic acid. The concentrations of the resultant GalNAc-LcGg4, GalNAc-LcGg4 (d16:1/18:0) and GalNAc-LcGg4-NBD samples were 50 µs mL$^{-1}$, and that of LcGg4 and GlcNAc-LcGg4 samples were 100 µg mL$^{-1}$. The GSL samples (5 µL) were then individually injected to a Waters Xevo G2-XS QT of instrument using electrospray ionization (ESI) in positive mode. The injection flow rate was 5 µL min$^{-1}$. The MS instrument was operated at a capillary voltage of 4.0 kV with a source temperature of 100° C. and desolvation temperature of 250° C. For MS/MS, collision induced dissociation (CID) at a consistent collision energy of 25 eV was used to achieve fragmentations.

After the above GSL stock solutions (10 µL each) were combined, methanol was added to get a total volume of 400 µL. Thus, the concentrations of GalNAc-LcGg4 (d18:1/18:0), GalNAc-LcGg4 (d16:1/18:0) and GalNAc-LcGg4-NBD in the resultant mixture were 25 µg mL$^{-1}$, and that of LcGg4 and GlcNAc-LcGg4 were 50 µs mL$^{-1}$. This GSL mixture (3 µL) was then injected to a Waters Xevo G2-XS QT of MS machine coupled with MSREC's Thermo LC system equipped with a C18 pre-column (3 mm×2 cm, 75 µm, 100 Å) and a Thermo Fisher Scientific Acclaim PepMap RSLC C18 column (300 µm×15 cm, 2 µm, 100 Å). The mobile phases used for LC were: (A) 60/40 (v/v) acetonitrile/water, and (B) 90/8/2 (v/v/v) isopropanol/acetonitrile/water, both containing 10 mM ammonium formate and 0.1% formic acid. The sample loaded onto the pre-column was washed with 98/2 (v/v) water/acetonitrile containing 0.1% formic acid at a 25 µL min$^{-1}$ flow rate for 5 min. Thereafter, the switching valve was activated to load the sample into the separation column. The gradient pump was operated at 50% B for 5 min before ramping to 98% B for 50 min and holding for 20 min at a constant flow rate of 5 µL min$^{-1}$. The MS conditions were the same as that of the direct infusion experiments.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

The invention claimed is:

1. A mass spectrometry (MS) based system configured to implement multi-stage MS/MS analysis for identification of experimental glycolipid samples, the MS based system comprising:

a mass spectrometer configured to receive and analyze an experimental glycolipid sample to determine experimental MS/MS spectral data of the experimental glycolipid sample;

a reference spectral database configured to store a plurality of reference glycolipid datasets, each of the reference glycolipid datasets corresponding to a reference glycolipid and comprising at least (a) reference glycan fragment data defining MS/MS spectra of a glycan portion of the reference glycolipid, and (b) reference lipid and/or glycolipid fragment data defining MS/MS spectra of a lipid portion of the reference glycolipid;

a memory storing program instructions; and a processor communicatively coupled to the memory and the reference spectral database, wherein the processor is configured to execute the program instructions to cause the processor to:

(1) implement a first stage analysis of glycan fragment data comprising:

determining, from the experimental MS/MS spectral data, experimental glycan fragment data defining MS/MS spectra of a glycan portion of the experimental glycolipid sample, identifying a matching reference glycan of a candidate reference glycolipid selected from the reference spectral database, wherein fragment data of the matching reference glycan comprises one or more MS/MS spectral values that correspond to one or more MS/MS spectral values of the experimental glycan fragment data, determining, based on the matching reference glycan of the candidate reference glycolipid, a glycan structure of the glycan portion of the experimental glycolipid, and (2) implement a second stage analysis of lipid and/or glycolipid fragment data comprising:

determining, from the experimental MS/MS spectral data, experimental lipid and/or glycolipid fragment data defining MS/MS spectra of a lipid portion of the experimental glycolipid sample, rule-based shifting, by the processor, one or more mass values of the reference lipid and/or glycolipid fragment data of the candidate reference glycolipid, while maintaining, during the rule-based shifting, the experimental glycan fragment data identified during the first stage analysis, to generate shifted reference lipid and/or glycolipid fragment data, performing a spectral comparison of one or more MS/MS spectral values of the shifted reference lipid and/or glycolipid fragment data with one or more MS/MS spectral values of the experimental lipid and/or glycolipid fragment data, and determining, based on reference lipid and/or glycolipid fragment data of the candidate reference glycolipid, a lipid structure of the lipid portion of the experimental glycolipid, wherein, based on the spectral comparison, the experimental glycolipid sample is determined to be of a same glycolipid species as the candidate reference glycolipid, the lipid structure of the lipid portion of the experimental glycolipid being different from a lipid structure of the candidate reference glycolipid as characterized by a difference between the experimental lipid and/or glycolipid fragment data and the reference lipid and/or glycolipid fragment data.

2. The MS based system of claim 1, wherein the experimental glycolipid sample is a human or animal bodily fluid or tissue based glycolipid sample.

3. The MS based system of claim 1, wherein the experimental glycolipid sample includes one or more unidentified glycolipids as one or more corresponding biomarkers.

4. The MS based system of claim 1, wherein the one or more MS/MS spectral values of the matching reference glycan fragment data correspond to one or more MS/MS spectral values of the experimental glycan fragment data by at least a glycan based relative intensity threshold value; or the one or more MS/MS spectral values of the experimental lipid and/or glycolipid fragment data correspond to one or more MS/MS spectral values of the reference lipid and/or glycolipid fragment data or the shifted reference lipid and/or glycolipid fragment data by at least a lipid and/or glycolipid based relative intensity threshold value.

5. The MS based system of claim 1 further comprising generating a matching score for the experimental glycolipid sample based on a comparison of MS/MS spectra of (1) the reference glycan fragment data and either the shifted reference lipid and/or glycolipid fragment data or the reference lipid and/or glycolipid fragment data, with (2) the experimental glycan fragment data and the experimental lipid and/or glycolipid fragment data.

6. The MS based system of claim 1, wherein the reference spectral database is updated with a new glycolipid dataset corresponding to the experimental glycolipid sample, the new glycolipid dataset stored in the reference spectral database, and the new glycolipid dataset comprising at least (a) the experimental glycan fragment data, and (b) the experimental lipid and/or glycolipid fragment data.

7. The MS based system of claim 1, wherein the processor is communicatively coupled to the mass spectrometer, and where the processor is further configured to receive the MS/MS spectral data of the experimental glycolipid sample from the mass spectrometer.

8. The MS based system of claim 1, wherein the mass spectrometer comprises collision-induced dissociation (CID).

9. The MS based system of claim 1, wherein the one of more mass values of the reference lipid and/or glycolipid fragment data are shifted by 14n, 2n', or a combination thereof.

10. The MS based system of claim 1, wherein the one or more mass values of the reference lipid and/or glycolipid fragment data are shifted by the mass of an isotope label, a chemical modification, a chemical tag, or a combination thereof.

11. A mass spectrometry (MS) based method of implementing multi-stage MS/MS analysis for identification of experimental glycolipid samples, the MS based method comprising:

(1) implementing, by a processor communicatively coupled to a memory and a reference spectral database, a first stage analysis of glycan fragment data comprising:

determining, from experimental MS/MS spectral data of an experimental glycolipid sample as analyzed by a mass spectrometer, experimental glycan fragment data defining MS/MS spectra of a glycan portion of the experimental glycolipid sample, identifying a matching reference glycan of a candidate reference glycolipid selected from the reference spectral database, wherein the spectral database stores a plurality of reference glycolipid datasets, each of the reference glycolipid datasets corresponding to a reference glycolipid and comprising at least (a) reference glycan fragment data defining MS/MS spectra of a glycan portion of the reference glycolipid, and (b) reference lipid and/or glycolipid fragment data defining MS/MS spectra of a lipid portion of the reference glycolipid, and wherein fragment data of the matching reference glycan comprises one or more MS/MS spectral values that correspond to one or more MS/MS spectral values of the experimental glycan fragment data, and determining, based on the matching reference glycan of the candidate reference glycolipid, a glycan structure of the glycan portion of the experimental glycolipid, and (2) implementing, by the processor, a second stage analysis of lipid and/or glycolipid fragment data comprising:

determining, from the experimental MS/MS spectral data, experimental lipid and/or glycolipid fragment data defining MS/MS spectra of a lipid portion of the experimental glycolipid sample, rule-based shifting, by the processor, one or more mass values of the reference lipid and/or glycolipid fragment data of the candidate reference glycolipid, while maintaining, during the rule-based shifting, the experimental glycan fragment data identified during the first stage analysis, to generate shifted reference lipid and/or glycolipid fragment data, performing a spectral comparison of one or more MS/MS spectral values of the shifted reference lipid and/or glycolipid fragment data with one or more MS/MS spectral values of the experimental lipid and/or glycolipid fragment data, and determining, based on reference lipid and/or glycolipid fragment data of the candidate reference glycolipid, a lipid structure of the lipid portion of the experimental glycolipid, wherein, based on the spectral comparison, the experimental glycolipid sample is determined to be of a same glycolipid species as the candidate reference glycolipid, the lipid structure of the lipid portion of the experimental glycolipid being different from a lipid structure of the candidate reference glycolipid as characterized by a difference between the experimental lipid and/or glycolipid fragment data and the reference lipid and/or glycolipid fragment data.

12. The MS based method of claim 11, wherein the experimental glycolipid sample is a human or animal bodily fluid or tissue based glycolipid sample.

13. The MS based method of claim 11, wherein the experimental glycolipid sample includes one or more unidentified glycolipids as one or more corresponding biomarkers.

14. The MS based method of claim 11, wherein the one or more MS/MS spectral values of the matching reference glycan fragment data correspond to one or more MS/MS spectral values of the experimental glycan fragment data by at least a glycan based relative intensity threshold value; or the one or more MS/MS spectral values of the experimental lipid and/or glycolipid fragment data correspond to one or more MS/MS spectral values of the reference lipid and/or glycolipid fragment data or the shifted reference lipid and/or glycolipid fragment data by at least a lipid and/or glycolipid based relative intensity threshold value.

15. The MS based method of claim 11, wherein a matching score is generated, by the processor, for the experimental glycolipid sample based on a comparison of MS/MS spectra of (1) the reference glycan fragment data and either the shifted reference lipid and/or glycolipid fragment data or the reference lipid and/or glycolipid fragment data, with (2) the experimental glycan fragment data and the experimental lipid and/or glycolipid fragment data.

16. The MS based method of claim 11, wherein the reference spectral database is updated with a new glycolipid dataset corresponding to the experimental glycolipid sample, the new glycolipid dataset stored in the reference spectral database, and the new glycolipid dataset comprising at least (a) the experimental glycan fragment data, and (b) the experimental lipid and/or glycolipid fragment data.

17. The MS based method of claim 11, wherein the processor is communicatively coupled to the mass spectrometer, and where the processor is further configured to receive the MS/MS spectral data of the experimental glycolipid sample from the mass spectrometer.

18. The MS based method of claim 11, wherein the mass spectrometer comprises collision-induced dissociation (CID).

19. The MS based method of claim 11, wherein the one or more mass values of the reference lipid and/or glycolipid fragment data are shifted by 14n, 2n', or both.

20. The MS based method of claim 11, wherein the one or more mass values of the reference lipid and/or glycolipid fragment data are shifted by the mass of an isotope label, a chemical modification, a chemical tag, or a combination thereof.

* * * * *